(12) United States Patent
Rodgers et al.

(10) Patent No.: US 7,384,550 B2
(45) Date of Patent: *Jun. 10, 2008

(54) GLAUCOMA IMPLANT HAVING MEMS FILTER MODULE

(75) Inventors: M. Steven Rodgers, Albuquerque, NM (US); Jeffry J. Sniegowski, Tijeras, NM (US); Paul J. McWhorter, Albuquerque, NM (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 485 days.

This patent is subject to a terminal disclaimer.

(21) Appl. No.: 11/065,183

(22) Filed: Feb. 24, 2005

(65) Prior Publication Data

US 2005/0184004 A1    Aug. 25, 2005

Related U.S. Application Data

(63) Continuation-in-part of application No. 10/911,424, filed on Aug. 4, 2004, now Pat. No. 7,226,540.

(60) Provisional application No. 60/547,252, filed on Feb. 24, 2004.

(51) Int. Cl.
  *B01D 63/08*  (2006.01)
  *A61M 5/165*  (2006.01)
  *A61M 37/00*  (2006.01)
  *B01D 63/00*  (2006.01)
  *B01D 61/00*  (2006.01)

(52) U.S. Cl. .......................... 210/321.84; 210/321.75; 210/511; 210/500.22; 210/500.26; 137/833; 422/101; 604/6.09; 604/8

(58) Field of Classification Search ...................... None
See application file for complete search history.

(56) References Cited

U.S. PATENT DOCUMENTS

| | | |
|---|---|---|
| 3,159,161 A | 12/1964 | Ness |
| 3,788,327 A | 1/1974 | Donowitz et al. |
| 3,949,750 A | 4/1976 | Freeman |
| 4,014,335 A | 3/1977 | Arnold |

(Continued)

FOREIGN PATENT DOCUMENTS

DE    19922623 A1    7/2000

(Continued)

OTHER PUBLICATIONS

PCT Search Report dated Nov. 10, 2006; Application No. PCT/US2006/024175.

(Continued)

*Primary Examiner*—Krishnan S Menon
(74) *Attorney, Agent, or Firm*—James J. Murtha

(57) ABSTRACT

Various MEMS filter elements or modules are disclosed, and which may be used in a glaucoma implant (490). One such MEMS filter module (34) includes a first film (70) and a second film (46) that are spaced and interconnected by a plurality of supports (78). A plurality of first flow ports (74) extend through the first film (70), and a plurality of second flow ports (50) extend through the second film (46). A plurality of annular filter walls (54) extend from the second film (46) toward the first film (70), and are separated therefrom by a filter trap gap (58).

66 Claims, 36 Drawing Sheets

U.S. PATENT DOCUMENTS

| | | | |
|---|---|---|---|
| 4,037,604 A | 7/1977 | Newkirk | |
| 4,168,697 A | 9/1979 | Cantekin | |
| 4,402,681 A | 9/1983 | Haas et al. | |
| 4,634,418 A | 1/1987 | Binder | |
| 4,750,901 A | 6/1988 | Molteno | |
| 4,787,885 A | 11/1988 | Binder | |
| 4,915,684 A | 4/1990 | MacKeen et al. | |
| 4,936,825 A | 6/1990 | Ungerleider | |
| 4,959,048 A | 9/1990 | Seder et al. | |
| 4,968,296 A | 11/1990 | Ritch et al. | |
| 5,041,081 A | 8/1991 | Odrich | |
| 5,073,163 A | 12/1991 | Lippman | |
| 5,092,837 A | 3/1992 | Ritch et al. | |
| 5,127,901 A | 7/1992 | Odrich | |
| 5,273,750 A | 12/1993 | Homiger et al. | |
| 5,300,020 A | 4/1994 | L'Esperance, Jr. | |
| 5,338,291 A | 8/1994 | Speckman et al. | |
| 5,346,464 A | 9/1994 | Camras | |
| 5,372,577 A | 12/1994 | Underleider | |
| 5,380,328 A * | 1/1995 | Morgan | 606/70 |
| 5,433,701 A | 7/1995 | Rubinstein | |
| 5,454,796 A | 10/1995 | Krupin | |
| 5,496,372 A * | 3/1996 | Hamamoto et al. | 623/23.54 |
| 5,558,630 A | 9/1996 | Fisher | |
| 5,626,558 A | 5/1997 | Suson | |
| 5,626,559 A | 5/1997 | Solomon | |
| 5,651,900 A | 7/1997 | Keller et al. | |
| 5,702,414 A | 12/1997 | Richter et al. | |
| 5,743,868 A | 4/1998 | Brown et al. | |
| 5,753,014 A | 5/1998 | Van Rijn | |
| 5,807,302 A | 9/1998 | Wandel | |
| 5,807,406 A * | 9/1998 | Brauker et al. | 424/423 |
| 5,817,099 A | 10/1998 | Skolik et al. | |
| 5,824,086 A | 10/1998 | Silvestrini | |
| 5,868,697 A | 2/1999 | Richter et al. | |
| 5,879,319 A | 3/1999 | Pynson et al. | |
| 5,919,364 A | 7/1999 | Lebouitz et al. | |
| 5,968,058 A | 10/1999 | Richter et al. | |
| 6,001,386 A | 12/1999 | Ashton et al. | |
| 6,007,511 A | 12/1999 | Prywes | |
| 6,027,470 A | 2/2000 | Mendius | |
| 6,186,974 B1 | 2/2001 | Allan et al. | |
| 6,203,513 B1 | 3/2001 | Yaron et al. | |
| 6,234,175 B1 | 5/2001 | Zhou et al. | |
| 6,261,256 B1 | 7/2001 | Ahmed | |
| 6,306,114 B1 | 10/2001 | Freeman et al. | |
| 6,450,984 B1 | 9/2002 | Lynch et al. | |
| 6,468,283 B1 | 10/2002 | Richter et al. | |
| 6,494,857 B1 | 12/2002 | Neuhann | |
| 6,508,779 B1 | 1/2003 | Suson | |
| 6,510,600 B2 | 1/2003 | Yaron et al. | |
| 6,533,768 B1 | 3/2003 | Hill | |
| 6,544,208 B2 | 4/2003 | Either et al. | |
| 6,544,249 B1 | 4/2003 | Yu et al. | |
| 6,558,342 B1 | 5/2003 | Yaron et al. | |
| 6,589,198 B1 | 7/2003 | Soltanpour et al. | |
| 6,595,945 B2 | 7/2003 | Brown | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,699,210 B2 | 3/2004 | Williams et al. | |
| 6,699,211 B2 | 3/2004 | Savage | |
| 6,706,275 B1 | 3/2004 | Camp | |
| 6,726,664 B2 | 4/2004 | Yaron et al. | |
| 6,736,197 B2 | 5/2004 | Nozaki et al. | |
| 6,736,791 B1 | 5/2004 | Tu et al. | |
| 6,780,164 B2 | 8/2004 | Bergheim et al. | |
| 6,827,699 B2 | 12/2004 | Lynch et al. | |
| 6,827,700 B2 | 12/2004 | Lynch et al. | |
| 6,881,197 B1 | 4/2005 | Nlgam | |
| 6,881,198 B2 | 4/2005 | Brown | |
| 6,913,697 B2 * | 7/2005 | Lopez et al. | 210/644 |
| 6,955,656 B2 | 10/2005 | Bergheim et al. | |
| 6,981,958 B1 | 1/2006 | Gharib et al. | |
| 2002/0013546 A1 | 1/2002 | Grieshaber et al. | |
| 2002/0128560 A1 | 9/2002 | Urich | |
| 2002/0143284 A1 | 10/2002 | Tu et al. | |
| 2002/0169130 A1 | 11/2002 | Tu et al. | |
| 2002/0177856 A1 | 11/2002 | Richter et al. | |
| 2002/0188308 A1 | 12/2002 | Tu et al. | |
| 2003/0055372 A1 | 3/2003 | Lynch et al. | |
| 2003/0060752 A1 | 3/2003 | Bergheim et al. | |
| 2003/0069637 A1 | 4/2003 | Lynch et al. | |
| 2003/0080060 A1 | 5/2003 | Gulvin | |
| 2003/0088260 A1 | 5/2003 | Smedley et al. | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | |
| 2003/0191428 A1 | 10/2003 | Bergheim et al. | |
| 2003/0212383 A1 | 11/2003 | Cote et al. | |
| 2003/0220602 A1 | 11/2003 | Lynch et al. | |
| 2003/0229303 A1 | 12/2003 | Haffner et al. | |
| 2003/0232015 A1 | 12/2003 | Brown et al. | |
| 2003/0236483 A1 | 12/2003 | Ren | |
| 2004/0015140 A1 | 1/2004 | Shields | |
| 2004/0024345 A1 | 2/2004 | Gharib et al. | |
| 2004/0073156 A1 | 4/2004 | Brown | |
| 2004/0073231 A1 | 4/2004 | Juan, Jr. et al. | |
| 2004/0088048 A1 | 5/2004 | Richter et al. | |
| 2004/0102729 A1 | 5/2004 | Haffner et al. | |
| 2004/0111050 A1 | 6/2004 | Smedley et al. | |
| 2004/0127843 A1 | 7/2004 | Tu et al. | |
| 2004/0154972 A1 | 8/2004 | Cho et al. | |
| 2004/0193095 A1 | 9/2004 | Shadduck | |
| 2004/0210181 A1 | 10/2004 | Vass et al. | |
| 2004/0225250 A1 | 11/2004 | Yablonski | |
| 2004/0249333 A1 | 12/2004 | Bergheim et al. | |
| 2004/0254517 A1 | 12/2004 | Quiroz-Mercado et al. | |
| 2004/0254521 A1 | 12/2004 | Simon | |
| 2004/0260228 A1 | 12/2004 | Lynch et al. | |
| 2004/0265182 A1 | 12/2004 | Chen et al. | |
| 2005/0038334 A1 | 2/2005 | Lynch et al. | |
| 2005/0049578 A1 | 3/2005 | Tu et al. | |
| 2005/0090806 A1 | 4/2005 | Lynch et al. | |
| 2005/0090807 A1 | 4/2005 | Lynch et al. | |
| 2005/0119601 A9 | 6/2005 | Lynch et al. | |
| 2005/0119636 A1 | 6/2005 | Haffner et al. | |
| 2005/0125003 A1 | 6/2005 | Pinchuk et al. | |
| 2005/0133436 A1 * | 6/2005 | Kneezel | 210/321.84 |
| 2005/0148925 A1 | 7/2005 | Rottenberg et al. | |
| 2005/0184003 A1 | 8/2005 | Rodgers et al. | |
| 2005/0184004 A1 | 8/2005 | Rodgers et al. | |
| 2005/0194303 A1 | 9/2005 | Sniegowski et al. | |
| 2005/0197613 A1 | 9/2005 | Sniegowski et al. | |
| 2005/0197653 A1 | 9/2005 | Sniegowski et al. | |
| 2005/0209549 A1 | 9/2005 | Bergheim et al. | |
| 2005/0209550 A1 | 9/2005 | Bergheim et al. | |
| 2005/0266047 A1 | 12/2005 | Tu et al. | |
| 2005/0267398 A1 | 12/2005 | Protopsaltis et al. | |
| 2005/0268722 A1 | 12/2005 | Tai et al. | |
| 2005/0271704 A1 | 12/2005 | Tu et al. | |
| 2005/0273033 A1 | 12/2005 | Grahn et al. | |
| 2005/0288617 A1 | 12/2005 | Yaron | |
| 2005/0288619 A1 | 12/2005 | Gharib et al. | |

FOREIGN PATENT DOCUMENTS

| | | |
|---|---|---|
| DE | 19922623 C2 | 10/2002 |
| WO | WO 01/50943 A3 | 7/2001 |
| WO | WO0150943 | 7/2001 |
| WO | WO/99175 A1 | 12/2001 |
| WO | WO03/092564 A1 | 11/2003 |
| WO | WO 2005/081968 | 9/2005 |
| WO | WO2005081967 | 9/2005 |

| | | |
|---|---|---|
| WO | WO 2005/105197 | 11/2005 |

OTHER PUBLICATIONS

Tae Seok Sim and Yong-Kweon Kim; A Study on the Passive Microvalve Applicable to Drainage Device for Glaucoma; Journal of Semiconductor Technology and Science, Dec. 2002 vol. 2., No. 4.

Spiegel, D.; Schefthaler M.; Kobuch, K.; Outflow Facilities Through Descemet's Membrane in Rabbits; Graefes Arch Clin Exp Ophthalmol Feb. 2002; 240 (2):111-3.

[No Authors listed] Krupin Eye Value With Disk for Filtration Surgery. The Krupin Eye Valve Filtering Surgery Study Group. Ophthalmology. Apr. 1994; 101(4):651-8.

AGFID Project Team; Cell and Protein Adhesion Studies in Glaucoma Drainage Device Development; Br. J. Ophthalmol. 1999; 83; 1168-1171.

Bruce Allan; Closer to Nature: New Biomaterials and Tissue Engineering in Ophthalmology; Br. J. Ophthalmol 1999; 83; 1235-1240.

AGFID Project Team; Experimental Flow Studies in Glaucoma Drainage Device Development; Br. J. Ophthalmol 2001; 85; 1231-1236.

Yael Hanein; Y. Vickie Pan; Buddy D. Ratner; Denice D. Denton; Karl F. Bohringer; Micromachining of Non-Fouling Coatings for BIO-MEMS Applications; Sensors & Actuators B 81 Aug. 2001.

Patty Chen; Eugene Lim; Kin-Joe Sham; Adiel Smith; and Patrick Willoughby; FDA Report: Smartflow Glaucoma Stent; Jan. 9, 2003 Submitting to Myron Spector & I.V. Yannas.

K.S. Lim, B.D.S. Allan, AW Lloyd, A Muir, PT Khaw; Glaucoma Drainage Devices; Past, Present and Future; Br. J. Ophthalmol 1998;82; 1083-1089.

D.J. Howorth; Feasibility Study for a Micromachined Glaucoma Drainage Device; MSc Thesis From Cranfield University 2001-2002; Sep. 13, 2002.

Cristina Rodica Neagu, a Medical Microactuator Based on an Electrochemical Principle, Sep. 4, 1966; Roemania.

* cited by examiner

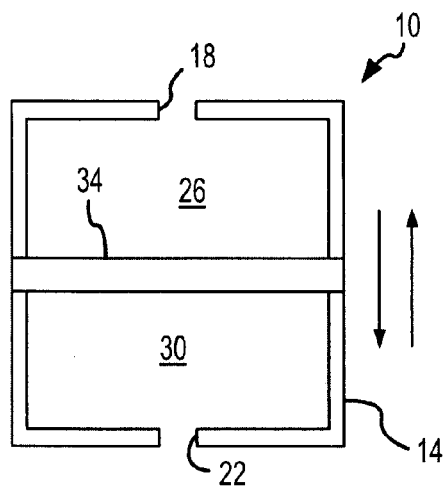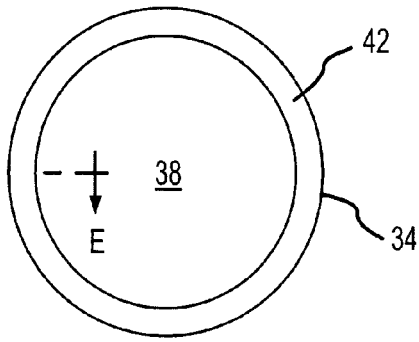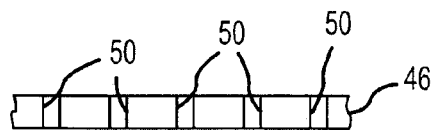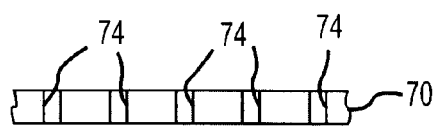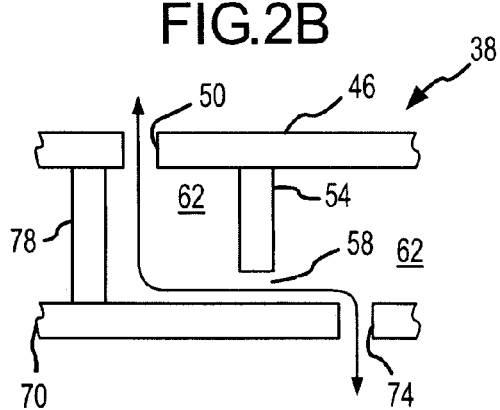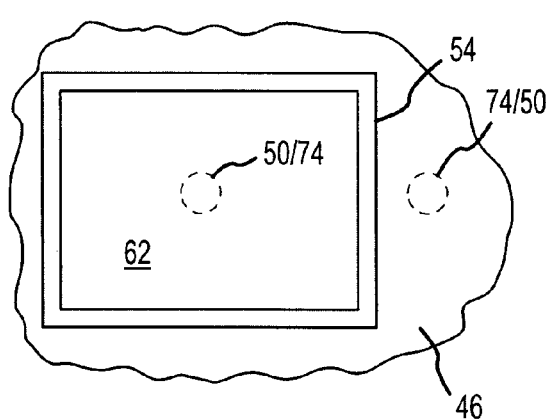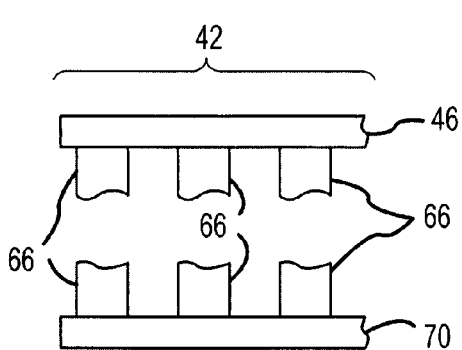

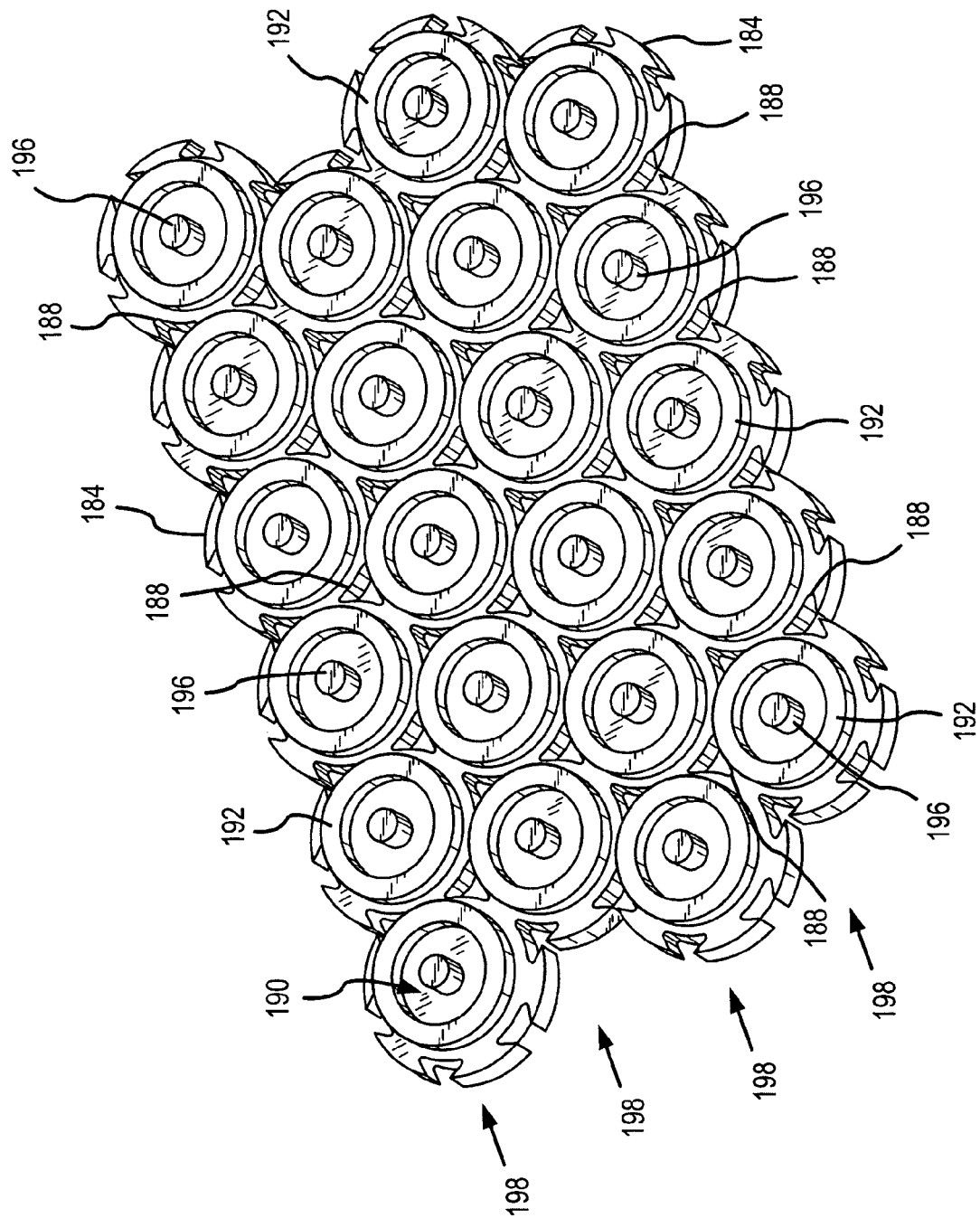

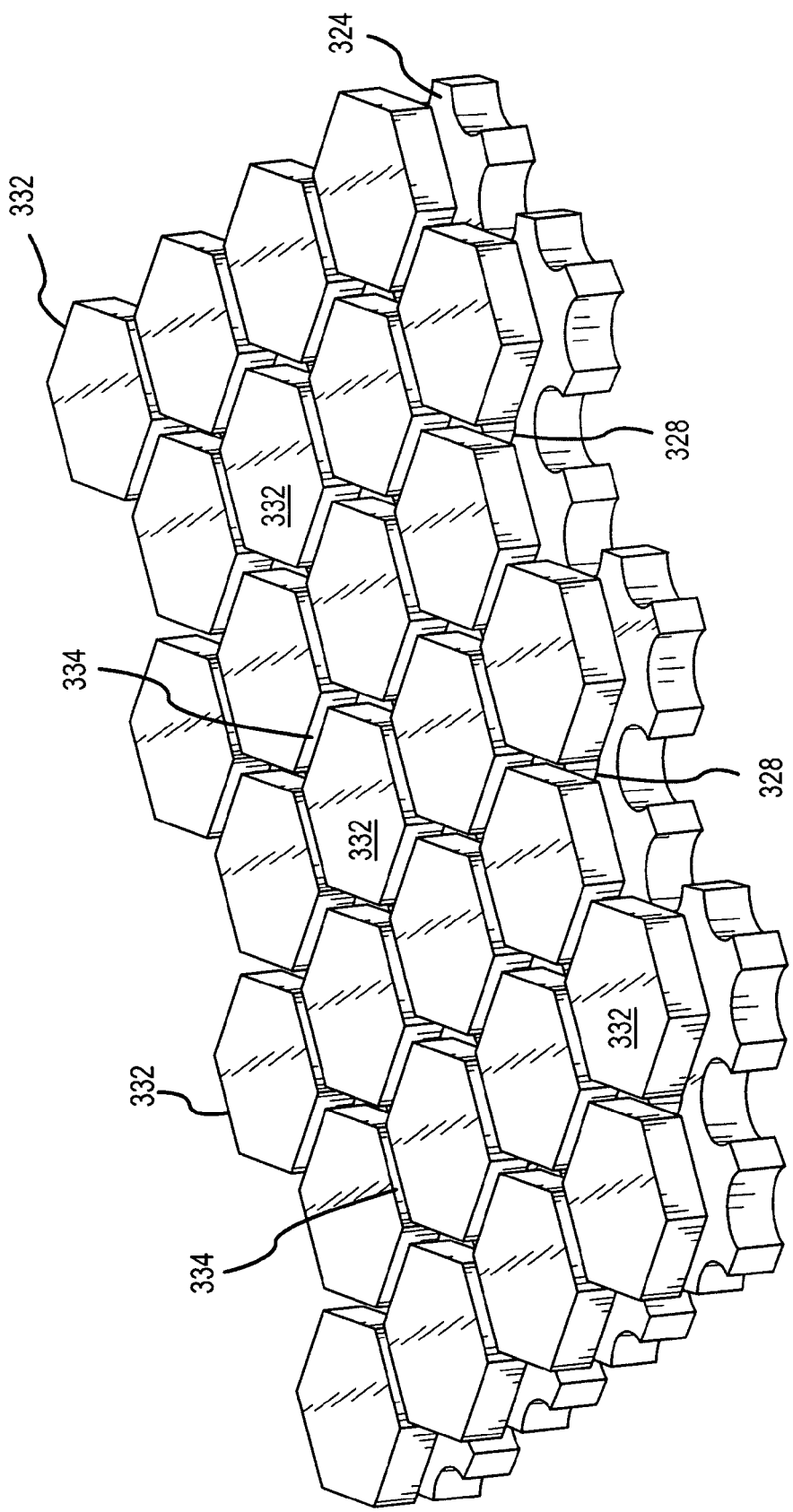

GLAUCOMA IMPLANT HAVING MEMS FILTER MODULE

CROSS REFERENCE TO RELATED APPLICATIONS

This patent application is a continuation-in-part of, and claims priority under 35 U.S.C. §120 to, U.S. patent application Ser. No. 10/911,424, that is entitled "MEMS FILTER MODULE, and that was filed on Aug. 4, 2004, now U.S. Pat. No. 7,226,540, and further claims priority under 35 U.S.C. §119 to U.S. Provisional Patent Application Ser. No. 60/547,252, that is entitled "MEMS FILTER MODULE," and that was filed on Feb. 24, 2004. The entire disclosure of each of the above-noted patent applications is incorporated by reference in their entirety herein.

FIELD OF THE INVENTION

The present invention generally relates to field of filters and, more particularly, to an implant that may be used to treat glaucoma and that utilizes a filter module that is microfabricated using films in at least two different fabrication levels.

BACKGROUND OF THE INVENTION

Filters are used in a large number of applications. The filtering media used by a filter may be in the form of a porous material or combination of porous materials. Both the pore size and the distribution of pores may of course have an effect on the filtering capabilities of the filtering media. For instance, if the filtering media is produced in a manner where adjacent pores could overlap, a larger pore may be formed. Although this may be acceptable for certain applications, it may not be for others (e.g., filtering biological fluids).

BRIEF SUMMARY OF THE INVENTION

The present invention generally relates to a MEMS filter module that may be inserted into a flow of any appropriate type and in any appropriate manner (e.g., by disposing the MEMS filter module into a housing through which a flow is directed). Generally, the MEMS filter modules described herein are microfabricated. There are a number of microfabrication technologies that are commonly characterized as "micromachining," including without limitation LIGA (Lithographie, Galvonoformung, Abformung), SLIGA (sacrificial LIGA), bulk micromachining, surface micromachining, micro electrodischarge machining (EDM), laser micromachining, 3-D stereolithography, and other techniques. Hereafter, the term "MEMS filter module" or the like means any such filtering device that is fabricated using a technology that allows realization of a feature size of about 10 microns or less.

One filter module in accordance with the present invention generally includes a first plate or film having a plurality of first flow ports that extend through its entire vertical extent or thickness, as well as a second plate or film that is spaced (e.g., vertically, such as when the filter module is in a first orientation) from this first film and that has a plurality of second flow ports that extend through its entire vertical extent or thickness. A plurality of filter walls are spaced on and extend from the second film in the direction of the first film. A gap between each filter wall and the first film defines a filter trap, such that there are then a plurality of filter traps. A first annular seal extends between the first and second films such that the first film, the second film, and the first annular seal collectively define an enclosed space. The region bounded by this first annular seal may be characterized as a filtering region. All of the filter walls, filter traps, first flow ports, and second flow ports are located in this filtering region. A plurality of posts or other supports extend between and interconnect the first and second films in the filtering region as well.

A first aspect is directed to the above-noted type of MEMS filter module, where each of the filter walls have an annular extent in a plan view of the surface of the second film from which the plurality of filter walls extend. "Annular" in relation to the first aspect means that each filter wall is defined by a closed perimeter, and does not limit the filter wall to a "circular" configuration in the noted plan view. A second aspect is directed to the above-noted type of MEMS filter module, where the number of supports in the filtering region is no less than the number of filter walls. Stated another way, there are at least as many supports in the filtering region as there are filter walls. A third aspect is directed to the above-noted type of MEMS filter module, where there are at least two first flow ports (the first film) and at least two second flow ports (the second film) associated with each filter trap. Therefore, any "plugging" of a particular first flow port or a second flow port should not totally disable its corresponding filter trap.

Various refinements exist of the features noted in relation to the MEMS filter module associated with any of the first through the third aspects of the present invention. Further features may also be incorporated in the MEMS filter module associated with any of the first through the third aspects of the present invention as well. These refinements and additional features may exist individually or in any combination. Initially, the above-noted first, second, and third aspects may be used individually or in any combination. The MEMS filter module may be of any appropriate configuration, may be adapted for use in any appropriate filter housing or structure for receiving the same, may be used to filter any appropriate fluid, may be used to filter any appropriate flow, and may be used for any appropriate application. Although the MEMS filter module will typically be separately fabricated from the filter housing and separately mounted thereto in any appropriate manner, the present invention is not limited to such a configuration.

Both the first film and the second film of the MEMS filter module associated with any of the first through the third aspects may have a maximum thickness of about 10 microns, and more typically within the range of about 1 micron to about 3 microns. Any appropriate material may be used for the first and second films. Although any appropriate microfabrication technique may be used in relation to this MEMS filter module, surface micromachining is a preferred approach, using materials such as polysilicon, silicon carbide, silicon nitride, polysilicon germanium, and tungsten for the first and second films, as well as for the filter wall. Typically the first and second films and the filter wall(s) will all be fabricated from the same material. The MEMS filter module also will typically be separated from any substrate that is used in the fabrication of the MEMS filter module prior to using the same in a filtering application (e.g., prior to disposing the same in the relevant filter housing or other structure for receiving the MEMS filter module).

The first and second films used by the MEMS filter module of any of the first through the third aspects may define its upper and lower boundaries or opposing extremes for the MEMS filter module. The first and/or second films each could also be an "intermediate" film in the MEMS filter module. One embodiment has a lower film that is vertically spaced from the first film on the opposite side thereof in relation to the second film. That is, the first film is located at an intermediate elevation between the second film and the lower film. This lower film may include a plurality of flow ports extending therethrough as well.

The filter walls used by the MEMS module of any of the first through the third aspects may be of an annular configuration or have a closed perimeter. Representative annular configurations for the filter walls include without limitation circular, square, and rectangular. In the case where the filter walls are annular, the corresponding filter trap will thereby also be annular. This may be of benefit for maintaining a desired flow rate through the MEMS filter module. Filter wall configurations other than annular may be used in relation to the above-noted second and third aspects as well. In one embodiment, each filter wall extends from the second film and terminates prior to reaching the surface of the first film that faces the surface of the second film from which the filter walls extend. In this case, each filter trap gap is defined by a distal end of a filter wall and the surface of the first film that faces the surface of the second film from which the filter walls extend. In another embodiment, an area encompassed by projecting each of the filter walls onto the first film does not encompass any of the first flow ports (e.g., each of the first flow ports are offset from each of the filter walls).

The filter traps associated with the MEMS filter module of any of the first through the third aspects are each defined by a space between the first film and each of the various filter walls that extend from the second film. Preferably the filter traps are defined by the space between the distal end of each of the filter walls and the first film. That is, in this particular instance the filter walls do not extend all the way to the first film. In one embodiment, the height of this gap is about 0.4 microns or less. Any appropriate gap size may be utilized.

The "density" of the supports that interconnect the first and second films throughout the filtering region may be selected to provide a desired degree of rigidity in relation to the anticipated flow rate(s) through the MEMS filter module of any of the first through the third aspects, may be selected to precisely maintain the magnitude of each filter trap throughout the filtering region for the anticipated flow rate(s) through the MEMS filter module of any of the first through the third aspects, or both. The second aspect again provides that there is at least one such support in the filtering region for each filter wall. In one embodiment, the maximum spacing between adjacent pairs of supports in the filtering region is no more than 100 microns, and may be on the order of 5 microns to about 20 microns. These supports may be of any appropriate size, shape, and/or configuration.

Multiple filter trap chambers may be associated with each filter trap of the MEMS filter module of any of the first through the third aspects. Each such filter trap chamber may be defined by the space between the first and second films. A first filter trap chamber may be the space "bounded" by each annular filter wall, and a second filter trap chamber may be the space between the various annular filter walls. The volume of each first filter trap chamber and the volume of the second filter trap chamber may be larger than the volume of any first flow port or any second flow port, although such need not be the case. In any case, the flow path through the MEMS filter module will either be into a first filter trap chamber, through the associated filter trap, and then into the second filter trap chamber, or the reverse.

More than one annular seal may be provided between the first and second films in the case of the MEMS filter module of any of the first through the third aspects. For instance, a second annular seal may be spaced outwardly from the first annular seal, and may extend between and interconnect the first and second films as well. A third annular seal may be spaced outwardly from the second annular seal, and may extend between and interconnect the first and second films as well. Using multiple annular seals reduces the potential for undesirable leakage out of the filtering region. Stated another way, multiple annular seals increase the likelihood that all flow through the MEMS filter module will be directed through the various filter traps. In one embodiment, the width of a perimeter region having at least one annular seal is at least about 3 microns to about 4 microns, and may be on the order of about 20 microns to about 25 microns.

A fourth aspect of the present invention is generally directed to a MEMS filter module having a first film having a plurality of first flow ports. A first chamber is fluidly connected with at least one of the first flow ports. A second film is spaced (e.g., vertically, when the MEMS filter module is disposed in a first orientation) from the first film and includes a plurality of second flow parts, and a second chamber is fluidly connected with at least one of the second flow parts. A first filter wall extends from the second film in the direction of the first film, and a first filter trap is defined in part by this first filter wall. The first and second chambers are fluidly connected by the filter trap gap.

Various refinements exist of the features noted in relation to the MEMS filter module of the fourth aspect. Further features may also be incorporated into the MEMS filter module of the fourth aspect as well. These refinements and additional features may exist individually or in any combination. Initially the various features discussed above in relation to the first through the third aspects may be used by this fourth aspect, individually or in any combination.

The first and second films may define the extremes of the MEMS filter in the case of the fourth aspect. One or both of the first and second films also may be disposed at an intermediate location or elevation within the MEMS filter module. In one embodiment, the filter trap gap is defined between the first filter wall and the first film. In another embodiment, at least one intermediate film section is disposed at an intermediate location or elevation between the first and second films and is interconnected with each by an appropriate support. Here the filter trap gap is defined between the first filter wall and the intermediate film section. In the case where a plurality of filter walls are utilized, there will be a corresponding number of intermediate film sections. An annular gap may exist around the perimeter of each such intermediate film section to fluidly communicate with the lower flow ports in the lower film.

A fifth aspect of the present invention is directed to a method for fabricating a MEMS filter module. A first film is formed in overlying relation to a substrate. A first flow aperture is formed down through the entire vertical extent of the first film. A first sacrificial film is formed directly on the upper surface of the first film and will typically fill the first flow port aperture. A filter wall aperture is formed down through the entire vertical extent of the first sacrificial film, and thereby exposes a corresponding portion of the first film. Additional sacrificial material is thereafter deposited at least on the portion of the first film that is exposed by the filter wall aperture (i.e., on the "bottom" of the filter wall aperture, that is defined by the first film), and typically on the entire upper surface of the first sacrificial film. This subsequent deposition of sacrificial material may still be viewed as being part of the first sacrificial film. In any case, a second film is formed on the first sacrificial film and extends within the filter wall aperture to define a filter wall that extends toward, but not to (because of the sacrificial material that was previously deposited in the filter wall aperture), the first film. A second flow port aperture is formed down through the entire vertical extent of the second film. Once the first sacrificial layer is removed, the gap between the filter wall and the first film defines a filter trap.

Various refinements exist of the features noted in relation to the fifth aspect of the present invention. Further features may also be incorporated in the fifth aspect of the present invention as well. These refinements and additional features may exist individually or in any combination. One benefit of this fifth aspect is the accuracy with which the sacrificial material may be deposited in the filter wall aperture, more specifically the thickness of this sacrificial material. As such, the size of the filter trap gap(s) may be precisely controlled. In one embodiment, the thickness of the sacrificial material deposited in the filter wall aperture varies by no more than about 2% from the target thickness.

Although any fabrication technique may be used in relation to the fifth aspect, surface micromachining is preferred. Typically the first film will be separated from the substrate by an intermediate sacrificial layer. This would allow the MEMS filter module to be separated from the substrate after the MEMS filter module is released (e.g., by etching away sacrificial material). For instance, the MEMS filter module may remain supported above the substrate after any such release by one or more structural interconnections. Any such structural interconnections may be disabled (electrically/thermally and/or mechanically fractured), at which time the MEMS filter module may drop onto the underlying substrate (or any film(s) formed directly on the substrate). Preferably, one or more structures are formed on the substrate about the MEMS filter module to thereafter limit lateral movement of the MEMS filter module relative to the substrate until it is retrieved from the substrate. Another option would be to fabricate the MEMS filter module on a layer of a sacrificial material and not structurally interconnect the MEMS filter module with the underlying substrate. In this case, the removal of the sacrificial material will separate the MEMS filter module from the substrate.

A sixth aspect of the present invention is directed to a method for fabricating a MEMS filter module using a substrate. A first sacrificial film is formed on (directly or indirectly) the substrate, and the MEMS filter module is thereafter fabricated by forming a plurality of sacrificial and structural films. A plurality of structural interconnections are provided between the MEMS filter module and the substrate. The first sacrificial film is removed such that the filter module is suspended above the substrate by the structural interconnections. Each of the structural interconnections is then disabled to allow the MEMS filter module to drop or fall onto the underlying substrate or a film formed directly on the substrate.

Various refinements exist of the features noted in relation to the sixth aspect of the present invention. Further features may also be incorporated in the sixth aspect of the present invention as well. These refinements and additional features may exist individually or in any combination. Any appropriate way of disabling the structural interconnections between the MEMS filter module the substrate may be utilized. In one instance, an electrical signal is applied to each structural interconnection to at least thermally degrade the same. Another option is to apply a mechanical force to the MEMS filter module (e.g., in the direction of the underlying substrate) to mechanically fracture the various structural interconnections. In any case, one or more structures may be formed on the substrate MEMS filter module to limit lateral movement of the MEMS filter module once the substrate after the various structural interconnections have been disabled or terminated.

A seventh aspect of the present invention is directed to an implant for addressing pressure within a first body region. The implant includes a conduit having a flow path, and is adapted to fluidly interconnect with the first body region. A MEMS filter module is disposed within the conduit flow path, and includes a first film and second film that are disposed in spaced relation. The first film includes at least one first flow port (and thereby encompassing including a plurality of such first flow ports), while the second film includes at least one second flow port (and thereby encompassing including a plurality of such second flow ports). The MEMS filter module further includes at least one filter wall that extends from the second film at least toward the first film such that a gap between a particular filter wall and the first film defines a filter trap.

Various refinements exist of the features noted in relation to the seventh aspect of the present invention. Further features may also be incorporated in the seventh aspect of the present invention as well. These refinements and additional features may exist individually or in any combination. Preferably, the first and second films are maintained in an at least substantially fixed position relative to each other for the anticipated flow rates/pressures. Both the first film and the second film used by the MEMS filter module of the seventh aspect may have a maximum thickness of about 10 microns, and more typically within the range of about 1 micron to about 3 microns. Any appropriate material may be used for the first and second films. Although any appropriate microfabrication technique may be used in relation to this MEMS filter module, surface micromachining is a preferred approach, using materials such as polysilicon, silicon carbide, silicon nitride, polysilicon germanium, and tungsten for the first and second films, as well as for each filter wall. Typically the first and second films and each filter wall will all be fabricated from the same material. The MEMS filter module also will typically be separated from any substrate that is used in the fabrication of the MEMS filter module prior to using the same in a filtering application (e.g., prior to disposing the same in a relevant filter housing(s) or other structure for receiving the MEMS filter module).

The first and second films used by the MEMS filter module of the seventh aspect may define its upper and lower boundaries or opposing extremes for the MEMS filter module. The first and/or second films each could also be an "intermediate" film in the MEMS filter module. One embodiment has a lower film that is vertically spaced from the first film on the opposite side thereof in relation to the second film. That is, the first film is located at an intermediate elevation between the second film and the lower film. This lower film may include a plurality of flow ports extending therethrough as well.

Each filter wall used by the MEMS module of the seventh aspect may be of an appropriate configuration. In one embodiment, each filter wall has an annular configuration or a closed perimeter. "Annular" means that a particular filter wall extends a full 360° about a certain point or axis, and does not require this filter wall to be circular. Representative annular configurations for each filter wall include without limitation circular, square, and rectangular. In the case where a particular filter wall is annular, the corresponding filter trap will thereby also be annular. This may be of benefit for maintaining a desired flow rate through the MEMS filter module.

In one embodiment of the seventh aspect, each filter wall extends from the second film and terminates prior to reaching the surface of the first film that faces the surface of the second film. In this case, a filter trap is defined by a distal end of a particular filter wall and the surface of the first film that faces the surface of the second film from which this filter wall extends. At least two first flow ports and at least two second flow ports may be associated with each filter trap. Both the first and second flow ports may be of any appropriate size, shape, and configuration, and further may be disposed in any appropriate arrangement. For instance, multiple first flow ports through the first film may be arranged such that an area encompassed by projecting a filter wall onto the first film does not include any of the first flow ports (e.g., each of the first flow ports may be offset from this filter wall).

A particular filter trap associated with the MEMS filter module of the seventh aspect is defined by a space between the first film and a filter wall that extends from the second film. Preferably, each filter trap is defined by the space between the distal end of its corresponding filter wall and the first film. That is, in this particular instance each filter wall does not extend all the way to the first film. In one embodiment, the height of this gap is no more than about 0.4 microns. Any appropriate gap size may be utilized.

A first annular seal may extend between the first and second films such that the first film, the second film, and the first annular seal collectively define an enclosed space in the case of the seventh aspect. The region bounded by this first annular seal may be characterized as a filtering region. All of the filter walls, filter traps, first flow ports, and second flow ports may be located in this filtering region. A plurality of posts or other appropriate supports may extend between and interconnect the first and second films in the filtering region as well.

More than one annular seal may be provided between the first and second films in the case of the seventh aspect. For instance, a second annular seal may be spaced outwardly from the first annular seal, and may extend between and interconnect the first and second films as well. A third annular seal may be spaced outwardly from the second annular seal, and may extend between and interconnect the first and second films as well. Using multiple, radially spaced, annular seals reduces the potential for undesirable leakage out of the filtering region. In one embodiment, the width of a perimeter region having at least one annular seal is at least about 3 microns to about 4 microns, and may be on the order of about 20 microns to about 25 microns.

A plurality of posts or other supports may extend between and interconnect the first and second films in accordance with the seventh aspect. These posts or supports may be of any appropriate size, shape, and/or configuration. The various posts may be distributed throughout the above-noted filtering region. A plurality of filter walls may also be utilized within the filtering region. In one embodiment, the number of supports is no less than the number of filter walls. Stated another way, there are at least as many supports as there are filter walls. In the case where the filter walls are annular, each such filter wall may surround or be disposed about at least one of the supports. That is, at least one support may be disposed inwardly of each annular filter wall. The "density" of the above-noted supports that may interconnect the first and second films throughout the filtering region may be selected to provide a desired degree of rigidity in relation to the anticipated flow rate(s) through the MEMS filter module (e.g., to reduce the amount that the second film deflects relative to the first film, which could change the size of one or more filter traps), may be selected to precisely maintain the magnitude of each filter trap throughout the filtering region for the anticipated flow rate(s) through the MEMS filter module, or both. In one embodiment, the maximum spacing between adjacent pairs of supports in the filtering region is no more than 100 microns, and may be on the order of 5 microns to about 20 microns.

Multiple filter trap chambers may be associated with each filter trap utilized by the MEMS filter module of the seventh aspect. Each such filter trap chamber may be defined by the space between the first and second films. A first filter trap chamber may be the space "bounded" by an annular filter wall, and a second filter trap chamber may be located beyond the outer perimeter of such an annular filter wall. The volume of each first filter trap chamber and the volume of each second filter trap chamber may be larger than the volume of any first flow port or any second flow port, although such need not be the case. In any case, the flow path through the MEMS filter module will either be into a first filter trap chamber, through the associated filter trap, and then into the second filter trap chamber, or vice versa.

The conduit used by the seventh aspect may be of any appropriate configuration for the particular implant application, and the implant may be used for any appropriate application. Any way of integrating the MEMS filter module with the conduit may be used, such as by directly disposing the MEMS filter module within the conduit or by using one or more housings. The MEMS filter module may be retained within the conduit flow path in any appropriate manner as well. Any of the MEMS flow modules discussed above in relation to the first through the sixth aspects may be used by this seventh aspect as well.

Any appropriate coating may be applied to various surfaces of the MEMS filter module and/or any housing associated therewith in the case of the seventh aspect, including without limitation a coating that improves biocompatibility, that makes such surfaces more hydrophilic, and/or that reduces the potential for bio-fouling. In one embodiment, a self-assembled monolayer coating (e.g., poly-ethylene-glycol) is applied in any appropriate manner (e.g., liquid or vapor phase, with vapor phase being the preferred technique) to all exposed surfaces of the MEMS filter module and any housing that integrates the MEMS filter module for positioning within the conduit. Coatings of this type may be used in relation to the other aspects of the present invention described herein as well.

As noted, one or more housings may be used to integrate the MEMS filter module with the conduit in the case of the seventh aspect. For instance, the MEMS filter module could be disposed on the end of or within a housing (e.g., in accordance with the outer housing discussed below), that in turn is at least partially disposed within the conduit of the implant. Another option would be for a first inner housing to be at least partially disposed within an outer housing having a first flow path, for the MEMS filter module to be mounted on or disposed adjacent to the first inner housing such that all flow through the first flow path is directed through the MEMS filter module, and for the outer housing to be at least partially disposed within the conduit of the implant. The outer housing and first inner housing may provide structural integrity for the MEMS filter module, and further may protect the MEMS filter module. In this regard, both the outer housing and first inner housing may be rigid structures, or at least may be more rigid than the MEMS filter module. Representative materials from which both the outer housing and the first inner housing may be formed include without limitation polymethylmethacrylate (PMMA), ceramics, silicon, titanium, and other implantable metals and plastics.

Both the outer housing and the first inner housing may be of any appropriate shape (e.g., a cylinder). Typically the outer housing will be adapted in some manner for disposition. at least partially within the conduit, while the first inner housing will be adapted in some manner for disposition at least partially within the outer housing. For instance, the outer housing may be disposed about the first inner housing along the entire length of the first inner housing (e.g., each end of the first inner housing may be flush with or recessed inwardly from the corresponding end of the outer housing), or only along a portion of the length of the first inner housing (e.g., one or both ends of the first inner housing may extend beyond the corresponding end of the outer housing).

The first inner housing is preferably maintained in a stationary or fixed position relative to the outer housing in the case of the seventh aspect. For instance, the first inner housing may be bonded to the outer housing, a press fit may be utilized between the outer housing and first inner housing, the outer housing may be shrink-fitted about the first inner housing, or any combination thereof. A second inner housing may also be at least partially disposed within the outer housing, with the MEMS filter module being located between adjacent ends of the first inner housing and second inner housing, and preferably mounted to at least one of the first inner housing and second inner housing. Such a second inner housing is also preferably maintained in a stationary or fixed position relation to the outer housing in the same manner as the first inner housing.

Additional characterizations may be may be made in relation to incorporating the MEMS filter module using an outer housing and first inner housing in the case of the seventh aspect. The MEMS filter module may be recessed within the first inner housing. Consider the case where the first inner housing includes first and second ends, and where the first flow path extends between these first and second ends. The MEMS filter module may be located anywhere between these first and second ends. Another option would be for the MEMS filter module to be mounted on the first or second end of the first inner housing.

Any appropriate way of mounting the MEMS filter module to the first inner housing may be used in the case of the seventh aspect. For instance, the MEMS filter module may be bonded to the first inner housing, there may be a press fit between the MEMS filter module and the first inner housing, or both. In any case, preferably the MEMS filter module is maintained in a fixed position relative to the first inner housing.

Surface micromachining is the preferred technology for fabricating the MEMS filter modules described herein. In this regard, these MEMS filter modules may be fabricated in at least two different fabrication levels that are spaced from each other (hereafter a first fabrication level and a second fabrication level). "Fabrication level" corresponds with what may be formed by a deposition of a structural material before having to form any overlying layer of a sacrificial material (e.g., from a single deposition of a structural layer or film). The first film may be fabricated at least in the first fabrication level, while the second film may be fabricated in at least the second fabrication level. It should be appreciated that the characterization of the first film being in the "first fabrication level" and the second film being in the "second fabrication level" by no means requires that the first fabrication level be that which is deposited "first", and that the second fabrication level be that which is deposited "second." Moreover, it does not require that the first fabrication level and the second fabrication level be immediately adjacent to each other. These MEMS filter modules may be fabricated on an appropriate substrate and where the first film is fabricated in one structural layer that is disposed somewhere between the substrate and another structural layer in which the second film is fabricated, or vice versa.

The first and second films each may exist in a single fabrication level or may exist in multiple fabrication levels. In the above-noted first instance, a deposition of a structural material in a single fabrication level may define an at least generally planar layer. Another option regarding the first instance would be for the deposition of a structural material in a single fabrication level to define an at least generally planar portion, plus one or more structures that extend down toward, but not to, the underlying structural layer at the underlying fabrication level. As such, the second film and each filter wall may exist in a common fabrication level.

In the above-noted second instance, two or more structural layers or films from adjacent fabrication levels could be disposed in direct interfacing relation (e.g., one directly on the other). This would require removal of the sacrificial material that is deposited on the structural material at one fabrication level before depositing the structural material at the next fabrication level. Another option regarding the above-noted second instance would be to maintain the separation between structural layers or films in different fabrication levels, but provide an appropriate structural interconnection therebetween (e.g., a plurality of columns, posts, or the like extending between adjacent structural layers or films in different, spaced fabrication levels).

The above-described MEMS filter modules are preferably passive devices (no external electrical signal of any type required) and may be used for any appropriate application. Another characterization of these MEMS filter modules is that they are autonomous in that they are self-contained structures and require no external power. For instance, any of these MEMS filter modules may be disposed in a flow path of any type (e.g., between a pair of sources of any appropriate type, such as a man-made reservoir, a biological reservoir, and/or the environment), and further may be used for any appropriate application. That is, one or more of any of these MEMS filter modules could be disposed in a conduit that fluidly interconnects multiple sources (e.g., two or more), and each source may be either a man-made reservoir, a biological reservoir, the environment, or any other appropriate source. One example would be to dispose one or more of these MEMS filter modules in a conduit extending between the anterior chamber of an eye and a location that is exterior of the cornea of the eye. Another example would be to dispose one or more of these MEMS filter modules in a conduit extending between the anterior chamber of an eye and another location that is exterior of the sclera of the eye. Yet another example would be to dispose one or more of these MEMS filter modules in a conduit extending between the anterior chamber of an eye and another location within the eye (e.g., into Schlemm's canal) or body. In any case, any of these MEMS filter modules could be disposed directly into such a conduit, or one or more housings could be used to integrate any of these MEMS filter modules with the conduit. Moreover, in each of the above-noted examples, the conduit may provide an exit path for aqueous humor when installed for a glaucoma patient. That is, each of these examples may be viewed as a way of treating glaucoma or providing at least some degree of control of intraocular pressure.

An eighth aspect of the present invention is embodied by an implant for addressing pressure within a first body region.

The implant includes a conduit having a flow path, and is adapted to fluidly interconnect with the first body region. A MEMS filter module is disposed within the conduit flow path. A first structure exists in a first fabrication level of the MEMS filter module, and a second structure exists in a second fabrication level of the MEMS filter module that is separate or different from the first fabrication level. A first space exists between the first and second structures and defines at least one filter trap for the MEMS filter module. The first and second structures are maintained in an at least substantially fixed position relative to each other for the anticipated flow rates/pressures. At least part of a flow through the MEMS filter module is directed through this first space.

Various refinements exist of the features noted in relation to the eighth aspect of the present invention. Further features may also be incorporated in the eighth aspect of the present invention as well. These refinements and additional features may exist individually or in any combination. For instance, the first structure may be in the form of the first film from the seventh aspect, while the second structure may be in the form of the second film and filter wall(s) from the seventh aspect. Each of the corresponding features that were discussed above in relation to the seventh aspect may be used by this eighth aspect as well. In one embodiment, the first body region is an anterior chamber of an eye, such that the eighth aspect may be used to treat glaucoma or to otherwise control intraocular pressure in at least some respect.

BRIEF DESCRIPTION OF THE SEVERAL VIEWS OF THE DRAWING

FIG. 1 is a side view schematic of one embodiment of a filter that uses a MEMS filter module.

FIG. 2A is a top view of the MEMS filter module used by the filter of FIG. 1, illustrating its filtering and perimeter regions.

FIG. 2B is a cutaway, side view of one embodiment of an upper film for the MEMS filter module of FIG. 2A, where this upper film includes a plurality of flow ports for accommodating a flow into/out of the MEMS filter module.

FIG. 2C is a cutaway, side view of one embodiment of a lower film for the MEMS filter module of FIG. 2A, where this lower film includes a plurality of flow ports for accommodating a flow into/out of the MEMS filter module.

FIG. 2D is a cutaway side view of one embodiment of a filter trap that may be used in the filtering region of the MEMS filter module of FIG. 2A.

FIG. 2E is a bottom, plan view of one embodiment of a filter wall that may be used by the filter trap of FIG. 2D.

FIG. 2F is a cross-sectional view taken along line E-E of the MEMS filter module of FIG. 2A, illustrating one embodiment of the perimeter region for the MEMS filter module.

FIG. 5D is a perspective, bottom view of part of the upper film of the filtering region configuration of FIG. 5A, illustrating the filter walls and supports extending therefrom.

FIG. 9C is a perspective view of part of the second film sections positioned on the lower supports illustrated in FIG. 9B.

DETAILED DESCRIPTION OF THE INVENTION

Figure 3A:
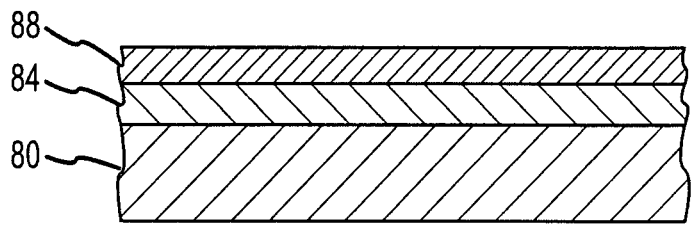
FIGS. 3A-I illustrate one fabrication technique for defining a filter trap from a first film and a filter wall that extends from a second film that is spaced from the first film.

The present invention will now be described in relation to the accompanying drawings that at least assist in illustrating its various pertinent features. FIG. 1 illustrates one embodiment of a filter 10 that utilizes a MEMS filter module 34 formed from a plurality of spaced plates or films maintained in fixed relation to each other. These "films" will typically have a thickness or vertical extent of no more than about 10 microns, and more typically a thickness within a range of about 1 micron to about 3 microns. In any case, the MEMS filter module 34 is preferably removably disposed in a filter housing 14, and separates the housing 14 into an upper chamber 26 and a lower chamber 30. At least one upper flow port 18 extends through the filter housing 14 at a location so as to fluidly communicate with the upper chamber 26. Similarly, at least one lower flow port 22 extends through the filter housing 14 at a location so as to fluidly communicate with the lower chamber 30. The flow may be directed through the filter housing 14 in any direction, as indicated by the arrows in FIG. 1.

The filter housing 14 may be of any appropriate configuration, may be formed from any appropriate material, may be used for any appropriate application, and may receive/ engage the MEMS filter module 34 in any appropriate manner (preferably such that all flow through the filter 10 is required to be directed through the MEMS filter module 34). Any number of flow ports 18, 22 may be associated with the upper chamber 26 and lower chamber 30, respectively, and these flow ports 18, 22 may be of any appropriate size and/or shape. The upper chamber 26 and lower chamber 30 each may be of any appropriate size and/or configuration as well, so long as the upper chamber 26 and lower chamber 30 of the filter 10 provide an appropriate flow path to/from the MEMS filter module 34.

The filter 10 may be used for any appropriate application. The "flow" through the filter 10 may be of any appropriate type (e.g. continuous, intermittent) and may be of any appropriate fluid. At least some type of force will typically be exerted on a fluid to provide the flow through the filter 10. This force may be from any appropriate source, such as a pressure source (e.g., a pump), gravity, or a combination thereof. In any case, the filter 10 attempts to remove at least something from the fluid. The filter 10 could be used such that the fluid output from the filter 10 is used for some desired purpose, such that the material retained within the filter 10 is used for some desired purpose, or a combination thereof.

Certain details regarding the MEMS filter module 34 are illustrated in FIGS. 2A-F. There are two prime areas or regions of the MEMS filter module 34, namely a filtering region 38 and a perimeter region 42. At least two spaced films or plates are used by the MEMS filter module 34 in both the filtering region 38 and the perimeter region 42. As will be discussed in more detail below, microfabrication techniques are preferably utilized to fabricate the MEMS filter module 34 on an appropriate substrate (e.g., a wafer). Notably in this regard, the MEMS filter module 34 is separated from the substrate prior to installation in the filter housing 14.

The MEMS filter module 34 includes a first plate or film 70 and a second plate or film 46 that are disposed in spaced relation or at different elevations in the MEMS filter module 34. Preferably, these films 70, 46 are maintained in an at least substantially fixed position relative to each other for the anticipated flow rates/pressures. Each of these films 70, 46 may define an extreme of the MEMS filter module 34 (e.g., may define the lower or upper extent of the MEMS filter module 34) or may be disposed at an intermediate location within the MEMS filter module 34 (e.g., "sandwiched" between two spaced films, and disposed in spaced relation to each of these films). That is, the first film 70 could be a lower extreme of the MEMS filter module 34 or could be at an intermediate location between the upper and lower extremes of the MEMS filter module 34. Similarly, the second film 46 could be an upper extreme of the MEMS filter module 34 or could be at an intermediate location between the upper and lower extremes of the MEMS filter module 34. In any case, the first film 70 includes a plurality of first flow ports 74, while the second film 46 includes a plurality of second flow ports 50. All of the first flow ports 74 and all of the second flow ports 50 are located in the filtering region 38 of the MEMS filter module 34 (i.e., not in the perimeter region 42).

At least one support 78 (e.g., a post or column) extends between and structurally interconnects the first film 70 and the second film 46 in the filtering region 38 of the MEMS filter module 34. Preferably a plurality of such supports 78 are distributed throughout the filtering region 38 in a repeating pattern and in spaced relation to each other. The supports 78 in the filtering region 38 may be of any appropriate size and/or configuration. At least one filter wall 54 is attached to and extends from the second film 46 and at least toward (in the direction of) the first film 74. Each such filter wall 54 terminates prior to reaching the primary surface of the first film 70 that faces the second film 46. Stated another way, each filter wall 54 is shorter than the gap between the first film 70 and the second film 46. In addition, each filter wall 54 is offset from each of the plurality of first flow ports 74. That is, an area defined by projecting the various filter walls 54 onto the primary surface of the first film 70 that faces the second film 46 does not encompass any of the first flow ports 74. Preferably, each filter wall 54 is maintained in an at least substantially fixed position relative to the first film 70 for the anticipated flow rates/pressures.

Any number of filter walls 54 may be utilized in the filtering region 38. Although any number of supports 78 may be utilized in the filtering region 38 as well, the number and location of the supports 78 is subject to a number of characterizations for the filtering region 38. One is that each filter wall 54 preferably has at least one support 78 associated therewith. Another is that there are at least as many supports 78 as there are filter walls 54. Another is that the maximum spacing between each pair of adjacent supports 78 is no more than about 100 microns in one embodiment, and more typically within a range of about 5 microns to about 20 microns in another embodiment.

Each filter wall 54 of the MEMS filter module 34 preferably has an annular configuration. "Annular" in this context means that the filter wall 54 has a closed perimeter when looking at the distal end of the filter wall 54 (that which is opposite the end of the filter wall 54 that interfaces with the second film 46). Stated another way, each filter wall 54 extends a full 360 degrees about a certain reference axis along any appropriate path. Any configuration may be utilized to realize the desired annular extent for the filter wall 54 (e.g., circular, oval, square, rectangular). Each filter wall 54 also does not extend all the way to the first film 70 as noted. Instead, a filter trap or a filter trap gap 58 exists between the distal end of each filter wall 54 and the first film 70. Since each filter wall 54 is annular in the preferred configuration, each filter trap gap 58 will similarly be annular. Therefore, any constituent that is "trapped" by being unable to pass through a particular filter trap gap 58 will then not totally "plug" this filter trap gap 58. Having an annular filter trap gap 58 associated with each filter wall 54 also provides a desired flow rate through the MEMS filter module 34.

The flow may enter the MEMS filter module 34 either through the second flow ports 50 (in which case the flow out of the MEMS filter module 34 would be through the first flow ports 74), or through the first flow ports 74 (in which case the flow out of the MEMS filter module 34 would be through the second flow ports 50). In either case, the flow will be directed into a space 62 that extends from the first film 70 to the second film 46 before attempting to pass through a filter trap gap 58 associated with a particular filter wall 54. Each of these spaces 62 in the filtering region 38 may be characterized as a filter trap chamber 62. The height of each filter trap chamber 62 corresponds with the spacing between the first film 70 and the second film 46, which is greater than the height of the filter trap gap 58. The volume of each filter trap chamber 62 may be larger than the volume of any associated first flow port 70, and further may be larger than the volume of any associated second flow port 50, although such is not a requirement. Whether the flow enters the MEMS filter module 34 through the first flow ports 74 or the second flow ports 50, the flow will go through a filter trap chamber 62, then through a filter trap gap 58, and then through another filter trap chamber 62. Although each filter trap chamber 62 could be of the same configuration and volume, in one embodiment there are two distinct groups of filter trap chambers 62 that differ from each other in at least some respect (e.g., different volumes/configurations).

As noted above, the flow may be directed through the filter 10 in any direction. One or more first flow ports 74 may be disposed inwardly of each filter wall 54 (so as to fluidly interconnect with a filter trap chamber 62 bounded by a single filter wall 54), while one or more second flow ports 50 may be disposed beyond the perimeter of each filter wall 54 (so as to fluidly interconnect with a filter trap chamber 62 defined by the spacing between multiple filter walls 54) (FIG. 2E). Conversely, one or more second flow ports 50 may be disposed inwardly of each filter wall 54 (so as to fluidly interconnect with a filter trap chamber 62 bounded by a single filter wall 54), while one or more first flow ports 74 may be disposed beyond the perimeter of the filter wall 54 (so as to fluidly interconnect with a filter trap chamber 62 defined by the spacing between multiple filter walls 54) (FIG. 2E). In any case, flow is required to pass through a filter trap gap 58 defined in part by the filter wall 54 before exiting MEMS filter module 34.

There are a number of characterizations relating to the flow through the MEMS filter module 34. One is that the flow through the MEMS filter module 34 is not axial in that it must undergo at least one change in direction, including without limitation to flow through a filter trap gap 58. Another characterization is that the direction of the flow through the filter trap gap 58 is in a dimension that is at least generally parallel with the first film 70 and second film 46. Another characterization is that the flow through the filter trap gap 58 is at least generally orthogonal to the direction of the flow through both the first film 70 and second film 46.

Flow is directed through the filter trap gap 58 to provide a filtering function. Any constituent in the flow (e.g., particulates, cells of at least a certain size) that is larger than the height of the filter trap gap 58 will typically be collectively retained by the filter wall 54 and the first film 70 (i.e., by being unable to pass through the filter gap 58). The number and location of the various supports 78 is preferably selected such that the height of each filter trap gap 58 throughout the filtering region 38 is maintained within a small tolerance for the maximum flow rates for which the MEMS filter module 34 is designed. In the case where the height of each filter trap gap 58 is about 0.4 microns or less, supports 78 are distributed throughout the filtering region 38 such that the height of each such filter trap gap 58 will vary by no more than about a few tens of nanometers (e.g., due to a deflection of the first film 70 and/or second film 46) when running the maximum flow rate through the filter 10 for which it was designed.

One or more annular seals 66 are located in the perimeter region 42 of the MEMS filter module 34, and define a boundary or perimeter for the filtering region 38 of the MEMS filter module 34. "Annular" in the context of the annular seal(s) 66 means that the annular seal(s) 66 defines a closed perimeter or boundary for the filtering region 38 of the MEMS filter module 34 in the "lateral" dimension. Stated another way, each seal 66 extends a full 360 degrees about a certain axis. In any case, all first flow ports 74 associated with the first film 70 and all second flow ports 50 associated with the second film 46 are thereby disposed inwardly of each annular seal 60. Any number of annular seals 66 may be utilized (three in the illustrated embodiment), and are preferably concentrically disposed in laterally spaced relation to provide redundant sealing capabilities for the filtering region 38 of the MEMS filter module 34 in the lateral dimension. That is, the annular seals 66 at least attempt to force all of the flow through the filtering region 38 of the MEMS filter module 34. Each of the annular seals 66 may be of the same width, or at least one of the annular seals 66 may be of a different width. In one embodiment, the annular seal 66 that is most outwardly disposed is wider than any other annular seal 66.

Another function of each annular seal 66 used by the MEMS filter module 34 is to provide structural strength or rigidity for the MEMS filter module 34. Each annular seal 66 structurally interconnects the first film 70 with the second film 46 in the perimeter region 42 of the MEMS filter module 34. This may be used for handling/engaging the MEMS filter module 34 in a manner that reduces the potential for damaging the physical structure of the MEMS filter module 34. The perimeter region 42 of the MEMS filter module 34 is preferably more rigid than the filtering region 38 of the MEMS filter module 34. The perimeter region 42 may thereby provide a desired, sufficiently robust interface for engagement with the filter housing 14 or an intermediate sealing structure. The width of the perimeter region 42 is at least about 3 or 4 microns in one embodiment, and may be on the order of about 20 microns to about 25 microns in another embodiment.

Both the first film 70 (having the plurality of first flow ports 74) and the second film 46 (having the plurality of second flow ports 50) are thereby supported about their respective perimeter regions by each annular seal 66. That is, both the first film 70 (having the plurality of first flow ports 74) and the second film 46 (having the plurality of second flow ports 50) are continuous structures throughout the MEMS filter module 34. Stated another way, one may progress along the first film 70 from one location in the perimeter region 42 of the MEMS filter module 34, through the filtering region 38, and to any other location in the perimeter region 42 along a continuous path defined by the first film 70 (albeit possibly along a meandering path). Similarly, one may progress along the second film 46 from one location in the perimeter region 42 of the MEMS filter module 34, through the filtering region 38, and to any other location in the perimeter region 42 along a continuous path defined by the second film 46 (albeit possibly along a meandering path).

The MEMS filter module 34 may be defined by any number of films, may be formed from any appropriate material, may be of any appropriate configuration for the desired application, and may be of any appropriate shape in plan view (FIG. 2A). Preferably, the first film 70, the second film 46, the filter wall(s) 54, the support post(s) 78, and the annular seal(s) 66 are formed from the same material (e.g., polysilicon) for purposes of fabrication by surface micromachining as will be discussed in more detail below in relation to FIGS. 3A-I. The filter wall 54 may be of any configuration that defines an annular extent for the preferred embodiment, including without limitation circular, oval, triangular, square, or rectangular. Similarly, each annular seal 66 may be of any configuration that defines an annular extent, including without limitation circular, oval, triangular, square, or rectangular.

Any number of first flow ports 74 and any number of second flow ports 50 may be utilized, although preferably a plurality of first flow ports 74 and a plurality of second flow ports 50 are able to provide a flow through any particular filter trap gap 58. That is, at least two first flow ports 74 and at least two second flow ports 50 are preferably associated with each filter wall 54. Therefore, any "plugging" of an individual first flow port 74 or second flow port 50 should not totally disable any one filter trap gap 58. Another option would be to size/configure the first flow ports 74 and second flow ports 50 such that the potential for a single particle or constituent being able to totally block the same is reduced. In any case, both the first flow ports 74 and the second flow ports 50 may be of any appropriate size and/or configuration, including without limitation to accommodate the desired number/arrangement of supports 78 extending between the first film 70 and second film 46 and the desired flow through the MEMS filter module 34. Preferably, a repeating pattern is used throughout the filtering region 38 of the MEMS filter module 34 for the first flow ports 74, the second flow ports 50, the filter walls 54, and the supports 78.

The preferred fabrication technique for the various filter modules described herein is surface micromachining. Surface micromachining generally entails depositing alternate layers of structural material and sacrificial material using an appropriate substrate (e.g., a silicon wafer) which functions as the foundation for the resulting microstructure. Various patterning operations (collectively including masking, etching, and mask removal operations) may be executed on one or more of these layers before the next layer is deposited so as to define the desired microstructure. After the microstructure has been defined in this general manner, all or a portion of the various sacrificial layers are removed by exposing the microstructure and the various sacrificial layers to one or more etchants. This is commonly called "releasing" the microstructure from the substrate, typically to allow at least some degree of relative movement between the microstructure and the substrate. One particularly desirable surface micromachining technique is described in U.S. Pat. No. 6,082,208, that issued Jul. 4, 2000, that is entitled "Method For Fabricating Five-Level Microelectromechanical Structures and Microelectromechanical Transmission Formed," and the entire disclosure of which is incorporated by reference in its entirety herein (hereafter the '208 Patent).

The term "sacrificial layer or film" as used herein means any layer or portion thereof of any surface micromachined microstructure that is used to fabricate the microstructure, but which does not generally exist in the final configuration (e.g., sacrificial material may be encased by a structural material at one or more locations for one or more purposes, and as a result this encased material is not removed by the release). Exemplary materials for the sacrificial layers described herein include undoped silicon dioxide or silicon oxide, and doped silicon dioxide or silicon oxide ("doped" indicating that additional elemental materials are added to the film during or after deposition). The term "structural layer or film" as used herein means any other layer or portion thereof of a surface micromachined microstructure other than a sacrificial layer and a substrate on which the microstructure is being fabricated. Exemplary materials for the structural layers described herein include doped or undoped polysilicon and doped or undoped silicon. Exemplary materials for the substrates described herein include silicon. The various layers described herein may be formed/deposited by techniques such as chemical vapor deposition (CVD) and including low-pressure CVD (LPCVD), atmospheric-pressure CVD (APCVD), and plasma-enhanced CVD (PECVD), thermal oxidation processes, and physical vapor deposition (PVD) and including evaporative PVD and sputtering PVD, as examples.

In more general terms, surface micromachining can be done with any suitable system of a substrate, sacrificial film(s) or layer(s) and structural film(s) or layer(s). Many substrate materials may be used in surface micromachining operations, although the tendency is to use silicon wafers because of their ubiquitous presence and availability. The substrate is essentially a foundation on which the microstructures are fabricated. This foundation material must be stable to the processes that are being used to define the microstructure(s) and cannot adversely affect the processing of the sacrificial/structural films that are being used to define the microstructure(s). With regard to the sacrificial and structural films, the primary differentiating factor is a selectivity difference between the sacrificial and structural films to the desired/required release etchant(s). This selectivity ratio may be on the order of about 10:1, and is more preferably several hundred to one or much greater, with an infinite selectivity ratio being most preferred. Examples of such a sacrificial film/structural film system include: various silicon oxides/various forms of silicon; poly germanium/ poly germanium-silicon; various polymeric films/various metal films (e.g., photoresist/aluminum); various metals/ various metals (e.g., aluminum/nickel); polysilicon/silicon carbide; silicone dioxide/polysilicon (i.e., using a different release etchant like potassium hydroxide, for example). Examples of release etchants for silicon dioxide and silicon oxide sacrificial materials are typically hydrofluoric (HF) acid based (e.g., concentrated HF acid, which is actually 49 wt % HF acid and 51 wt % water; concentrated HF acid with water; buffered HF acid (HF acid and ammonium fluoride)).

Figure 3B:
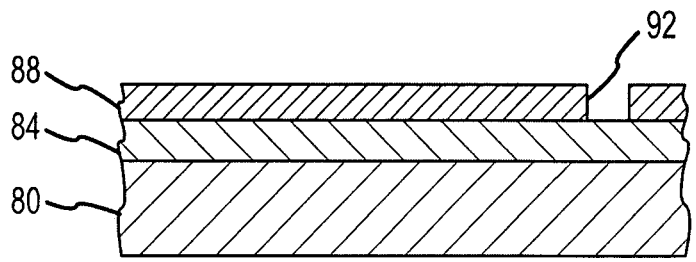

FIG. 3A illustrates a first sacrificial film 84 (commonly referred to as the SacOx1 layer or level in the process described in the '208 Patent) having been formed over the substrate 80. Although the first sacrificial film 84 could be formed directly on the substrate 80, typically there will be one or more intermediate layers or films (not shown, but commonly referred to as the P0 layer or level in the process described in the '208 Patent from which electrical traces or the like are formed, which in turn is separated from the substrate material by an oxide or nitride film or layer). In any case, a first film 88 (commonly referred to as the combined P2/P1 layers or fabrication levels in the process described in the '208 Patent) is formed on the first sacrificial film 84. The first film 88 is then patterned to define a first flow port aperture 92 as illustrated in FIG. 3B. This first flow port aperture 92 will become a first flow port 120 for the first film 88 when the MEMS filter module is released at the end of fabrication (FIG. 3I).

Figure 3C:
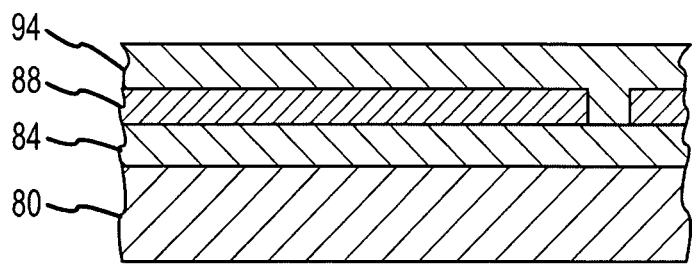
Figure 3D:
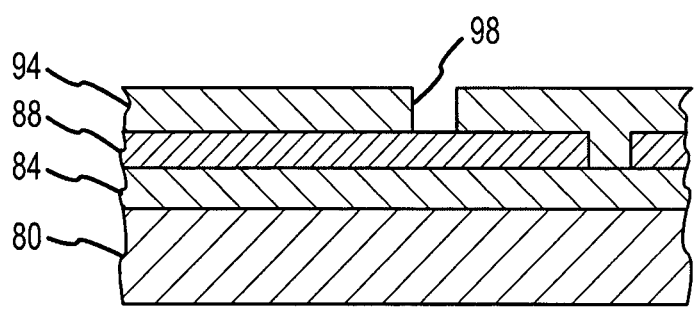

A second sacrificial film 94 (commonly referred to as the SacOx3 layer or level in the process described in the '208 Patent) is then formed on the first film 88 (FIG. 3C). This second sacrificial film 94 will extend within and typically at least substantially "fill" the first flow port aperture 92 in the first film 88. The second sacrificial film 94 is then patterned to define a filter wall aperture 98 (FIG. 3D). This filter wall aperture 98 extends all the way down to the first film 88. Typically, the second sacrificial film 94 will be over-etched, such that a small portion of the upper surface of the first film 88 will be etched by the formation of the filter wall aperture 98 as well. That is, there may be a small depression on the upper surface of the first film 88 corresponding with the filter wall aperture 98 in the second sacrificial film 94 after the patterning of the second sacrificial film 94 to define the filter wall aperture 98 (not shown).

Figure 3E:
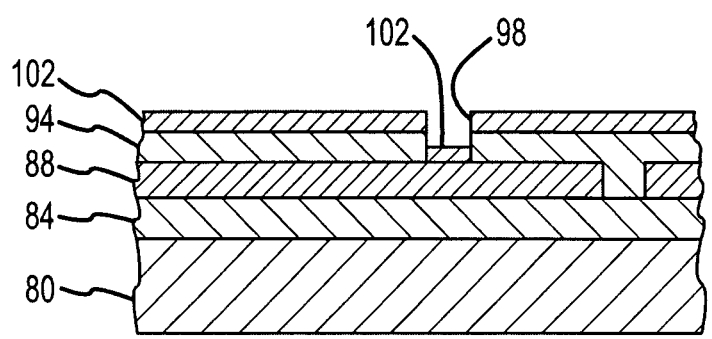

FIG. 3E illustrates that additional sacrificial material 102 is formed on the upper surface of the second sacrificial film 94. Although the sacrificial material 102 in the second sacrificial film 94 are shown as separate structures in FIGS. 3E-H, this additional sacrificial material 102 is in effect almost indistinguishable from and becomes part of the second sacrificial film 94. The sacrificial material 102 is also deposited on the surface of the first film 88 that is exposed by the filter wall aperture 98 in the second sacrificial film 94. It is possible that a certain amount of the sacrificial material 102 will also be deposited on the sidewall of the filter wall aperture 98 in the second sacrificial film 94 (not shown). The thickness of the sacrificial material 102 can be very accurately controlled and is used to define the thickness of a filter trap gap 123 in the resulting MEMS filter module (FIG. 3I). For instance, it is possible to deposit the sacrificial material 102 within a tolerance of +/−2% of the target thickness.

Figure 3F:
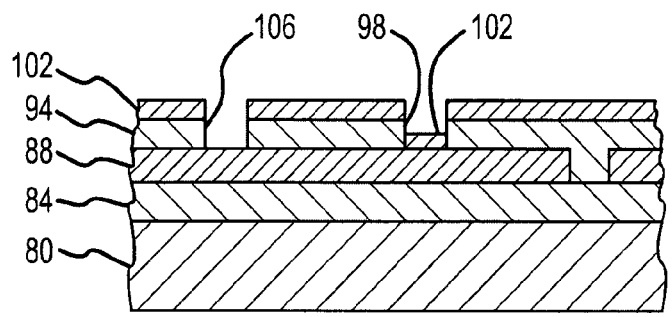
Figure 3G:
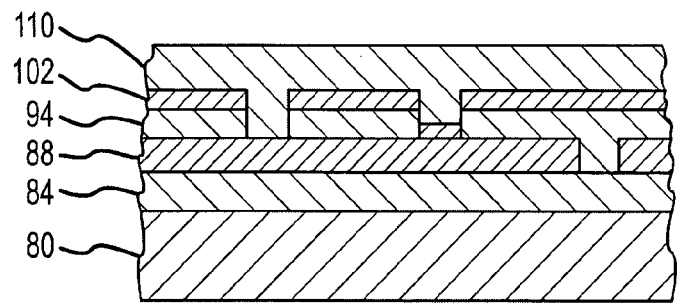

The film of sacrificial material 102 is then patterned to define a support post aperture 106 that exposes a corresponding portion of the upper surface of the first film 88 (FIG. 3F). That is, the support post aperture 106 extends completely through the layer of sacrificial material 102 and through the second sacrificial film 94 to the underlying first film 88. A second film 110 is then formed on the upper surface of the layer of sacrificial material 102 as illustrated in FIG. 3G at a different fabrication level than the first film 88. This second film 110 will extend within and typically at least substantially "fill": 1) the support post aperture 106 in the layer of sacrificial material 102 and the second sacrificial film 94 so as to define a support 118 for the MEMS filter module; and 2) the filter wall aperture 98 in the layer of sacrificial material 102 and the second sacrificial film 94 so as to define a filter wall 121 for the MEMS filter module (FIG. 3I). The distal end of the filter wall 121 (FIG. 3I) is spaced from the first film 88 by the corresponding portion of sacrificial material 102 (FIG. 3G). This sacrificial material 102 is removed by the release of the filter module so as to define a filter trap or filter trap gap 123 (FIG. 3I).

Figure 3H:
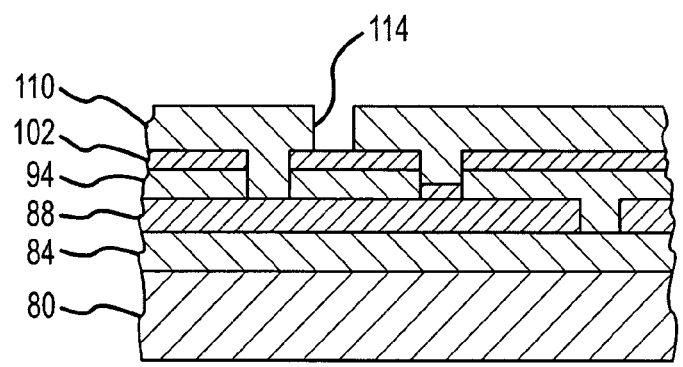
Figure 3I:
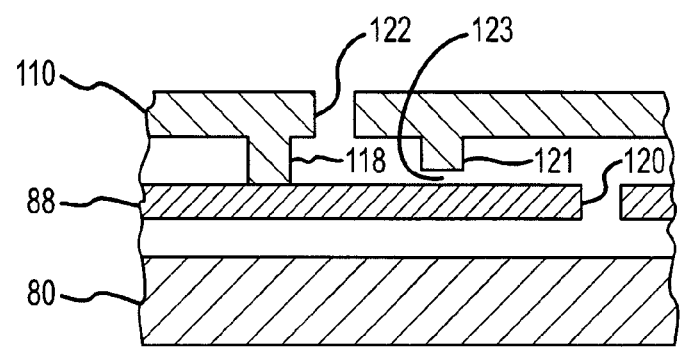

The second film 110 is then patterned to define a second flow port aperture 114 as illustrated in FIG. 3H. This second flow port aperture 114 will become a second flow port 122 for the second film 110 when the MEMS filter module is released at the end of fabrication. In this regard and referring to FIG. 3I, the "stack" is then exposed to an appropriate etchant that removes the first sacrificial film 84, the second sacrificial film 94, and the sacrificial material 102. The MEMS filter module may remain structurally supported above the substrate 80 after the release (not shown) as will be discussed in more detail below. The MEMS filter module is, however, ultimately separated from the substrate 80 for incorporation into the filter 10 as will be discussed in more detail below in relation to FIGS. 10A-11B.

Various embodiments of MEMS filter modules are illustrated in FIGS. 4A-8D that are in accordance with the principles of the MEMS filter module 34 of FIGS. 2A-F. Unless otherwise noted herein, the discussion of the MEMS filter module 34 is equally applicable to each of these MEMS filter modules. Reference should be made to the discussion presented above with regard to components of the MEMS filter module 34 that are used by these MEMS filter modules. Moreover, each of these MEMS filter modules may be used in place of the MEMS filter module 34 in the filter 10 of FIG. 1. In each of these cases, the films or plates that cooperate to provide a filtering function are maintained in an at least substantially fixed position relative to each other for the anticipated flow rates/pressures. Moreover, each filter wall and the film or plate that cooperate to define a filter trap gap are also maintained in an at least substantially fixed position relative to each other.

FIGS. 4A-F illustrate one embodiment of a MEMS filter module 124 having a filtering region 126. The filter module 124 includes a first film 130 and a second film 138 that are disposed in spaced relation or at different elevations. Each of these films 130, 138 defines an extreme for the filter module 124 in both the filtering region 126 and in its perimeter region 42 (not shown, but in accordance with the embodiment of FIGS. 2A-F). As such, the films 130, 138 are interconnected and supported about their respective perimeter regions by each annular seal 66 used by the filter module 124. The films 130, 138 are thereby "continuous" structures in the same manner discussed above in relation to the films 70, 46.

The first film 130 includes a plurality of first flow ports 134, while the second film 138 includes a plurality of second flow ports 142. All of the first flow ports 134 and all of the second flow ports 142 are located only in the filtering region 126 of the filter module 124. A plurality of supports 154 extend between and structurally interconnect the first film 130 and the second film 138 in the filtering region 126. These supports 154 are distributed throughout the filtering region 126 in a repeating pattern, are disposed in spaced relation to each other, and may be of any appropriate configuration. A plurality of filter walls 150 are attached to and extend from the second film 138 and at least toward (in the direction of) the first film 130. Any number of filter walls 150 may be utilized in the filtering region 126 of the filter module 124. Although any number of supports 154 may be utilized as well, the number and location of the supports 154 is subject to the same characterizations discussed above in relation to the supports 78. In addition and for the case of the filtering region 126 of the filter module 124, one support 154 is positioned inwardly of each filter wall 150 in a central location, and a plurality of supports 154 are disposed about each filter wall 150. Any number of supports 154 may be disposed about each filter wall 150 (four in the illustrated embodiment, with one support 154 being centrally disposed between the corners of each 2×2 grouping of four adjacent filter walls 150).

Each filter wall 150 has an annular configuration. "Annular" in this context means that each filter wall 150 has a closed perimeter when looking at the distal end of the filter wall 150 (that which is opposite the end of the filter wall 150 that interfaces with the second film 138). Stated another way, each filter wall 150 extends a full 360 degrees about a certain reference axis along any appropriate path. Although each filter wall 150 has a square, annular extent in the illustrated embodiment, any configuration could be utilized for the filter wall 150 to realize the noted annular extent (e.g., rectangular, circular, oval, triangular). Each filter wall 150 also does not extend all the way to the first film 130. Instead, a filter trap or a filter trap gap 152 exists between the distal end of each filter wall 150 and the first film 130. Since each filter wall 150 is annular, its corresponding filter trap gap 152 will likewise be annular. Note that each filter wall 150 is also offset from the various first flow ports 134 and second flow ports 142, thereby inducing at least one change in direction for the flow through the MEMS filter module 124.

Flow may be directed through each filter trap gap 152 to provide a filtering function. Any constituent in the flow (e.g., particulates, cells of a certain size) that is larger than the height of a particular filter trap gap 152 will typically be collectively retained by the corresponding filter wall 150 and the first film 130 (i.e., by being unable to pass through the filter trap gap 152). Since each filter trap gap 152 is annular, any constituent that is "trapped" by being unable to pass through a particular filter trap gap 152 will then not totally "plug" the filter trap gap 152. Having an annular filter trap gap 152 associated with each filter wall 150 also provides a desired flow rate through the MEMS filter module 124. The number and location of the various supports 154 is selected such that the height of each filter trap gap 152 throughout the filtering region 126 is maintained within a small tolerance for the maximum flow rate for which the filter module 124 is designed in the same manner discussed above in relation to the filter trap gap 58.

The flow may enter the MEMS filter module 124 either through the second flow ports 142 (in which case the flow out of the MEMS filter module 124 would be through the first flow ports 134), or through the first flow ports 134 (in which case the flow out of the MEMS filter module 124 would be through the second flow ports 142). In either case, the flow will be directed into a space 148a or a space 148b that extends from the first film 130 to the second film 138 before attempting to pass through a filter trap gap 152 associated with a particular filter wall 150. Each of these spaces 148a, 148b in the filtering region 126 may be characterized as a filter trap chamber 148a, 148b. The height of each filter trap chamber 148a, 148b corresponds with the spacing between the first film 130 and the second film 138, which is greater than the height of the filter trap gap 152. Each annular filter wall 150 defines a filter trap chamber 148a, while the space between the various filter walls 150 defines a single filter trap chamber 148b.

The volume of each filter trap chamber 148a may be larger than the volume of any associated first flow port 134, while the volume of the filter trap chamber 148b may be larger than the volume of any associated second flow port 142, although such is not a requirement. Whether the flow enters the MEMS filter module 124 through the first flow ports 134 or the second flow ports 142, the flow will go through a filter trap chamber 148a or the filter trap chamber 148b, then through a filter trap gap 152, and then through the other of a filter trap chamber 148a or the filter trap chamber 148b in the case of the filter module 124. Specifically, a flow entering the MEMS filter module 124 through the second flow ports 142 will flow into the filter trap chamber 148a, through the corresponding filter trap gap 152, into a filter trap chamber 148a, and then out of the MEMS filter module 124 through the first flow ports 134. The reverse would be the case for a flow entering the MEMS filter module 124 through the first flow ports 134.

Figure 4A:
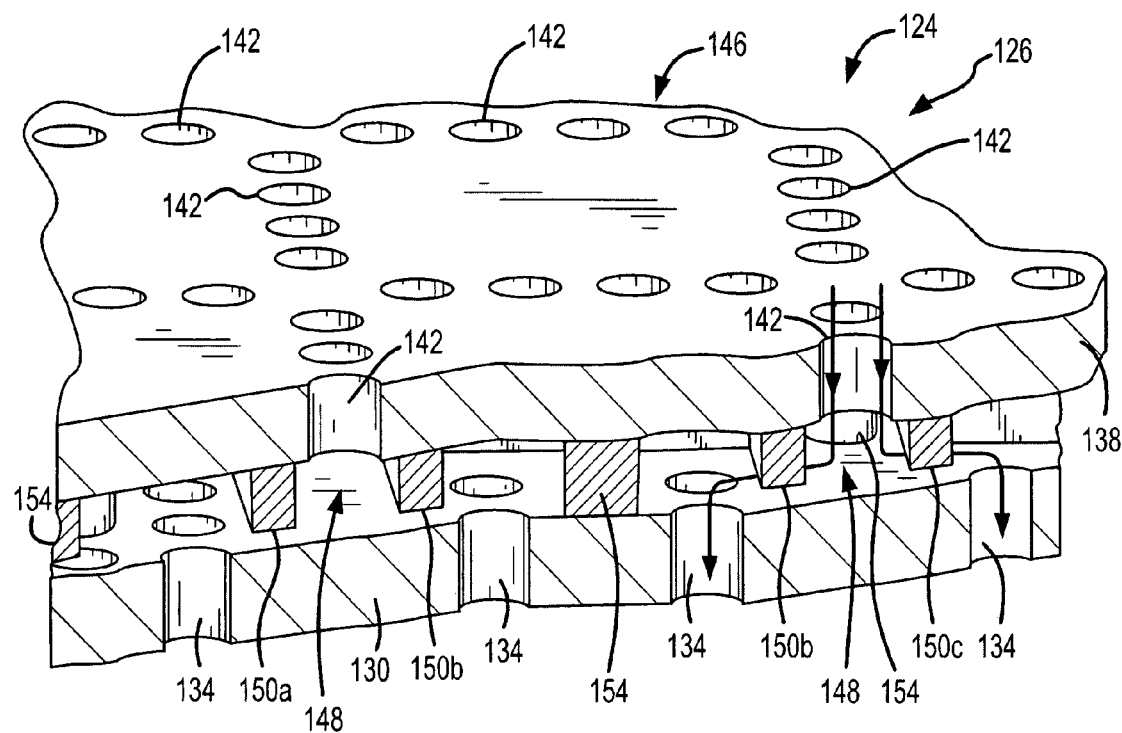
FIG. 4A is a perspective, cross-sectional view of one embodiment of a filtering region configuration that may be used throughout the filtering region of the MEMS filter module of FIG. 2A.
Figure 4B:
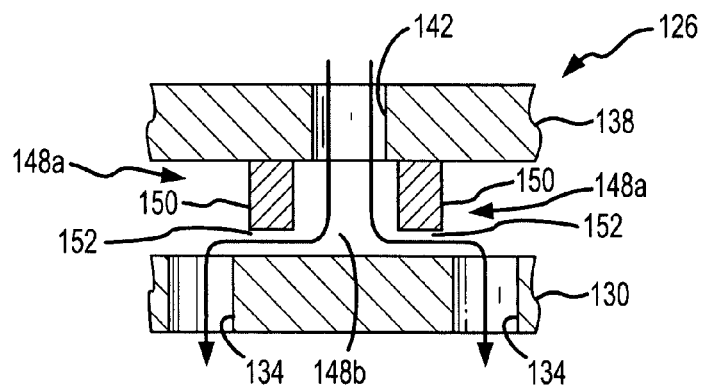
FIG. 4B is a cross-sectional view of a pair of filter traps used by the filtering region configuration of FIG. 4A.
Figure 4C:
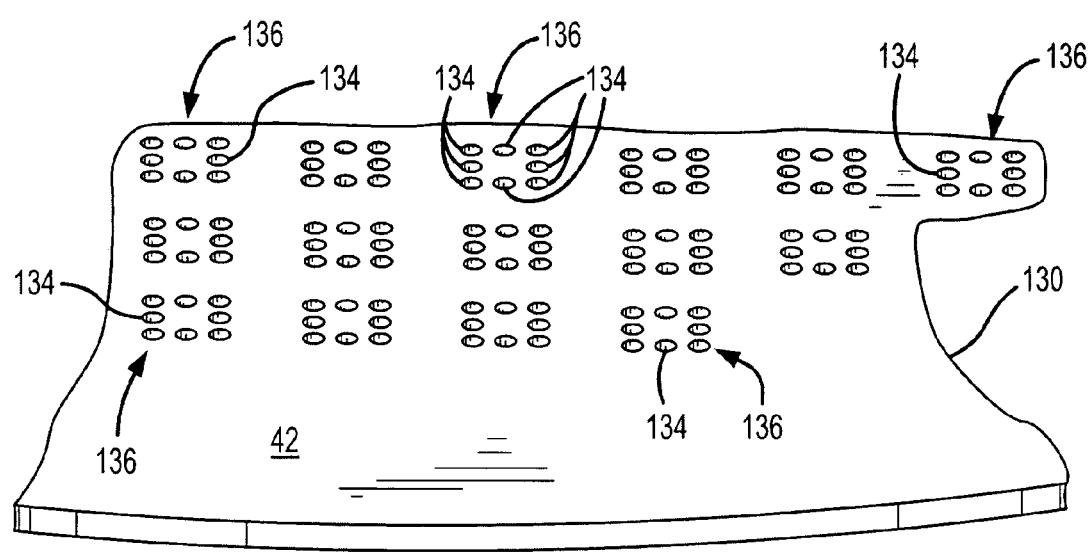
FIG. 4C is a perspective view of part of the lower film used by the filtering region configuration of FIG. 4A.
Figure 4D:
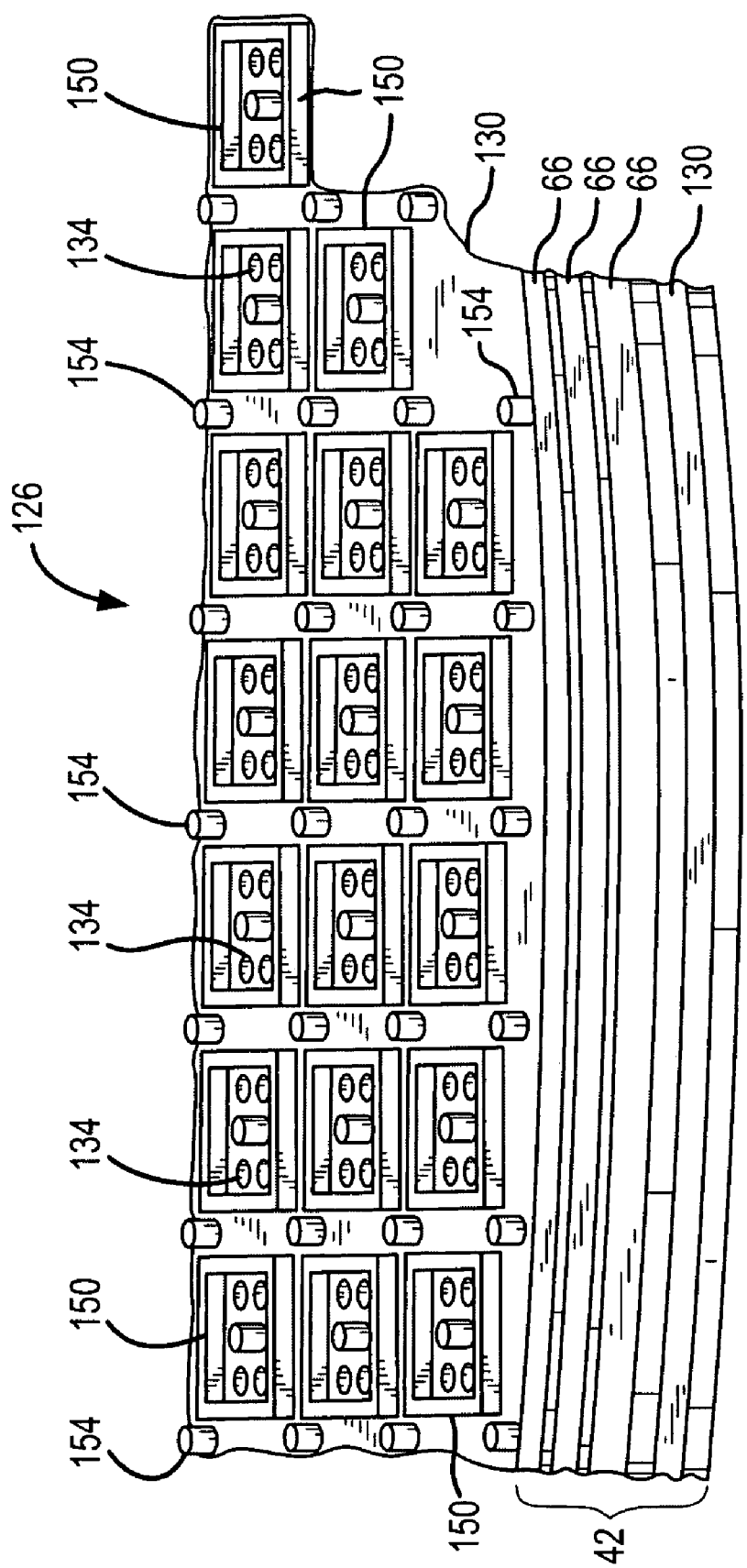
FIG. 4D is a perspective view of part of the filtering region configuration of FIG. 4A, with the upper film having been removed.
Figure 4E:
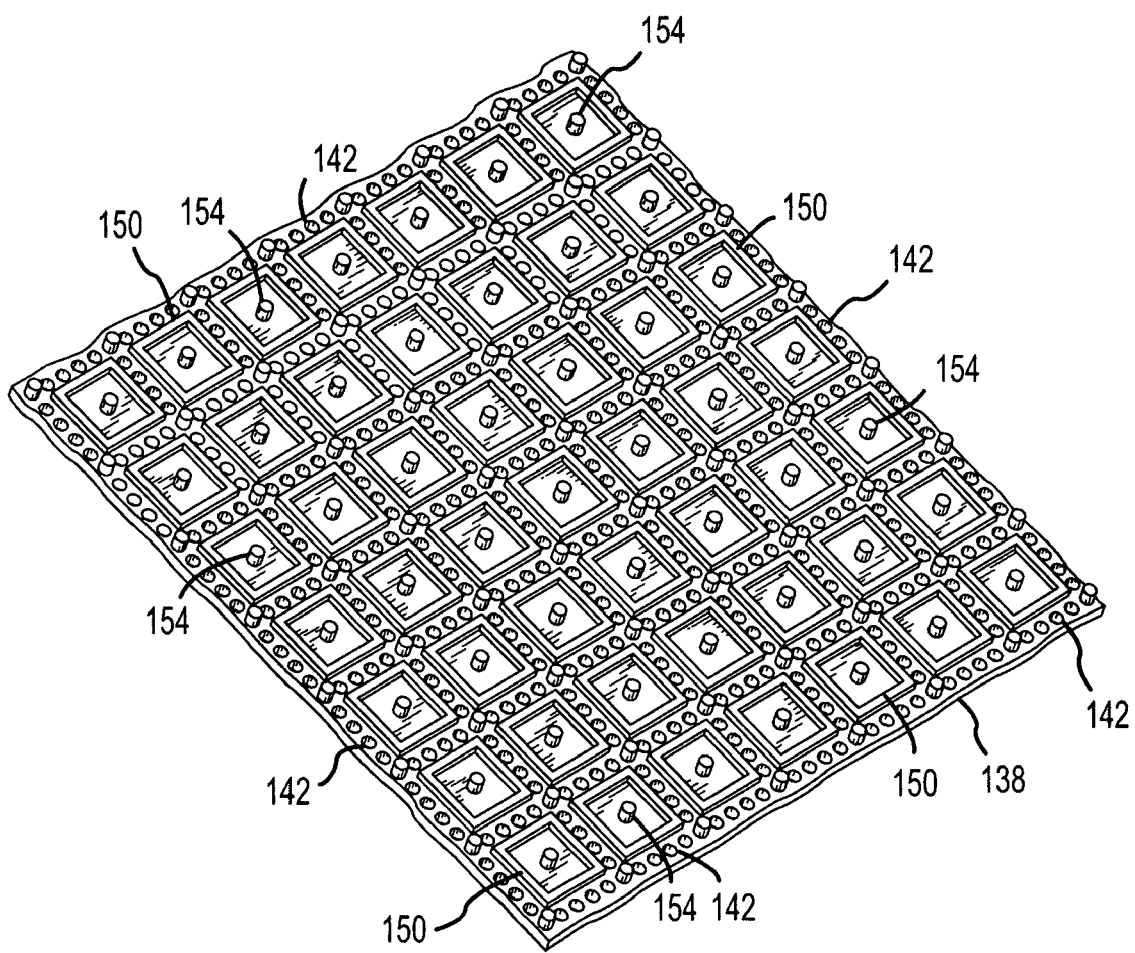
FIG. 4E is a perspective, bottom view of part of the upper film of the filtering region configuration of FIG. 4A, illustrating the filter walls and supports extending therefrom.
Figure 4F:
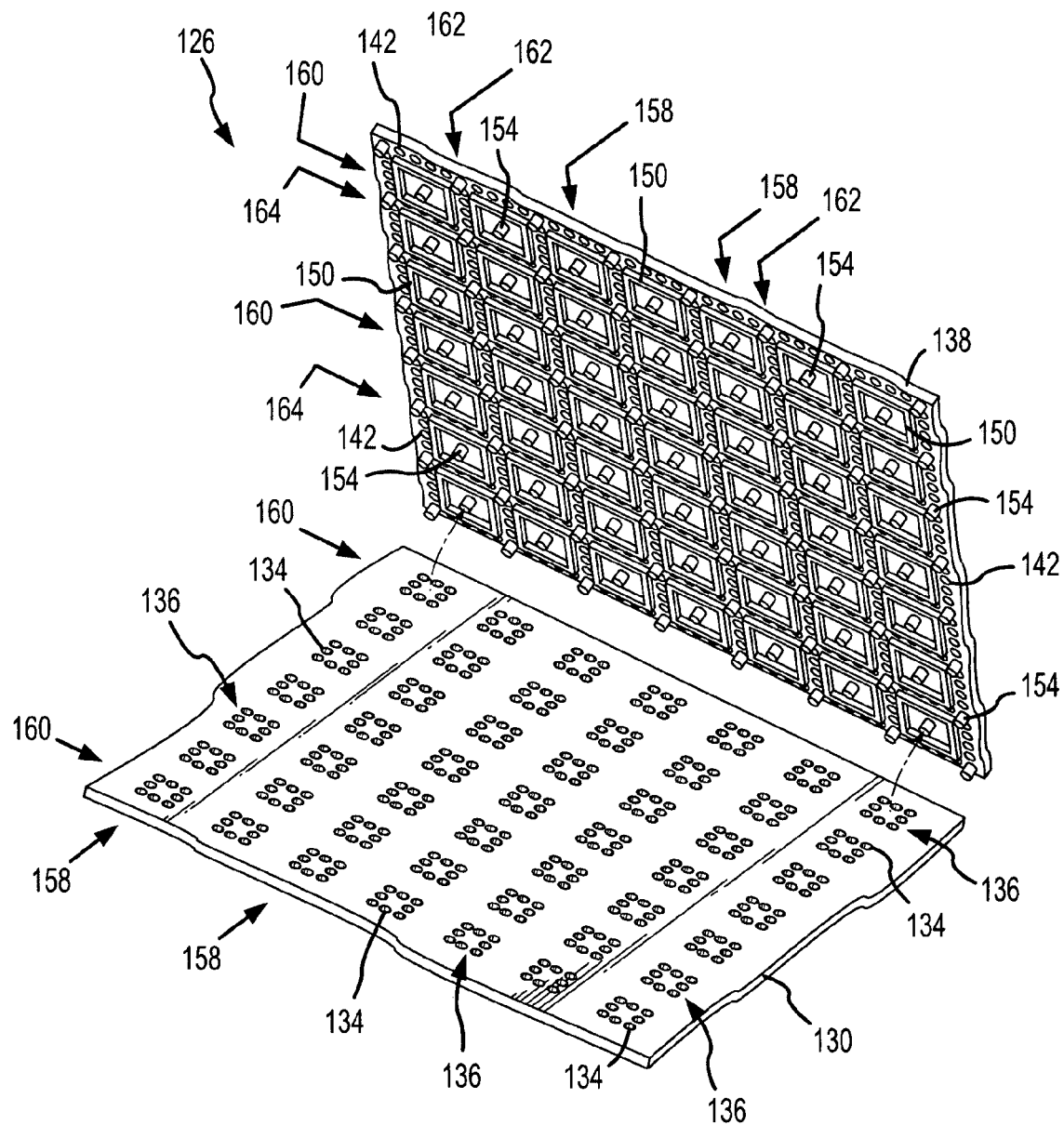
FIG. 4F is perspective view of part of the filtering region configuration of FIG. 4A, with the upper film having been exploded away from the lower film.
Figure 5A:
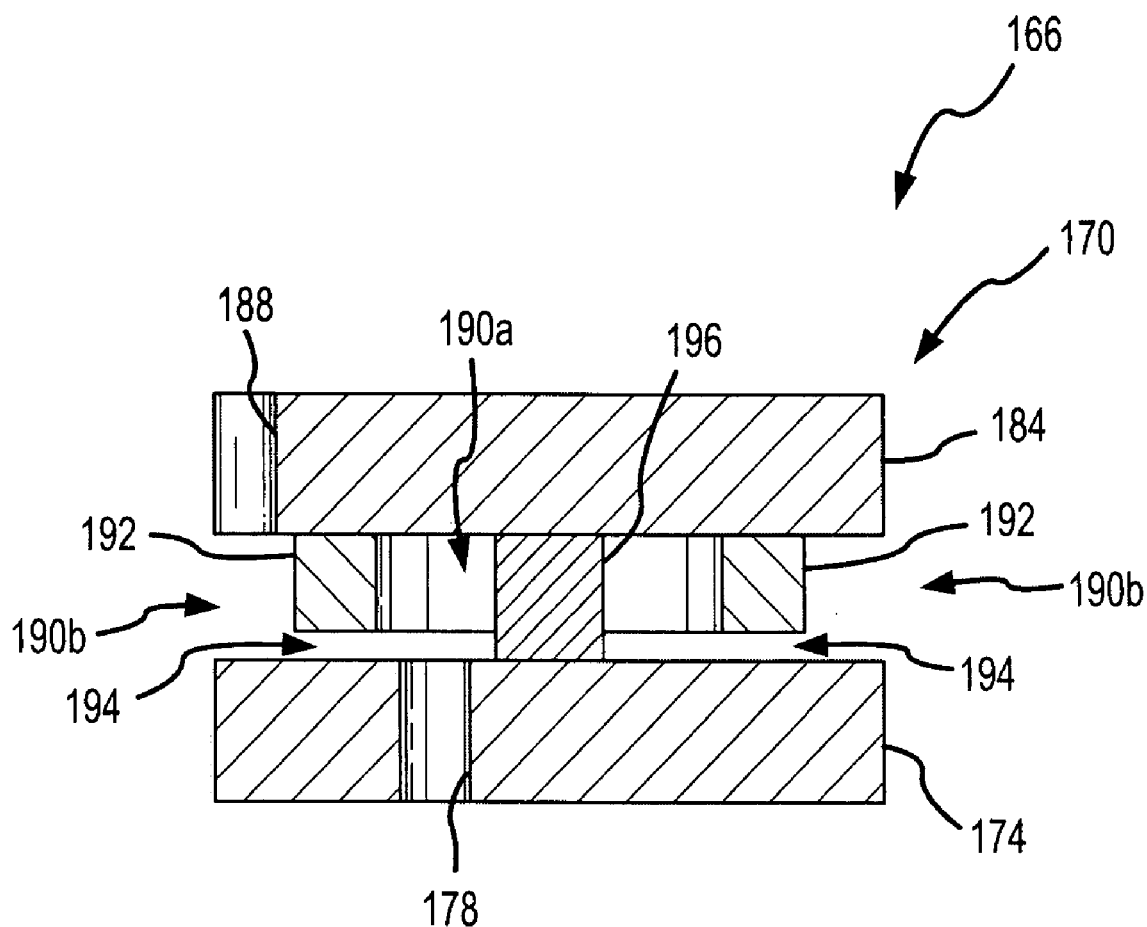
FIG. 5A is a cross-sectional view of another embodiment of a filtering region configuration that may be used throughout the filtering region of the MEMS filter module of FIG. 2A.
Figure 5B:
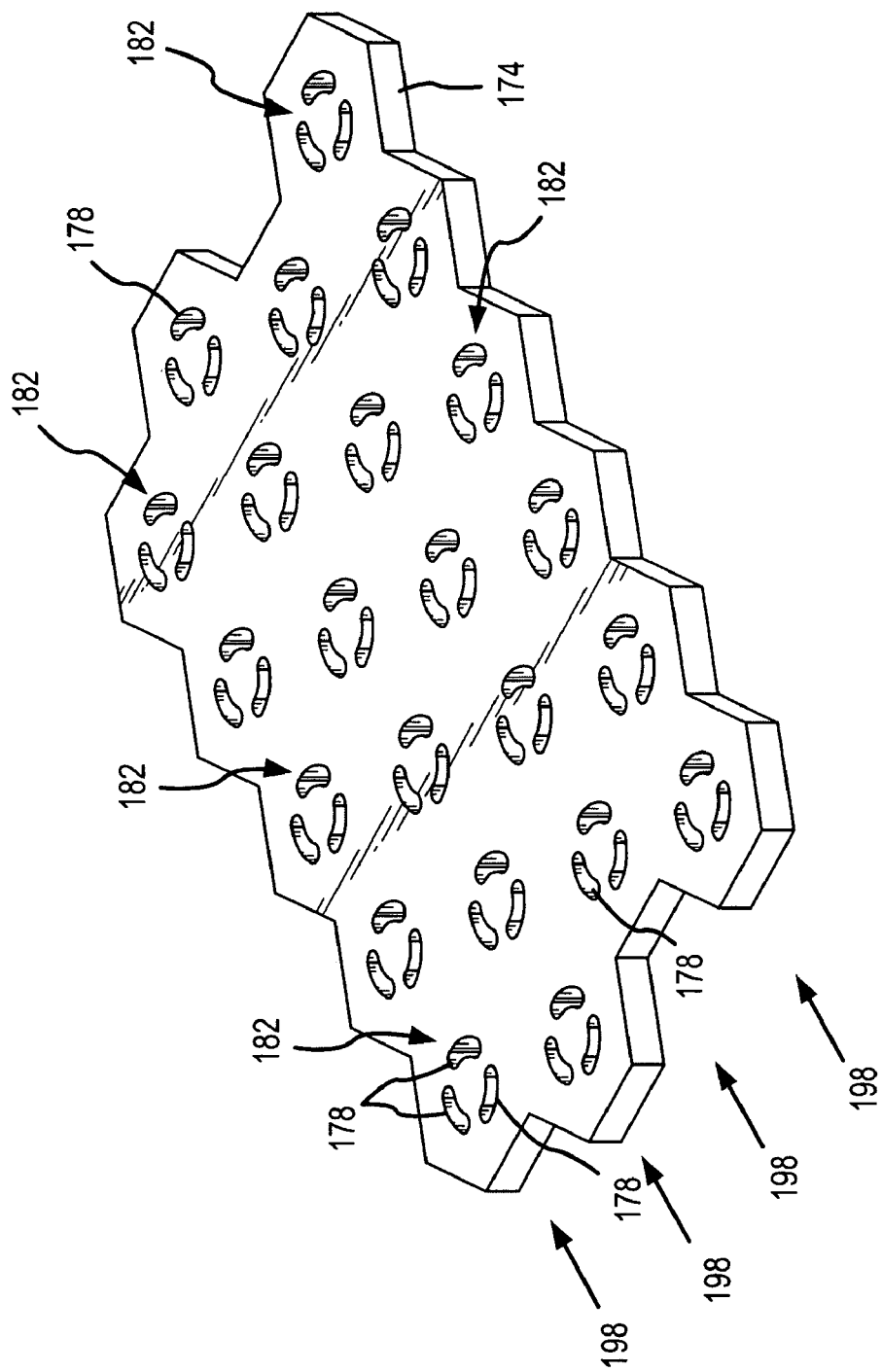
FIG. 5B is a perspective view of part of the lower film used by the filtering region configuration of FIG. 5A.
Figure 5C:
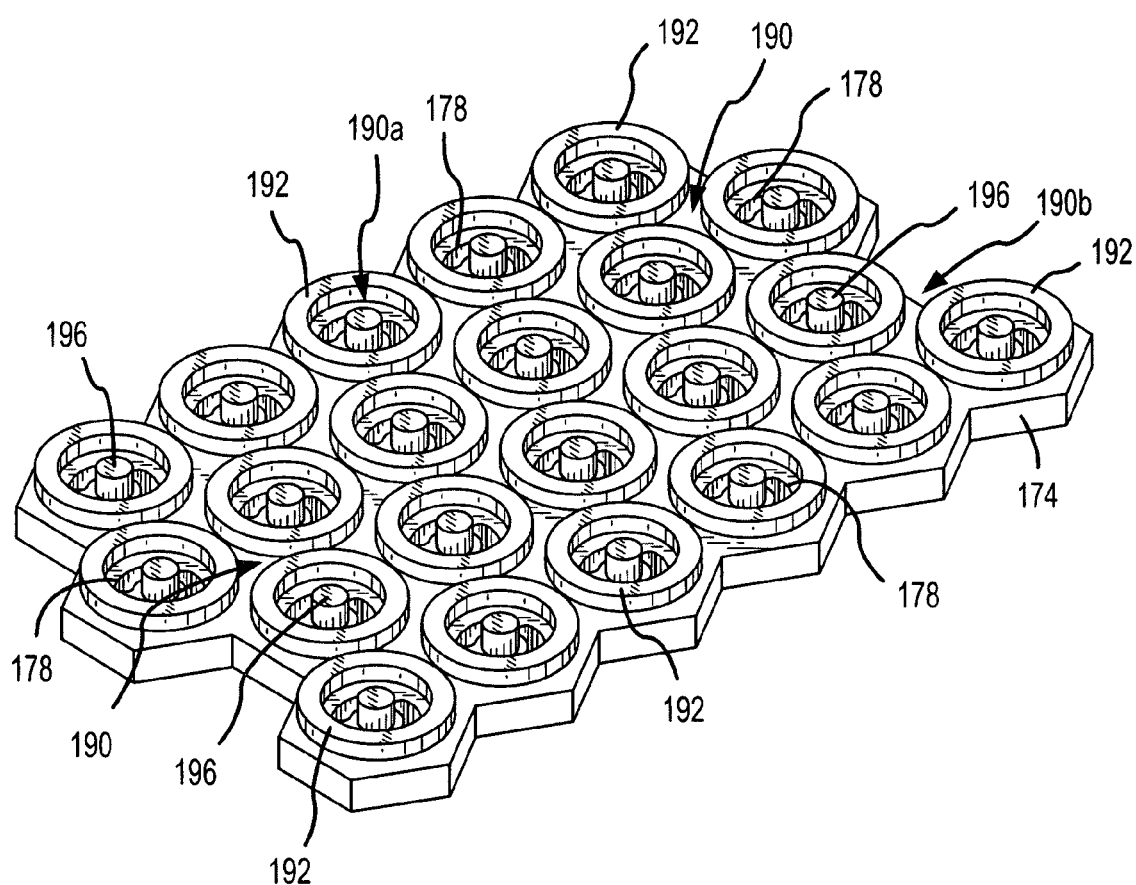
FIG. 5C is a perspective view of part of the filtering region configuration of FIG. 5A, with the upper film having been removed.
Figure 5E:
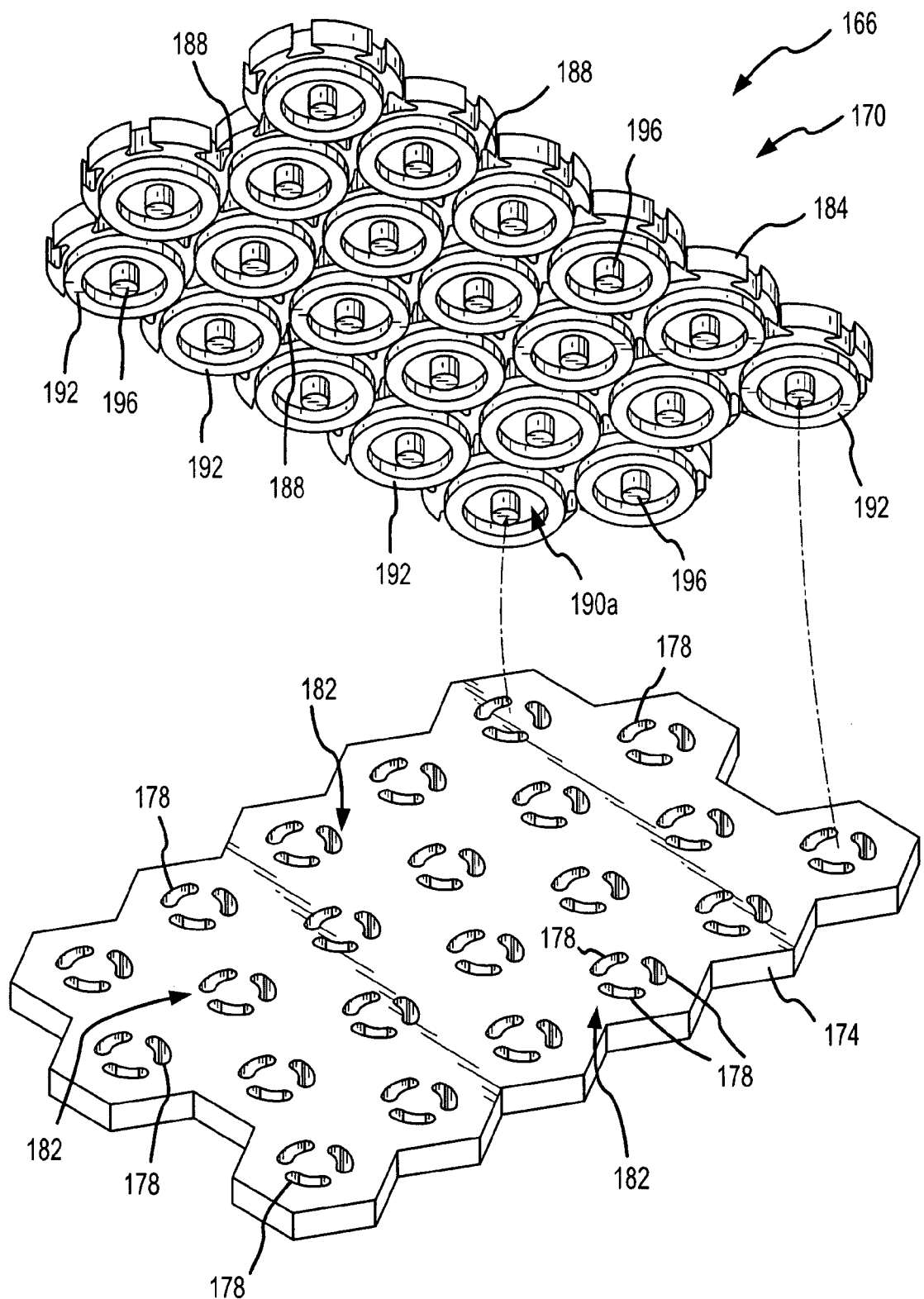
FIG. 5E is perspective view of part of the filtering region configuration of FIG. 5A, with the upper film having been exploded away from the lower film.
Figure 6A:
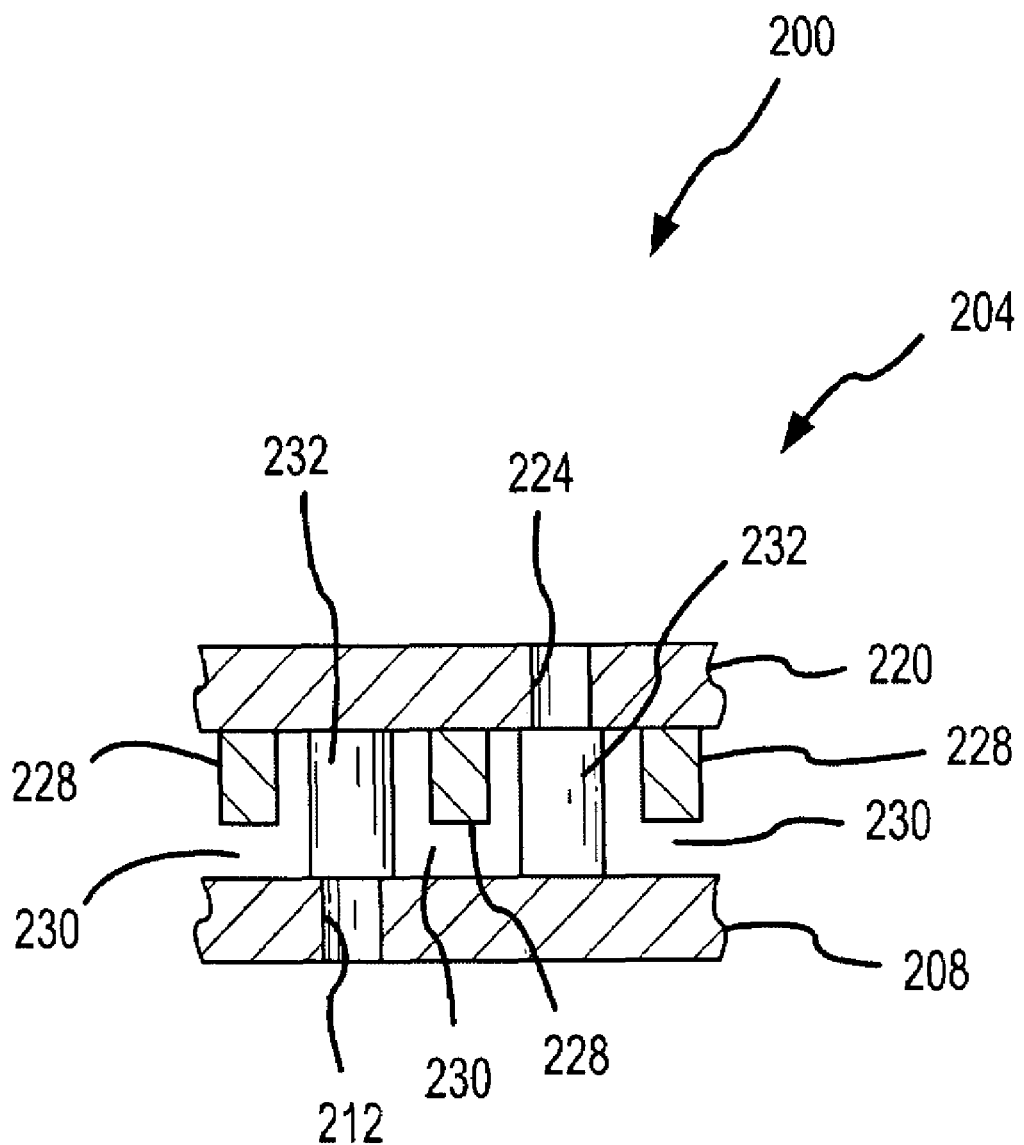
FIG. 6A is a cross-sectional view of another embodiment of a filtering region configuration that may be used throughout the filtering region of the MEMS filter module of FIG. 2A.
Figure 6B:
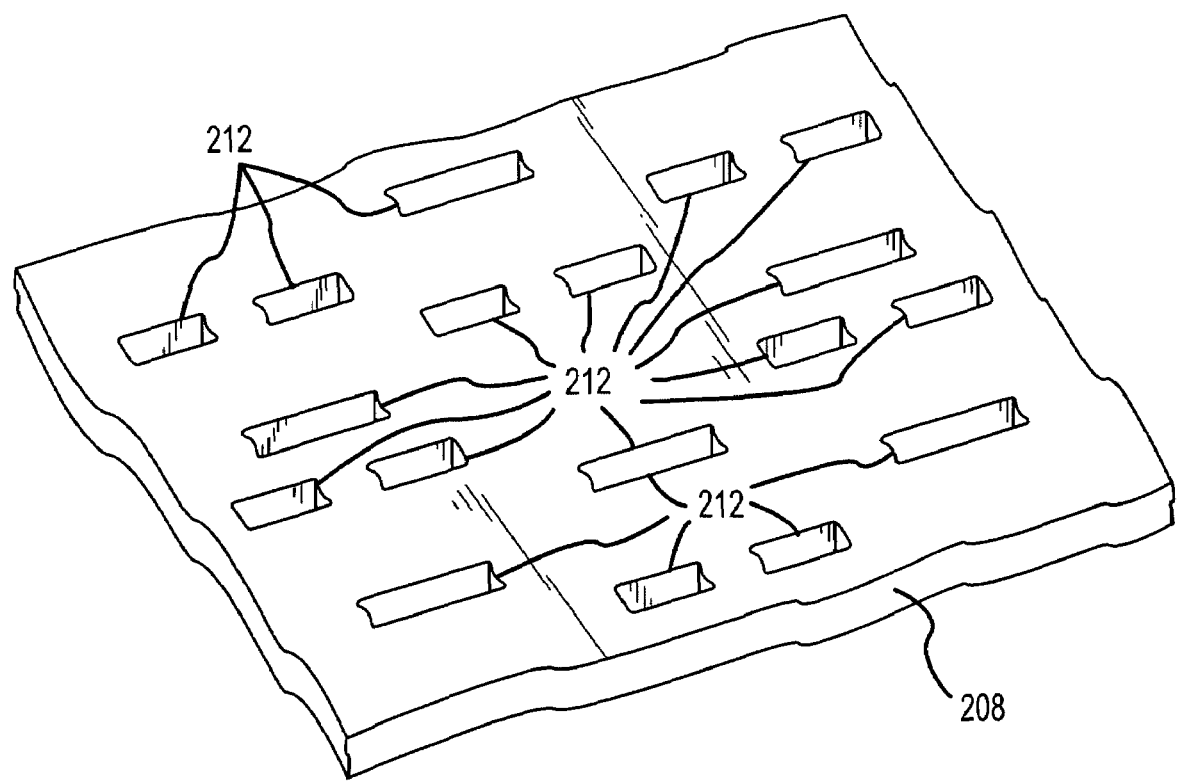
FIG. 6B is a perspective view of part of the lower film used by the filtering region configuration of FIG. 6A.
Figure 6C:
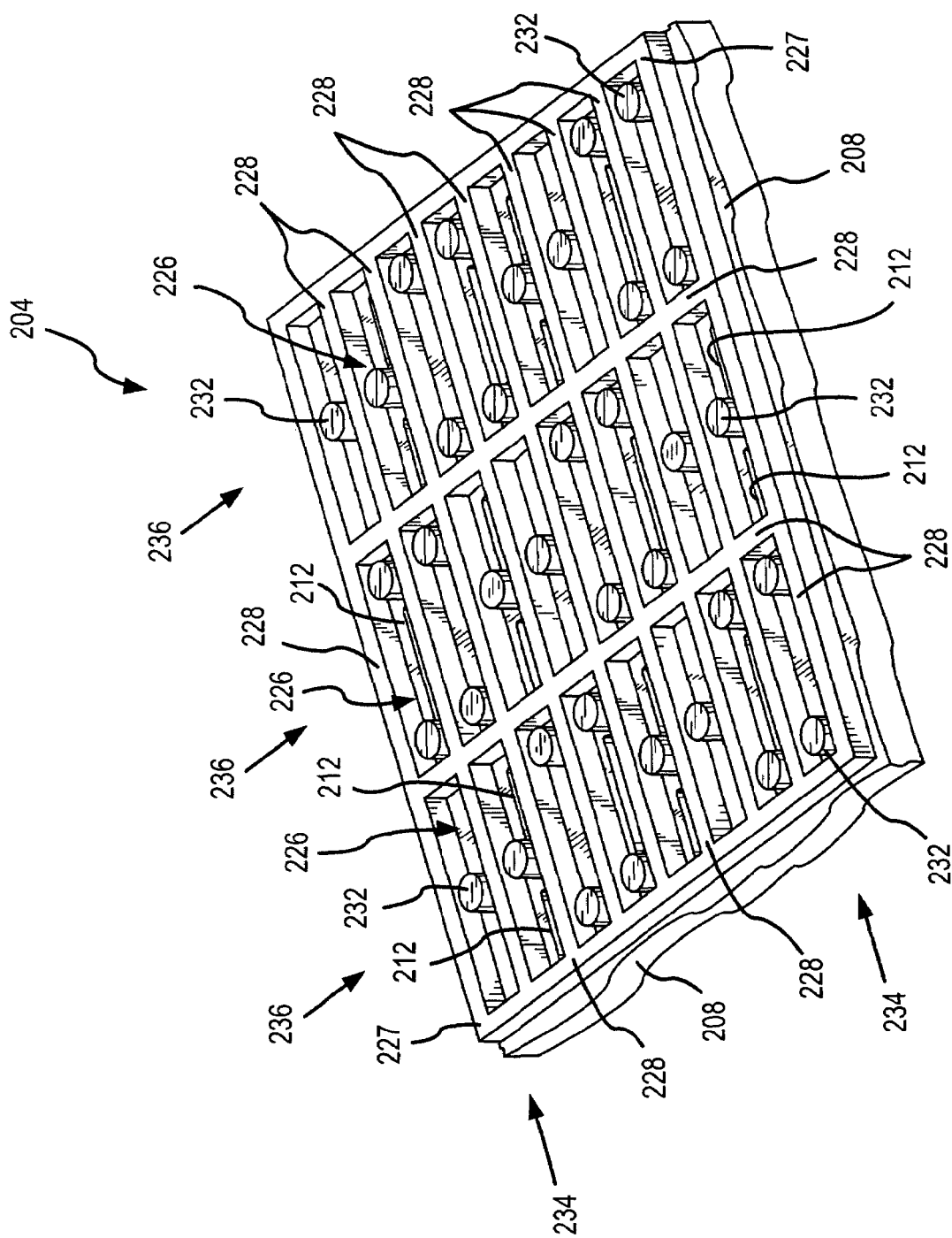
FIG. 6C is a perspective view of part of the filtering region configuration of FIG. 6A, with the upper film having been removed.
Figure 6D:
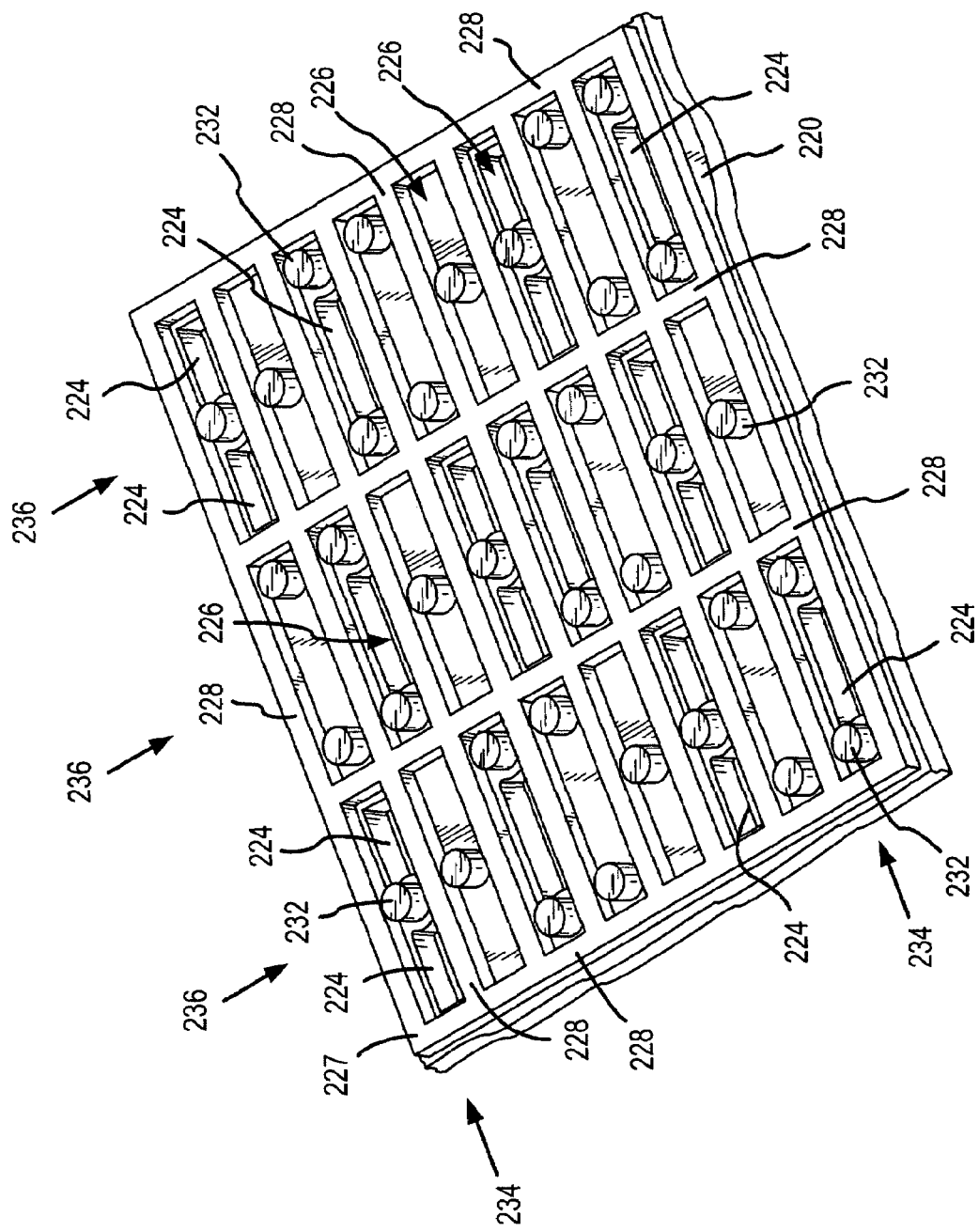
FIG. 6D is a perspective, bottom view of part of the upper film of the filtering region configuration of FIG. 6A, illustrating the filter walls and supports extending therefrom.
Figure 7A:
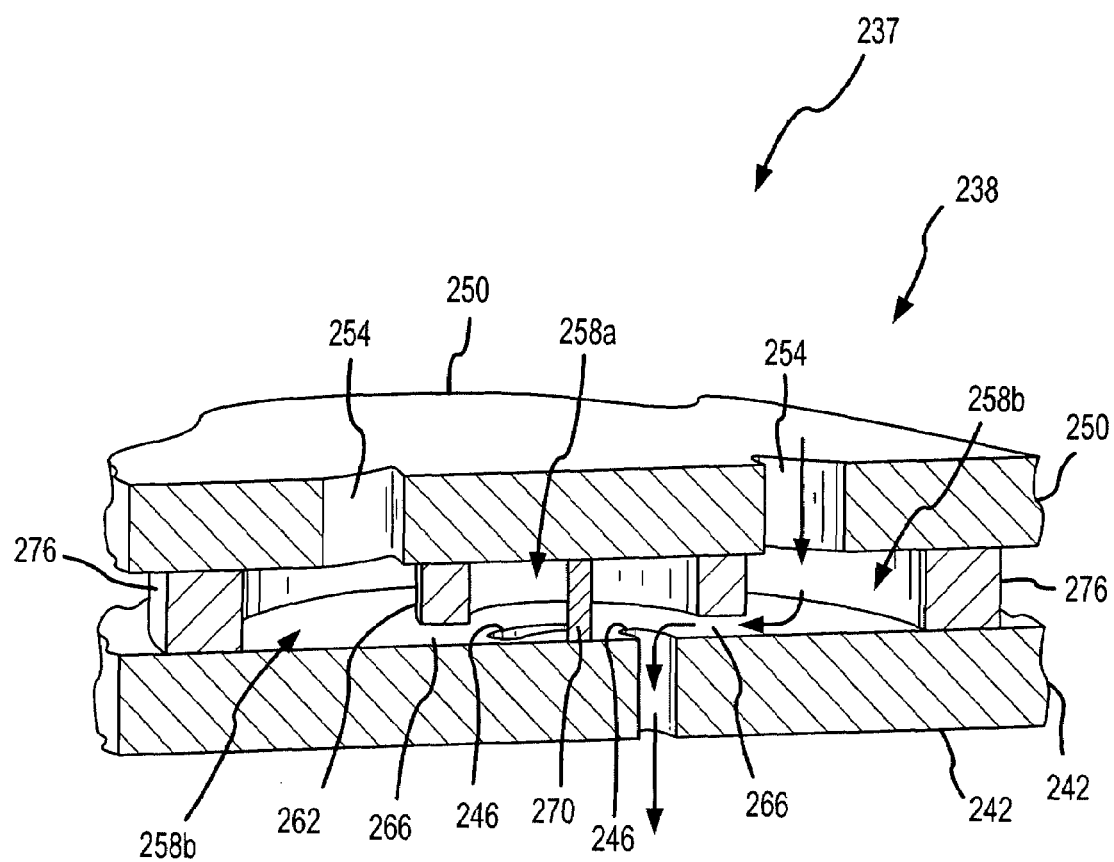
FIG. 7A is a perspective, cross-sectional view of another embodiment of a filtering region configuration that may be used throughout the filtering region of the MEMS filter module of FIG. 2A.
Figure 7B:
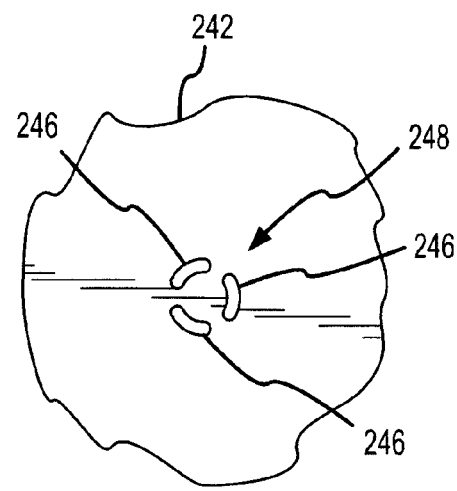
FIG. 7B is a top, plan view of part of the lower film used by the filtering region of FIG. 7A.
Figure 7C:
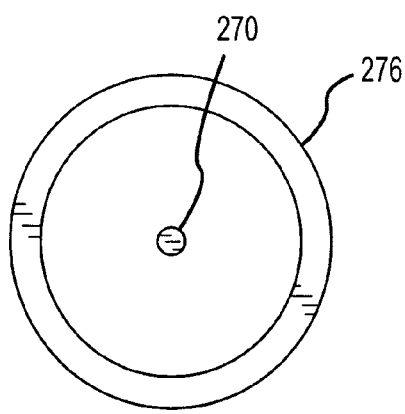
FIG. 7C is a top, plan view of one central support and its corresponding annular support/seal used by the filtering region of FIG. 7A.
Figure 7D:
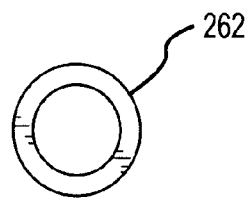
FIG. 7D is a top, plan view of one annular filter wall used by the filtering region of FIG. 7A.
Figure 7E:
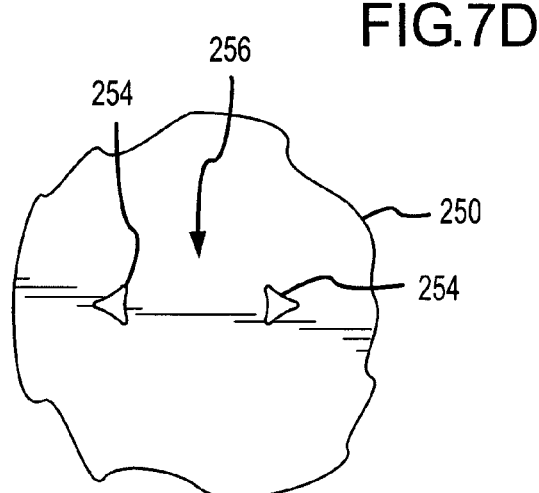
FIG. 7E is a top, plan view of part of the upper film used by the filtering region of FIG. 7A.
Figure 8A:
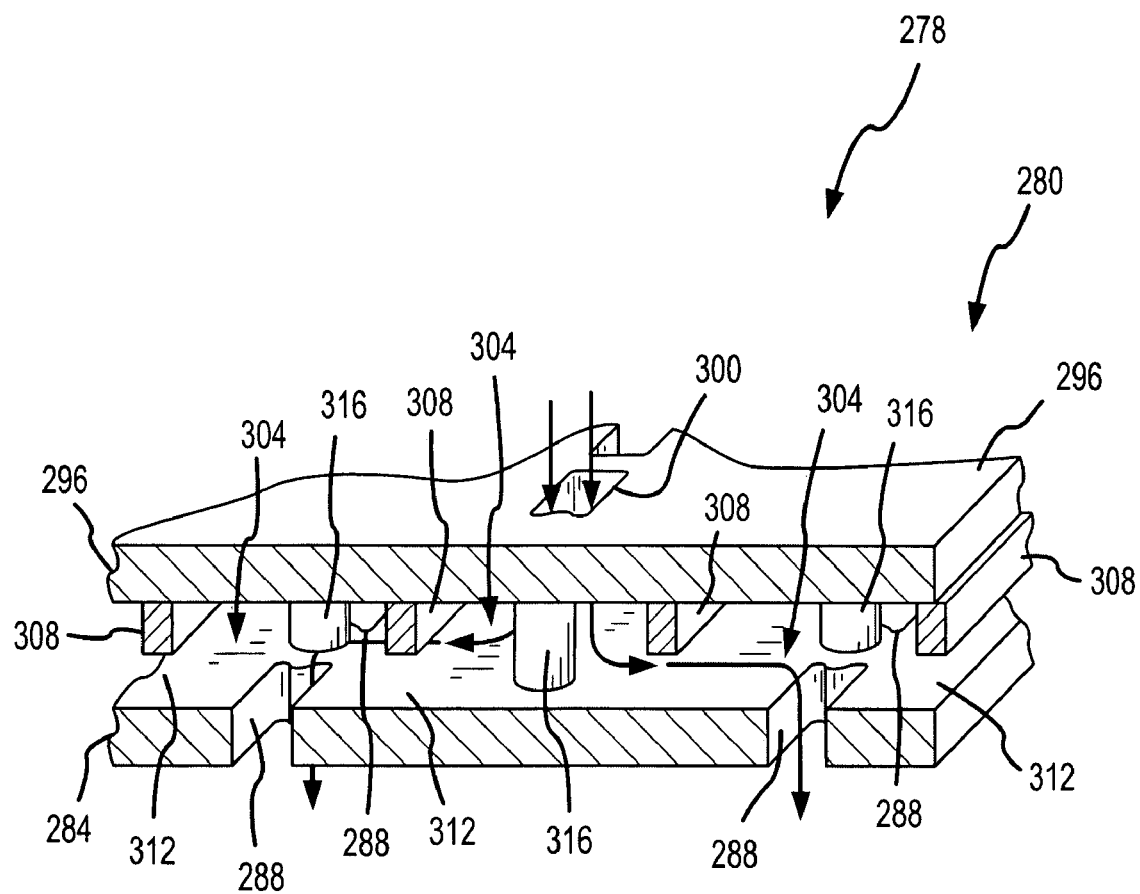
FIG. 8A is a perspective, cross-sectional view of another embodiment of a filtering region configuration that may be used throughout the filtering region of the MEMS filter module of FIG. 2A.
Figure 8B:
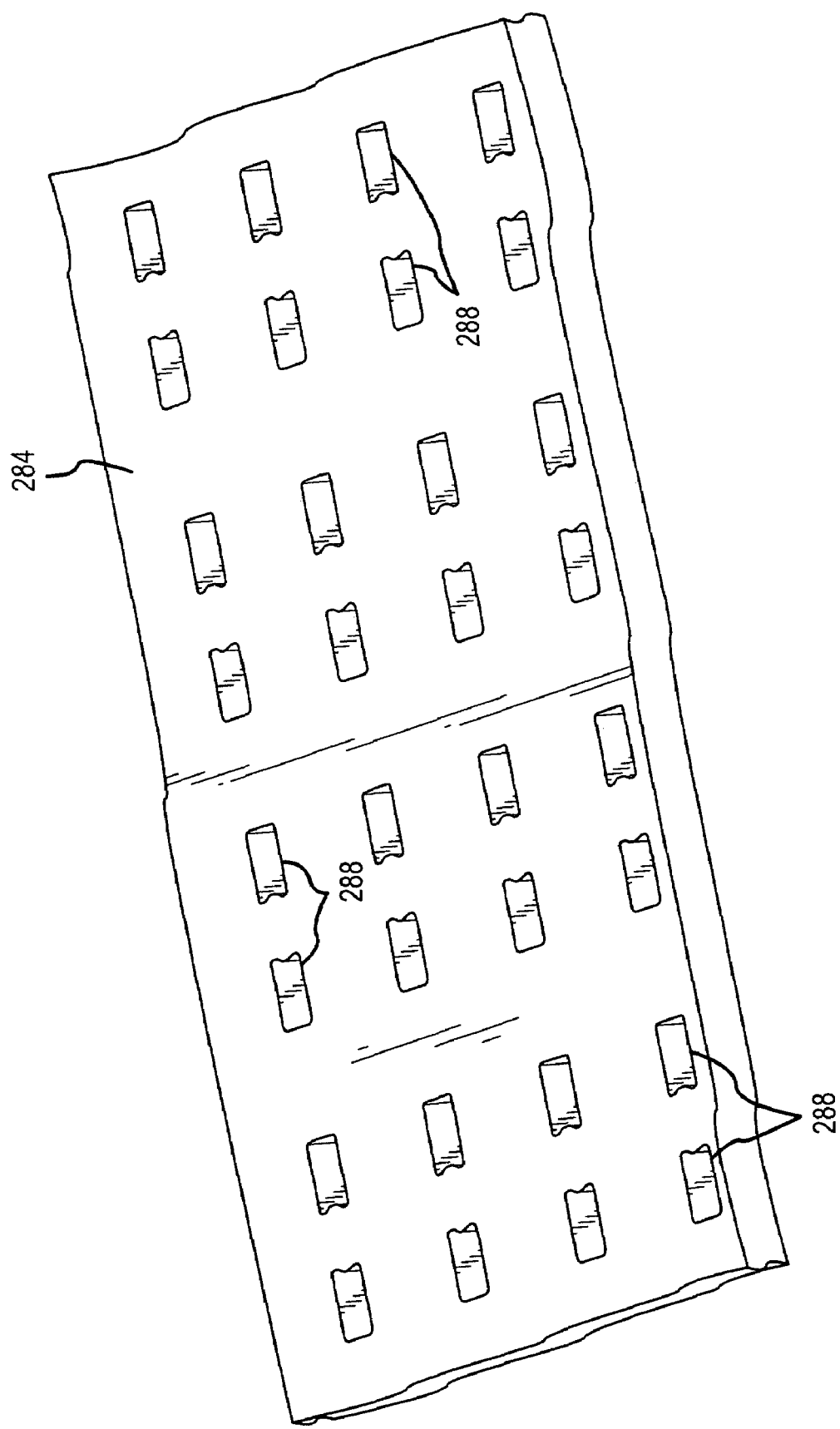
FIG. 8B is a perspective view of part of the lower film used by the filtering region configuration of FIG. 8A.
Figure 8C:
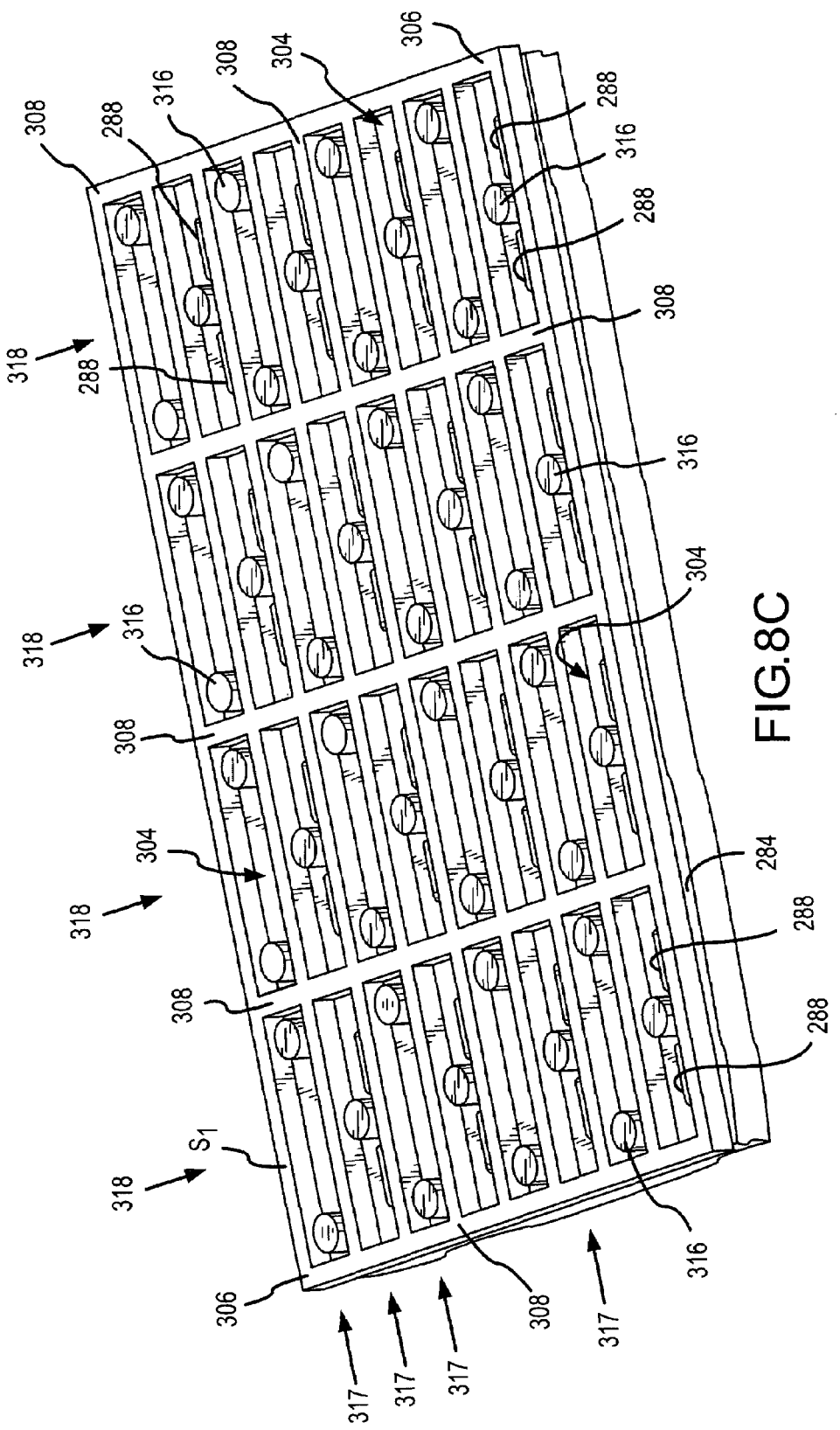
FIG. 8C is a perspective view of part of the filtering region configuration of FIG. 8A, with the upper film having been removed.
Figure 8D:
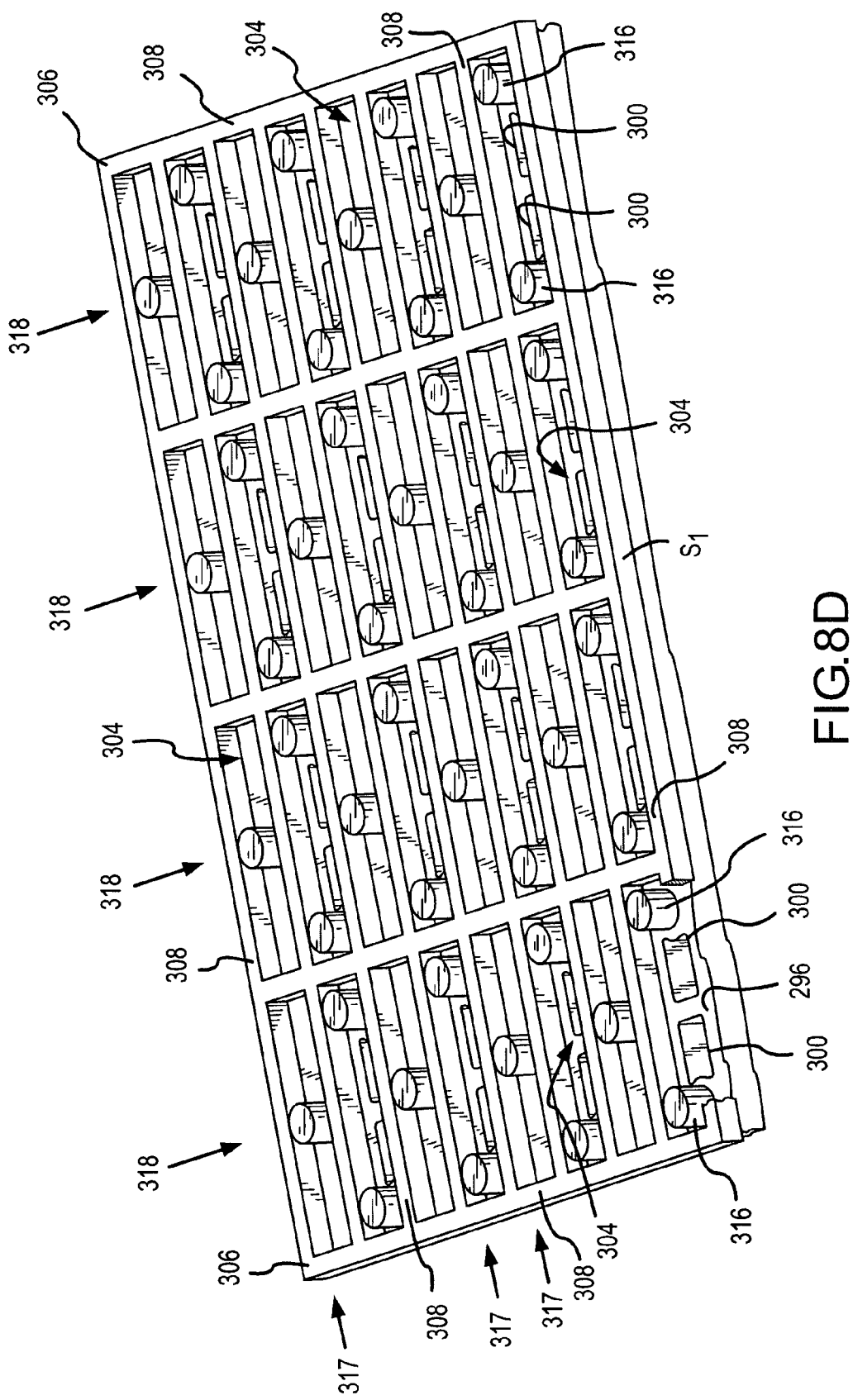
FIG. 8D is a perspective, bottom view of part of the upper film of the filtering region configuration of FIG. 8A, illustrating the filter walls and support posts extending therefrom.
Figure 9A:
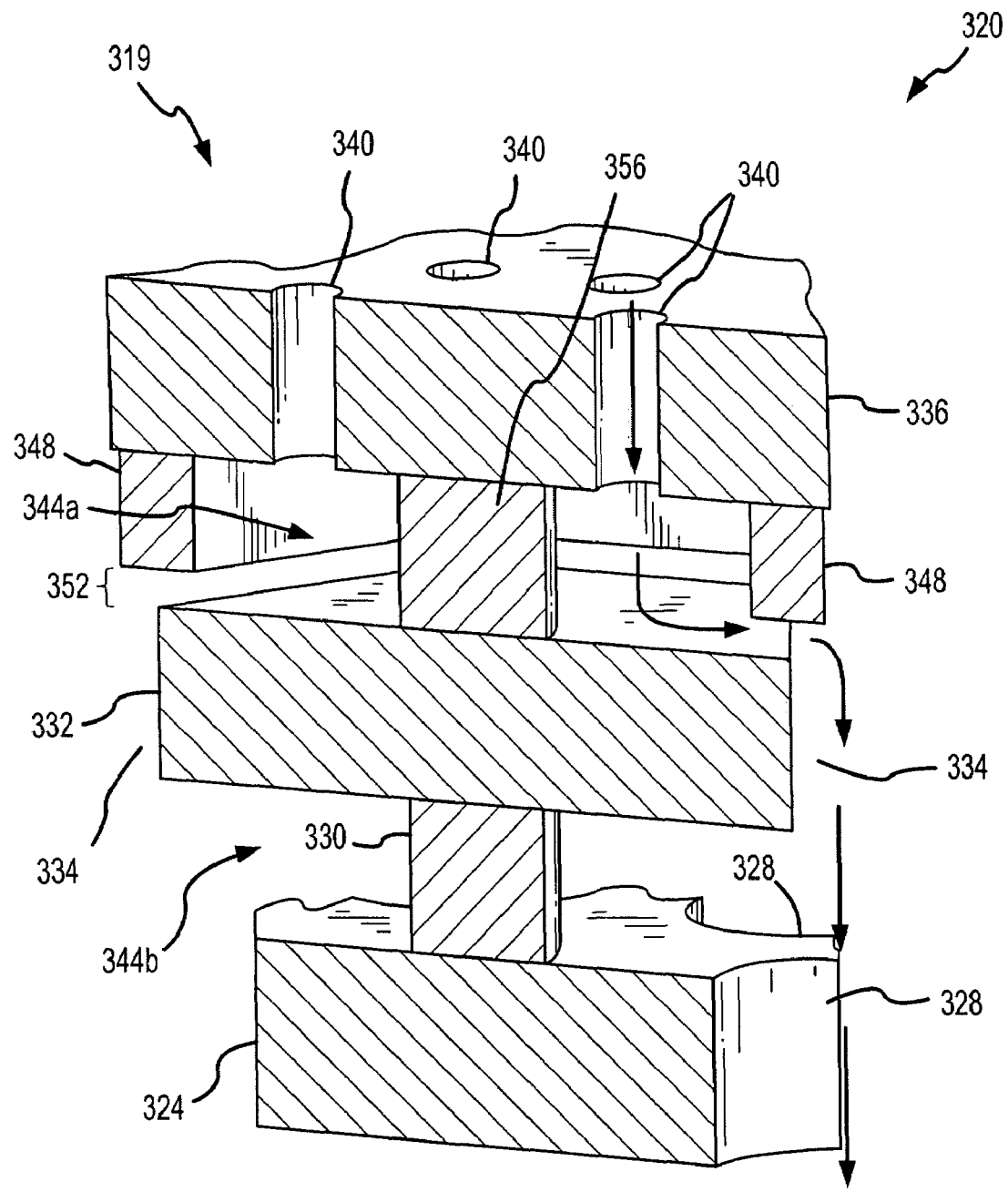
FIG. 9A is a perspective, cross-sectional view of another embodiment of a filtering region configuration that may be used throughout the filtering region of the MEMS filter module of FIG. 2A.
Figure 9B:
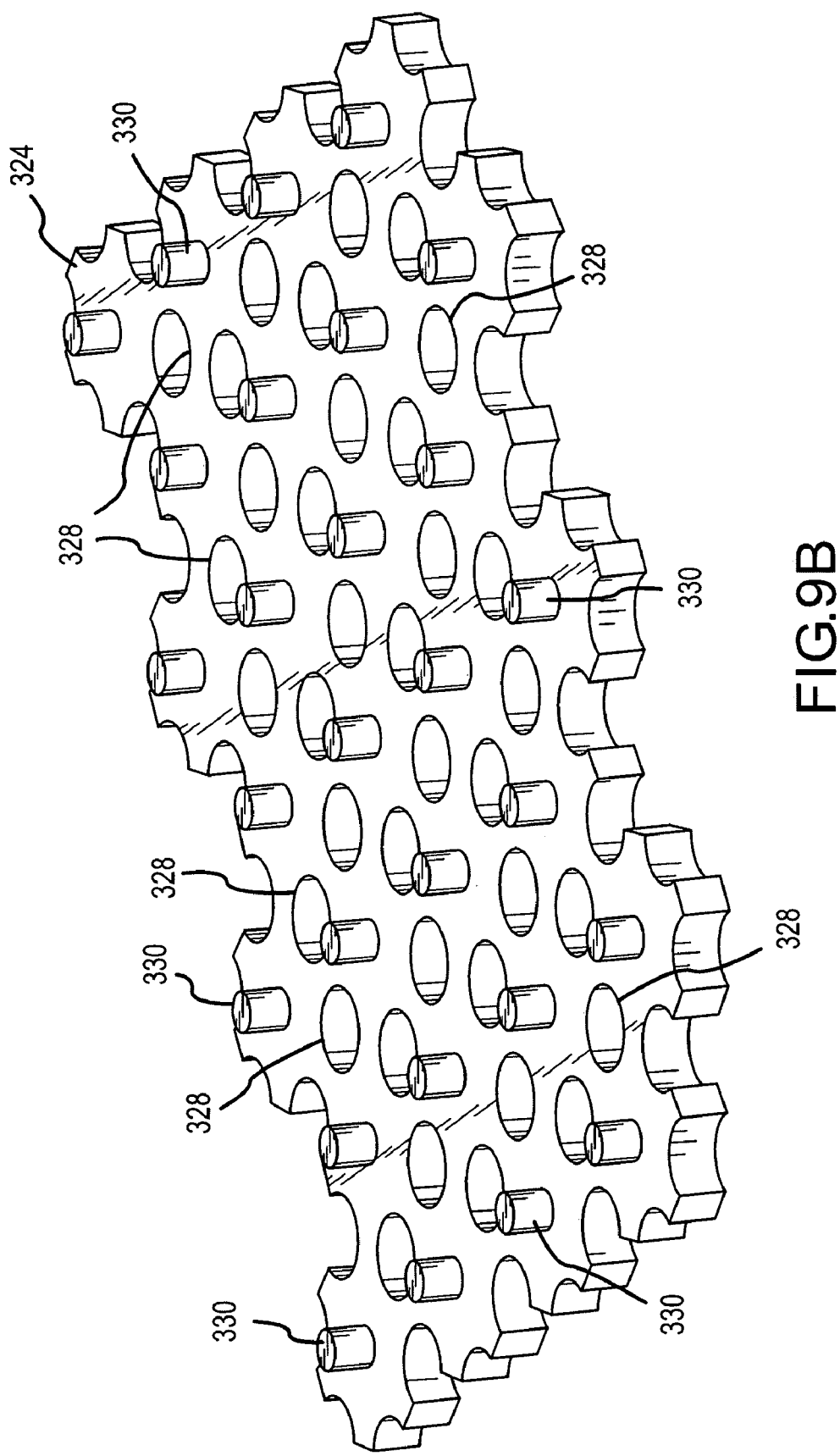
FIG. 9B is a perspective view of part of the lower film and the lower supports used by the filtering region configuration of FIG. 9A.
Figure 9D:
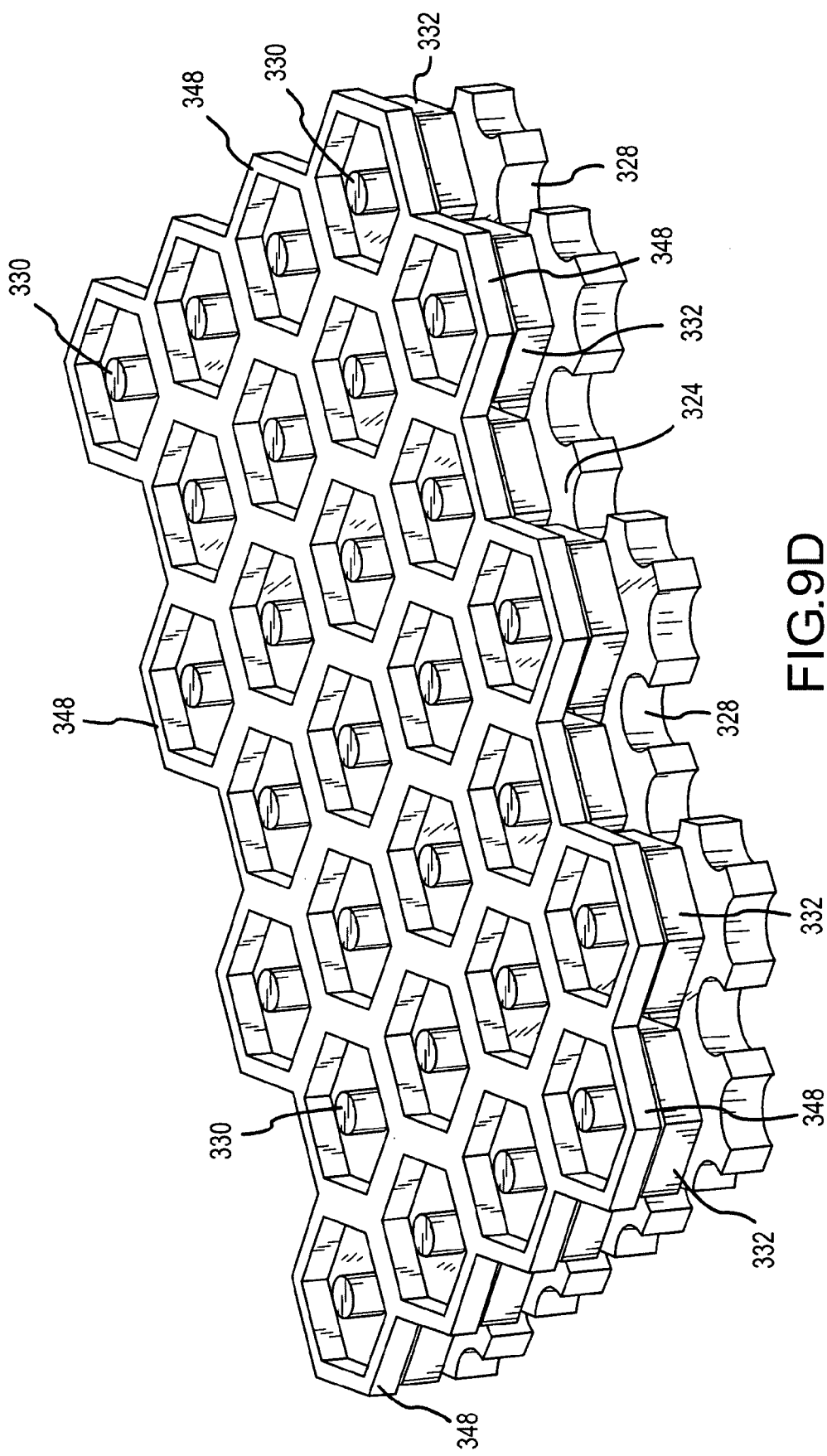
FIG. 9D is a perspective view of the filter walls positioned above the second film sections illustrated in FIG. 9B, as well as the upper supports used by the filtering region configuration of FIG. 9A.
Figure 9E:
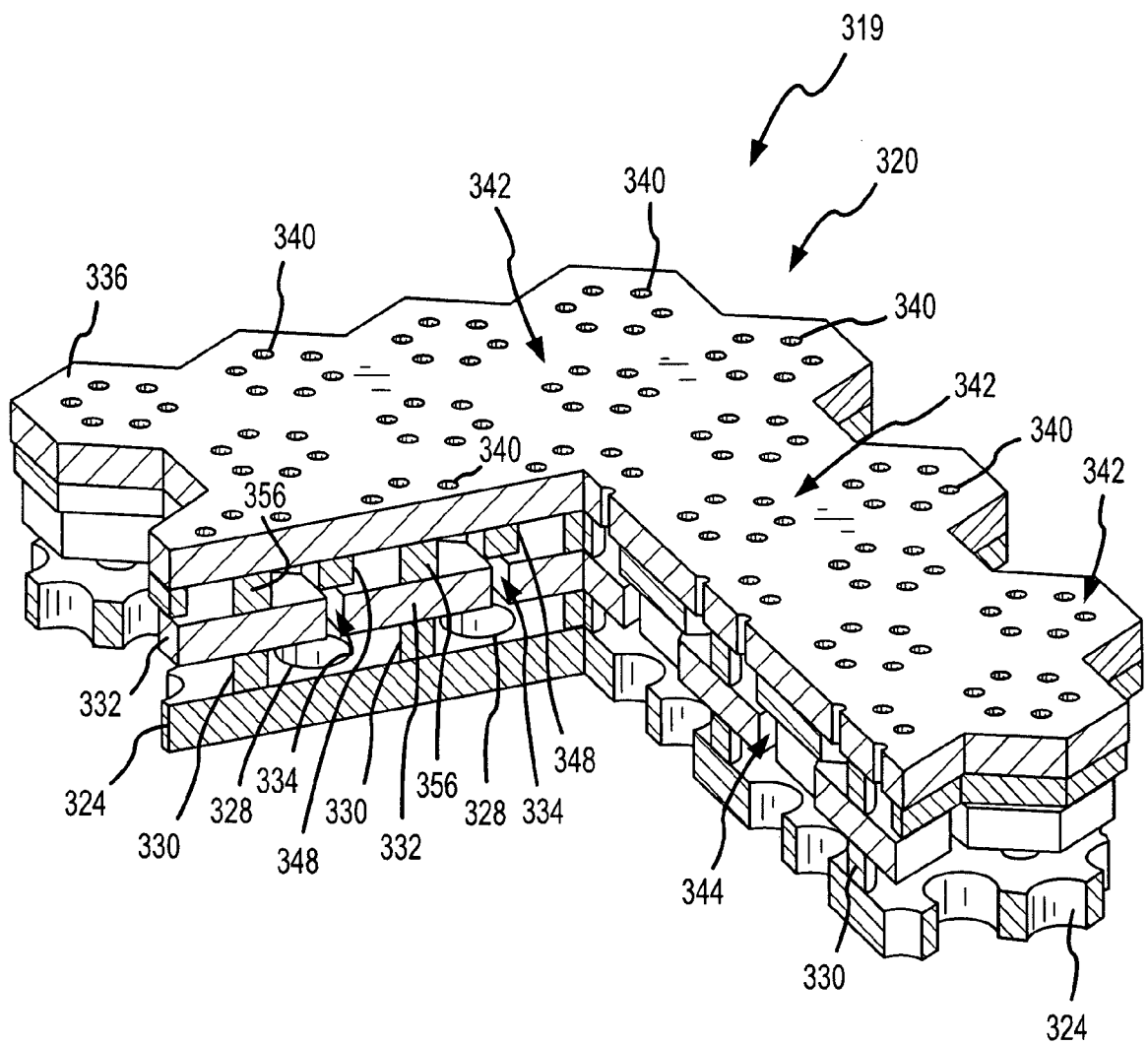
FIG. 9E is a perspective, cross-sectional view of additional portions of the filtering region configuration of FIG. 9A.

FIG. 4A identifies three separate, annular filter walls 150a, 150b, and 150c, while FIG. 4B identifies two separate, annular filter walls 150 for purposes of identifying interrelationships between the first flow ports 134, the second flow ports 142, and the filter walls 150. Generally, each first flow port 134 is disposed inwardly of an annular filter wall 150, while each second flow port 142 is disposed between the various annular filter walls 150.

A plurality of first flow ports 134 are fluidly interconnected with each filter trap chamber 148a (having a perimeter defined by a single filter wall 150), are disposed inwardly of their corresponding filter wall 150, and define a first flow port group 136. Any number of first flow ports 134 may be in each first flow port group 136, and the first flow ports 134 may be of any appropriate size and/or configuration (e.g., to accommodate the desired number/arrangement of supports 154 and the desired flow through the MEMS filter module 124). The filtering region 126 uses a plurality of first flow port groups 136. Each filter wall 150 thereby has a dedicated first flow port group 136. Providing multiple first flow ports 134 for each filter wall 150 reduces the impact of any particular first flow port 134 becoming plugged. Although reducing the number of first flow ports 134 that are associated with a particular filter wall 150 may reduce the flow rate through the corresponding filter trap chamber 148a defined by this filter wall 150, it will not totally disable the filter wall 150 in relation to its filtering function, unless all of its associated first flow ports 134 become plugged.

The various second flow ports 142 associated with the second film 138 in the filtering region 126 are disposed in the space between the various filter walls 150 that interface with and extend from the second film 138. A plurality of second flow ports 142 are disposed outwardly of (beyond) and about each filter wall 150, and define a second flow port group 146. Any number of second flow ports 142 may be disposed about each filter wall 150, and the second flow ports 142 may be of any appropriate size and/or configuration (e.g., to accommodate the desired number/arrangement of supports 154 and the desired flow through the MEMS filter module 124). The filtering region 126 uses a plurality of second flow port groups 146. It should be appreciated that a given second flow port 142 may be associated with more than one second flow port group 146 in the case of the filtering region 126.

Each filter wall 150 is associated with multiple second flow ports 142. Providing multiple second flow ports 142 for each filter wall 150 reduces the impact of any particular second flow port 142 becoming plugged on a given filter wall 150. It should be appreciated that each second flow port group 146 used by the filtering region 126 in effect could be used to provide a flow to or receive a flow from any filter trap chamber 148a. That is, each second flow port 142 of a particular second flow port group 146 could become plugged, and a flow could still be received from or directed to the fluid trap chamber 148a of the associated filter wall 150 by other second flow ports 142, including one or more second flow ports 142 from a different second flow port group 146. Reducing the number of second flow ports 142 that are available may of course reduce the flow rate through the filter module 124.

Based upon the foregoing, it should be appreciated that the first flow ports 136, second flow ports 142, filter walls 150, and supports 154 are distributed throughout the filtering region 126 of the filter module 124 in a repeating pattern. One way to characterize this pattern is that the first flow port groups 136, filter walls 150, and certain of the supports 154 are disposed in a plurality of rows 158 and a plurality of columns 160, and a plurality of second flow ports 142 are disposed about the filter walls 150 in each row 158 in the same manner. These rows 158 are disposed in parallel relation and are also equally spaced, as are the columns 160. The rows 158 extend in a direction that is perpendicular to a direction that the columns 160 extend. Any number of rows 158 and columns 160 may be utilized in the filtering region 126. The first flow port groups 136 are equally spaced in each row 158 and column 160, and the same spacing between adjacent first flow port groups 136 is used in each row 158 and column 160. The filter walls 150 are also equally spaced in each row 158 and column 160, and the same spacing between adjacent filter walls 150 is used in each row 158 and column 160. The supports 154 are also equally spaced in each row 158 and column 160, and the same spacing between adjacent supports 154 is used in each row 158 and column 160.

There are also a plurality of rows 162 of supports 154 between each of the above-noted rows 158, and a plurality of columns 164 of supports 154 between each of the above-noted columns 160. These rows 162 are thereby disposed in parallel relation and are also equally spaced, as are the columns 164. The supports 154 are equally spaced in each row 162 and column 164. It should be appreciated that there may be instances where there are not complete repeats of the above-noted pattern in the filtering region 126.

FIGS. 5A-E illustrate one embodiment of a MEMS filter module 166 having a filtering region 170. The filter module 166 includes a first film 174 and a second film 184 that are disposed in spaced relation or at different elevations. Each of these films 174, 184 defines an extreme for the MEMS filter module 124 in both the filtering region 170 and in its perimeter region (not shown, but in accordance with the perimeter region 42 of the MEMS filter module 34 of FIGS. 2A-F). As such, the films 174, 184 would be interconnected and supported about their respective perimeter regions by each annular seal 66 used by the MEMS filter module 166. The films 174, 184 are thereby "continuous" structures in the same manner discussed above in relation to the films 70, 46.

The first film 174 includes a plurality of first flow ports 178, while the second film 184 includes a plurality of second flow ports 188. All of the first flow ports 178 and all of the second flow ports 188 are located only in the filtering region 170 of the filter module 166 (i.e., none are. in the perimeter region 42). A plurality of supports 196 extend between and structurally interconnect the first film 174 and the second film 184 in the filtering region 170. These supports 196 are distributed throughout the filtering region 170 in a repeating pattern, are disposed in spaced relation to each other, and may be of any appropriate configuration. A plurality of filter walls 192 are attached to and extend from the second film 184 and at least toward (in the direction of) the first film 174. Any number of filter walls 192 may be utilized in the filtering region 170 of the MEMS filter module 166. Although any number of supports 196 may be utilized as well, the number and location of the supports 196 is subject to the characterizations discussed above in relation to the supports 78. The supports 196 are subject to a number of additional characterizations as well. One is that a single support 196 is positioned inwardly of each filter wall 192 in a central location. Another is that no supports 196 are disposed in the space between adjacent filter walls 192.

Each filter wall 192 has an annular configuration. "Annular" in this context means that each filter wall 192 has a closed perimeter when looking at the distal end of the filter wall 192 (that which is opposite the end of the filter wall 192 that interfaces with the second film 184). Stated another way, each filter wall 192 extends a full 360 degrees about a certain reference axis along any appropriate path. Although each filter wall 192 has a circular, annular extent in the illustrated embodiment, any configuration could be utilized for the filter wall 192 to realize the noted annular extent (e.g., rectangular, square, oval, triangular). Each filter wall 192 also does not extend all the way to the first film 174. Instead, a filter trap or filter trap gap 194 exists between the distal end of each filter wall 192 and the first film 174. Since each filter wall 192 is annular, its corresponding filter trap gap 194 will likewise be annular. Note that each filter wall 192 is also offset from the various first flow ports 178 and second flow ports 188, thereby inducing at least one change in direction for the flow through the MEMS filter module 166.

Flow may be directed through each filter trap gap 194 to provide a filtering function. Any constituent in the flow (e.g., particulates, cells of a certain size) that is larger than the height of a particular filter trap gap 194 will typically be collectively retained by the corresponding filter wall 192 and the first film 174 (i.e., by being unable to pass through the filter trap gap 194). Since each filter trap 194 is annular in the case of the MEMS filter module 166, any constituent that is "trapped" by being unable to pass through a particular filter trap gap 194 will then not totally "plug" the filter trap gap 194. Having an annular filter trap gap 194 associated with each filter wall 192 also provides a desired flow rate through the MEMS filter module 166. The number and location of the various supports 196 is preferably selected such that the height of each filter trap gap 194 throughout the filtering region 170 is maintained within a small tolerance for the maximum flow rate for which the filter module 170 is designed in the same manner discussed above in relation to the filter trap gap 58.

The flow may enter the MEMS filter module 166 either through the second flow ports 188 (in which case the flow out of the MEMS filter module 166 would be through the first flow ports 178), or through the first flow ports 178 (in which case the flow out of the MEMS filter module 166 would be through the second flow ports 188). In either case, the flow will be directed into either a space 190a or a space 190b that extends from the first film 174 to the second film 184 before attempting to pass through a filter trap gap 194 associated with a particular filter wall 192. Each of these spaces 190a, 190b in the filtering region 170 may be characterized as a filter trap chamber 190a, 190b. The height of each filter trap chamber 190a, 190b corresponds with the spacing between the first film 174 and the second film 184, which is greater than the height of the filter trap gap 194. Each annular filter wall 192 defines a filter trap chamber 190a, while the space between the various filter walls 192 defines a single filter trap chamber 190b.

The volume of each filter trap chamber 190a may be larger than the volume of any associated first flow port 178, while the volume of the filter trap chamber 190b may be larger than the volume of any associated second flow port 188, although such is not a requirement. Whether the flow enters the MEMS filter module 166 through the first flow ports 178 or the second flow ports 188, the flow will go through a filter trap chamber 190a or the filter trap chamber 190b, then through a filter trap gap 194, and then through the other of a filter trap chamber 190a or the filter trap chamber 190b. Specifically, a flow entering the MEMS filter module 166 through the second flow ports 188 will flow into the filter trap chamber 190b, through the corresponding filter trap gap 194, into the corresponding filter trap chamber 190a, and then out of the MEMS filter module 166 through the first flow ports 178. The reverse would be the case for a flow entering the MEMS filter module 166 through the first flow ports 178.

A plurality of first flow ports 178 are fluidly interconnected with each filter trap chamber 190a (having a perimeter defined by a single filter wall 192), are disposed inwardly of their corresponding filter wall 192, and define a first flow port group 182. Any number of first flow ports 178 may be in each first flow port group 182, and the first flow ports 178 may be of any appropriate size and/or configuration (e.g., to accommodate the desired number/arrangement of supports 196 and the desired flow through the MEMS filter module 166). The filtering region 170 uses a plurality of first flow port groups 182. Each filter wall 192 thereby has a dedicated first flow port group 182. Providing multiple first flow ports 178 for each filter wall 192 reduces the impact of any particular first flow port 178 becoming plugged. Although reducing the number of first flow ports 178 that are associated with a particular filter wall 192 may reduce the flow rate through the corresponding filter trap chamber 190a defined by this filter wall 192, it will not totally disable the filter wall 192 in relation to its filtering function, unless all of its associated first flow ports 178 become plugged.

The various second flow ports 188 associated with the second film 184 in the filtering region 170 are disposed in the space between the various filter walls 192 that interface with and extend from the second film 184. A plurality of second flow ports 188 are disposed outwardly of (beyond) and about each filter wall 192. In the illustrated embodiment, six second flow ports 188 are disposed about each filter wall 192, with one second flow port 188 being centrally disposed between each adjacent trio of filter walls 192. Any number of second flow ports 188 may be disposed about each filter wall 192, and the second flow ports 188 may be of any appropriate size and/or configuration (e.g., to accommodate the desired number/arrangement of supports 196 and the desired flow through the MEMS filter module 166). Each filter wall 192 is thereby also associated with multiple second flow ports 188. Providing multiple second flow ports 188 for each filter wall 192 reduces the impact of any particular second flow port 188 becoming plugged on a given filter wall 192. It should be appreciated that any particular second flow port 188 used by the filtering region 170 in effect could be used to provide a flow to or receive a flow from any filter trap chamber 190a. That is, each second flow port 188 disposed about a particular filter wall 192 could become plugged, and a flow could still be received from or directed to the corresponding filter trap chamber 190a about which this particular filter wall 192 is disposed. Reducing the number of second flow ports 188 that are available may of course reduce the flow rate through the MEMS filter module 166.

Based upon the foregoing, it should be appreciated that the first flow ports 178, second flow ports 188, filter walls 192, and supports 196 are distributed throughout the filtering region 170 of the MEMS filter module 166 in a repeating pattern. One way to characterize this pattern is that the first flow port groups 182, filter walls 192, and supports 196 are disposed in a plurality of rows 198, and a plurality of second flow ports 188 are disposed about the filter walls 192 in each row 198 in the same manner. These rows 198 are disposed in parallel relation and are also equally spaced. Any number of rows 198 may be utilized in the filtering region 170 (fours rows 198 in the illustrated embodiment). The first flow port groups 182 are equally spaced in each row 198, and the same spacing between adjacent first flow port groups 182 is used in each row 198. The filter walls 192 are also equally spaced in each row 198, and the same spacing between adjacent filter walls 192 is used in each row 198. The supports 196 are also equally spaced in each row 198, and the same spacing between adjacent support posts 196 is used in each row 198.

There is a "staggered" relation of the first flow port groups 182, filter walls 192, and supports 196 between adjacent rows 198. Specifically, each first flow port group 182 in one row 198 is disposed "midway" between adjacent pairs of first flow port groups 182 in an adjacent row 198, each filter wall 192 in one row 198 is disposed "midway" between adjacent pairs of filter walls 192 in an adjacent row 198, and each support 196 in one row 198 is disposed "midway" between adjacent pairs of supports 196 in an adjacent row 198. The first flow port groups 182, filter walls 192, and supports 196 in one row 198 also may be described as being 180 degrees "out-of-phase" with the first flow port groups 182, filter walls 192, and supports 196 in each adjacent row 198. It should be appreciated that there may be instances where there are not complete repeats of the above-noted pattern. Another option would be for the first flow port groups 182 and filter walls 192 to be disposed in a plurality of rows and in a plurality of columns, where the rows extend perpendicularly to the direction in which the columns extend (not illustrated, but similar to the pattern of the embodiment of FIGS. 4A-F), although the pattern illustrated in relation to FIGS. 5A-E increases the density of the filter walls 192 in the filtering region 170.

FIGS. 6A-D illustrate one embodiment of a MEMS filter module 200 having a filtering region 204. The MEMS filter module 200 includes a first film 208 and a second film 220 that are disposed in spaced relation or at different elevations. Each of these films 208, 220 defines an extreme for the MEMS filter module 200 in both the filtering region 204 and in its perimeter region (not shown, but in accordance with the perimeter region 42 of the MEMS filter module 34 of FIGS. 2A-F). As such, the films 208, 220 would be interconnected and supported about their respective perimeter regions by each annular seal 66 used by the MEMS filter module 200. The films 208, 220 are thereby "continuous" structures in the same manner discussed above in relation to the films 70, 46.

The first film 208 includes a plurality of first flow ports 212, while the second film 220 includes a plurality of second flow ports 224. Any number of first flow ports 212 and second flow ports 224 may be used, and these may be of any appropriate size and/or configuration (e.g., to accommodate the desired number/arrangement of supports 232 and the desired flow through the MEMS filter module 200). All of the first flow ports 212 and all of the second flow ports 224 are located only in the filtering region 204 of the MEMS filter module 200 (i.e., not in the perimeter region 42). A plurality of supports 232 extend between and structurally interconnect the first film 208 and the second film 220 in the filtering region 204. These supports 232 are distributed throughout the filtering region 204 in a repeating pattern, are disposed in spaced relation to each other, and may be of any appropriate configuration. A filter wall grid 227 is defined by a plurality of annular filter wall sections 228, and is attached to and extends from the second film 220 and at least toward (in the direction of) the first film 208. Any number of filter wall sections 228 may be utilized. Although any number of supports 232 may be utilized as well, the number and location of the support posts 232 is subject to the characterizations discussed above in relation to the supports 78. The supports 232 are subject to a number of additional characterizations as well. One is that either a single support 232 or a pair of supports 232 is positioned inwardly of each annular filter wall section 228. Another is that a single support 232 is disposed within each annular filter wall section 228 having either no second flow ports 224 enclosed thereby or a pair of second flow ports 224 enclosed thereby. Yet another is that a pair of supports 232 are disposed within each annular filter wall section 228 having a single second flow port 224 enclosed thereby.

Each filter wall section 228 has an annular configuration. "Annular" in this context means that each filter wall section 228 has a closed perimeter when looking at the distal end of the filter wall grid 227 (that which is opposite the end of the filter wall grid 227 that interfaces with the second film 220). Stated another way, each filter wall section 228 extends a full 360 degrees about a certain reference axis along any appropriate path. Although each filter wall section 228 has a rectangular, annular extent in the illustrated embodiment, any configuration could be utilized for the filter wall section 228 to realize the noted annular extent (e.g., square, circular, oval, triangular). The filter wall grid 227 (and thereby each annular filter wall section 228) also does not extend all the way to the first film 208. Instead, a filter trap or a filter trap gap 230 exists between the distal end of the filter wall grid 227 (and thereby each annular filter wall section 228) and the first film 208. Since each filter wall section 228 is annular, its corresponding filtering trap 230 will likewise be annular. Note that each filter wall section 228 is also offset from the various first flow ports 212 and second flow ports 224, thereby inducing at least one change in direction for the flow through the MEMS filter module 200.

Flow may be directed through each filter trap gap 230 to provide a filtering function. Any constituent in the flow (e.g., particulates, cells of a certain size) that is larger than the height of a particular filter trap gap 230 will typically be collectively retained by the corresponding filter wall section 228 and the first film 208 (i.e., by being unable to pass through the filter trap gap 230). Since each filter trap 230 is annular in the case of the MEMS filter module 200, any constituent that is "trapped" by being unable to pass through a particular filter trap gap 230 will then not totally "plug" the filter trap gap 230. Having an annular filter trap gap 230 associated with each filter wall section 228 also provides a desired flow rate through the MEMS filter module 200. The number and location of the various supports 232 is preferably selected such that the height of each filter trap gap 230 throughout the filtering region 204 is maintained within a small tolerance for the maximum flow rate for which the MEMS filter module 200 is designed in the same manner discussed above in relation to the filter trap gap 58.

The flow may enter the MEMS filter module 200 either through the second flow ports 224 (in which case the flow out of the MEMS filter module 200 would be through the first flow ports 212), or through the first flow ports 212 (in which case the flow out of the filter module 200 would be through the second flow ports 224). In either case, the flow will be directed into a space 226 that extends from the first film 208 to the second film 220 before attempting to pass through a filter trap gap 230 associated with a particular filter wall section 228. Each of these spaces 226 in the filtering region 204 may be characterized as a filter trap chamber 226 and is bounded by an annular filter wall section 228. The height of each filter trap chamber 226 corresponds with the spacing between the first film 208 and the second film 220, which is greater than the height of the corresponding filter trap gap 230. The volume of each filter trap chamber 226 may be larger than the volume of any associated first flow port 212, and further may be larger than the volume of any associated second flow port 224, although such is not a requirement. Whether the flow enters the MEMS filter module 200 through the first flow ports 212 or the second flow ports 224, the flow will go through a filter trap chamber 226, then through a filter trap gap 230, and then through another filter trap chamber 226. Since each annular filter wall section 228 is the same size in the case of the MEMS filter module 200, the perimeter or outer boundary of each filter trap chamber 226 is likewise the same.

The plurality of first flow ports 212 are arranged relative to the plurality of second flow ports 224 such that there will be either at least one first flow port 212 associated with a particular filter trap chamber 226, or at least one second flow port 224 associated with the same filter trap chamber 226. That is, no filter trap chamber 226 will have both one or more first flow ports 212 and one or more second flow ports 224 associated therewith. In the case where a particular filter trap chamber 226 does not have a first flow port 212 associated therewith (where the projection of the associated filter wall section 228 onto the first film 208 does not encompass any first flow port 212), there will be either a single second flow port 224 associated therewith or a pair of second flow ports 224 associated therewith, depending upon the number of supports 232 (if a single support 232 is located in the filter trap chamber 226, one second flow port 224 will be disposed on each side thereof; if a pair of supports 232 are located in the filter trap chamber 226, a single second flow port 224 will extend therebetween). In the case where a particular filter trap chamber 226 does not have a second flow port 224 associated therewith (where the associated filter wall section 228 does not encompass any second flow port 224), there will be either a single first flow port 212 associated therewith or a pair of first flow ports 212 associated therewith, depending upon the number of supports 232 (if a single support 232 is located in the filter trap chamber 226, one first flow port 212 will be disposed on each side thereof; if a pair of supports 232 are located in the filter trap chamber 226, a single first flow port 212 will extend therebetween). The first flow ports 212 and second flow ports 224 are each elongate, such that a single constituent trapped therein should not totally plug the same.

Based upon the foregoing, it should be appreciated that the first flow ports 212, second flow ports 224, filter walls sections 228, and supports 232 are distributed throughout the filtering region 204 of the MEMS filter module 200 in a repeating pattern. One way to characterize this pattern is that the first flow ports 212, second flow ports 224, filter wall sections 228, and supports 232 are disposed in a plurality of rows 234 and columns 236. The rows 234 are disposed in parallel relation to each other, as are the columns 236. Any number of rows 234 and columns 236 may be utilized in the filtering region 204. The pattern in the individual rows 234 is that the number of supports 232 alternates between one and two across the row 234 (i.e., one column 236 in a particular row 234 will have a single support 232, while the adjacent columns 236 in the same row will each have two supports 232). The pattern in the individual columns 236 is that the number of supports 232 alternates between one and two proceeding within the column.236, going by pairs of rows 234 (i.e., in each column 236, there will be two rows 234 each having a single support 232, followed by two rows 234 each having a pair of supports 232). It should be appreciated that there may be instances where there are not complete repeats of this pattern.

FIGS. 7A-E illustrate one embodiment of a MEMS filter module 237 having a filtering region 238. The filter module 237 includes a first film 242 and a second film 250 that are disposed in spaced relation or at different elevations (only those portion of the films 242, 250 required to show a single filter wall 262 of the MEMS filter module 237 being shown). Each of these films 242, 250 defines an extreme for the MEMS filter module 237 in both the filtering region 238 and in its perimeter region (not shown, but in accordance with the perimeter region 42 of the MEMS filter module 34 of FIGS. 2A-F). As such, the films 242, 250 would be interconnected and supported about their respective perimeter regions by each annular seal 66 used by the filter module 237. The films 242, 250 are thereby "continuous" structures in the same manner discussed above in relation to the films 70, 46.

At least one, and typically a plurality of, filter walls 262 is attached to and extends from the second film 250 and at least toward (in the direction of) the first film 242. Any number of filter walls 262 may be utilized in the filtering region 238 of the filter module 237. The first film 242 includes a first flow port group 248 for each filter wall 262 (each in turn having a plurality of first flow ports 246), while the second film 250 includes a second flow port group 256 (each in turn having a plurality of second flow ports 254). All of the first flow ports 246 and all of the second flow ports 254 are located only in the filtering region 238 of the filter module 237 (i.e., none are in the perimeter region 42). A first support 270 is associated with each filter wall 262, and extends between and structurally interconnects the first film 242 and the second film 250 at a location that is inward of its corresponding filter wall 262. An annular support 276 (of any "annular" configuration) is also associated with each filter wall 262 as well, and extends between and structurally interconnects the first film 242 and the second film 250 outward of (beyond) and about its corresponding filter wall 262. As such, a single annular support 276 is preferably concentrically disposed about its corresponding filter wall 262, while a single first support 270 may be centrally disposed relative to both its corresponding annular support 276 and filter wall 262. It may be possible to use only the annular support 276 for each filter wall 262, instead of using both an annular support 276 and first support 270 for each filter wall 262.

Each filter wall 262 has an annular configuration. "Annular" in this context means that each filter wall 262 has a closed perimeter when looking at the distal end of the filter wall 262 (that which is opposite the end of the filter wall 262 that interfaces with the second film 250). Stated another way, each filter wall 262 extends a full 360 degrees about a certain reference axis along any appropriate path. Although each filter wall 262 has a circular, annular extent in the illustrated embodiment, any configuration could be utilized for the filter wall 262 to realize the noted annular extent (e.g., rectangular, square, oval, triangular). Each filter wall 262 also does not extend all the way to the first film 242. Instead, a filter trap or filter trap gap 266 exists between the distal end of each filter wall 262 and the first film 242. Since each filter wall 262 is annular, its corresponding filter trap gap 266 will likewise be annular. Note that each filter wall 262 is also offset from the various first flow ports 246 and second flow ports 254, thereby inducing at least one change in direction for the flow through the MEMS filter module 237.

Flow may be directed through each filter trap gap 266 to provide a filtering function. Any constituent in the flow (e.g., particulates, cells of a certain size) that is larger than the height of a particular filter trap gap 266 will typically be collectively retained by the corresponding filter wall 262 and the first film 242 (i.e., being unable to pass through the filter trap gap 266). Since each filter trap gap 266 is annular in the case of the MEMS filter module 237, any constituent that is "trapped" by being unable to pass through a particular filter trap gap 266 will then not totally "plug" the filter trap gap 266. Having an annular filter trap gap 266 associated with each filter wall 262 also provides a desired flow rate through the MEMS filter module 237. The number and location of the various first supports 270 and their corresponding annular support 276 is preferably selected such that the height of each filter trap gap 266 throughout the filtering region 238 is maintained within a small tolerance for the maximum flow rate for which the filter module 237 is designed in the same manner discussed above in relation to the filter trap gap 58.

The flow may enter the MEMS filter module 237 either through the second flow port group(s) 256 (in which case the flow out of the MEMS filter module 237 would be through the first flow port group(s) 248), or through the first flow port group(s) 248 (in which case the flow out of the MEMS filter module 237 would be through the second flow port group(s) 256). In either case, the flow will be directed into either a space 258a or a space 258b that extends from the first film 242 to the second film 250 before attempting to pass through a filter trap gap 266 associated with a particular filter wall 262. Each of these spaces 258a, 258b in the filtering region 238 may be characterized as a filter trap chamber 258a or a filter trap chamber 258b. The height of each filter trap chamber 258a, 258b corresponds with the spacing between the first film 242 and the second film 250, which is greater than the height of its corresponding filter trap gap 266. The volume of each filter trap chamber 258a may be larger than the volume of each first flow port 246 in its corresponding first flow port group 248, while the volume of each filter trap chamber 258b may be larger than the volume of each second flow port 254 in its corresponding second flow port group 256, although such is not a requirement. The filter trap chamber 258a is in direct fluid communication with its corresponding first flow port group 248, while the filter trap chamber 258b is in direct fluid communication with its corresponding second flow port group 256. Therefore, whether the flow enters the MEMS filter module 237 through a first flow port group(s) 248 or a second flow port group(s) 256, the flow will go through one filter trap chamber 258a or 258b, then through a filter trap gap 266, and then through the other corresponding filter trap chamber 258a or 258b.

A plurality of first flow ports 246 are fluidly interconnected with each filter trap chamber 258a, and define a first flow port group 248. Any number of first flow ports 246 may be in each first flow port group 248, and the first flow ports 246 may be of any appropriate size and/or configuration (e.g., to accommodate the desired number/arrangement of supports 270, 276 and the desired flow through the MEMS filter module 237). The filtering region 238 again will typically use a plurality of first flow port groups 248. Each filter wall 262 thereby has a dedicated first flow port group 248. Providing multiple first flow ports 246 for each filter wall 262 reduces the impact of any particular first flow port 246 becoming plugged. Although reducing the number of first flow ports 246 that are associated with a particular filter wall 262 may reduce the flow rate through the corresponding filter trap chamber 258a, it will not totally disable the filter wall 262 in relation to its filtering function, unless all of its associated first flow ports 246 become plugged.

A plurality of second flow ports 254 are fluidly interconnected with each filter trap chamber 258b, and define a second flow port group 256. Any number of second flow ports 254 may be in each second flow port group 256, and the second flow ports 254 may be of any appropriate size and/or configuration (e.g., to accommodate the desired number/arrangement of supports 270, 276 and the desired flow through the MEMS filter module 237). The filtering region 238 again will typically use a plurality of second flow port groups 254. Each filter wall 262 thereby has a dedicated second flow port group 256. Providing multiple second flow ports 254 for each filter wall 262 reduces the impact of any particular second flow port 254 becoming plugged. Although reducing the number of second flow ports 254 that are associated with a particular filter wall 262 may reduce the flow rate through the corresponding filter trap chamber 258b, it will not totally disable the filter wall 262 in relation to its filtering function, unless all of its associated second flow ports 254 become plugged.

Typically a plurality of filter walls 262, its corresponding first support 270, its corresponding annular support 276, first flow port group 248, and second flow port group 256 will be distributed throughout the filtering region 238 of the MEMS filter module 237 in an appropriate repeating pattern. One such pattern is that used by the MEMS filter module 166 of FIGS. 5A-E (where the filtering region 238 would use a plurality of parallel rows, each having a plurality of equally spaced filter walls 262, but where the filter walls 262 of adjacent rows would be staggered or 180 degrees out of phase with the filter walls 262 in any adjacent row(s)). Another such pattern is that used by the MEMS filter module 124 of FIGS. 4A-E (where the filtering region 238 would use a plurality of parallel rows each having a plurality of equally spaced filter walls 262, as well as a plurality of parallel columns each having a plurality of equally spaced filter walls 262, with the rows extending perpendicularly relative to the columns).

FIGS. 8A-D illustrate one embodiment of a MEMS filter module 278 having a filtering region 280. The MEMS filter module 278 includes a first film 284 and a second film 296 that are disposed in spaced relation or at different elevations. Each of these films 284, 296 defines an extreme for the MEMS filter module 278 in both the filtering region 280 and in its perimeter region (not shown, but in accordance with the perimeter region 42 of the MEMS filter module 34 of FIGS. 2A-F). As such, the films 284, 296 would be interconnected and supported about their respective perimeter regions by each annular seal 66 used by the MEMS filter module 278. The films 284, 296 are thereby "continuous" structures in the same manner discussed above in relation to the films 70, 46.

The first film 284 includes a plurality of first flow ports 288, while the second film 296 includes a plurality of second flow ports 300. Any number of first flow ports 288 and second flow ports 300 may be utilized, and the same may be of any appropriate size and/or configuration (e.g., to accommodate the desired number/arrangement of supports 316 and the desired flow through the MEMS filter module 278). All of the first flow ports 288 and all of the second flow ports 300 are located only in the filtering region 280 of the filter module 278 (i.e., none are in the perimeter region 42). A plurality of supports 316 extend between and structurally interconnect the first film 284 and the second film 296 in the filtering region 280. These supports 316 are distributed throughout the filtering region 280 in a repeating pattern, are disposed in spaced relation to each other, and may be of any appropriate configuration. A filter wall grid 306 is defined by a plurality of annular filter wall sections 308, and is attached to and extends from the second film 296 and at least toward (in the direction of) the first film 284. Any number of filter wall sections 308 may be utilized. Although any number of supports 316 may be utilized as well, the number and location of the supports 316 is subject to the characterizations discussed above in relation to the supports 78. The supports 316 are subject to a number of additional characterizations as well. One is that either a single support 316 or a pair of support posts 316 is positioned inwardly of each annular filter wall section 308. Another is that a single support 316 is disposed within each annular filter wall section 308 having a pair of second flow ports 300 enclosed thereby and no first flow ports 288 included in an area defined by the projection of the annular filter wall section 308 onto the first film 284. Another is that a pair of supports 316 are disposed within each annular filter wall section 308 having no second flow port 300 enclosed thereby and a pair of first flow ports 288 included in an area defined by the projection of the annular filter wall section 308 onto the first film 284.

Each filter wall section 308 has an annular configuration. "Annular" in this context means that each filter wall section 308 has a closed perimeter when looking at the distal end of the filter wall grid 306 (that which is opposite the end of the filter wall grid 306 that interfaces with the second film 296). Stated another way, each filter wall section 308 extends a full 360 degrees about a certain reference axis along any appropriate path. Although each filter wall section 308 has a rectangular, annular extent in the illustrated embodiment, any configuration could be utilized for the filter wall section 308 to realize the noted annular extent (e.g., square, circular, oval, triangular). The filter wall grid 306 (and thereby each annular filter wall section 308) also does not extend all the way to the first film 284. Instead, a filter trap or a filter trap gap 312 exists between the distal end of the filter wall grid 306 (and thereby each annular filter wall section 308) and the first film 284. Since each filter wall section 308 is annular, its corresponding filter trap 312 will likewise be annular. Note that each filter wall section 308 is also offset from the various first flow ports 288 and second flow ports 300, thereby inducing at least one change in direction for the flow through the MEMS filter module 278.

Flow may be directed through each filter trap gap 312 to provide a filtering function. Any constituent in the flow (e.g., particulates, cells of a certain size) that is larger than the height of a particular filter trap gap 312 will typically be collectively retained by the corresponding filter wall section 308 and the first film 284 (i.e., being unable to pass through the filter trap gap 312). Since each filter trap gap 312 is annular in the case of the MEMS filter module 278, any constituent that is "trapped" by being unable to pass through a particular filter trap gap 312 will then not totally "plug" the filter trap gap 312. Having an annular filter trap gap 312 associated with each filter wall section 308 also provides a desired flow rate through the MEMS filter module 278. The number and location of the various supports 316 is preferably selected such that the height of each filter trap gap 312 throughout the filtering region 280 is maintained within a small tolerance for the maximum flow rate for which the MEMS filter module 278 is designed in the same manner discussed above in relation to the filter trap gap 58.

The flow may enter the MEMS filter module 278 either through the second flow ports 300 (in which case the flow out of the MEMS filter module 278 would be through the first flow ports 288), or through the first flow ports 288 (in which case the flow out of the MEMS filter module 278 would be through the second flow ports 300). In either case, the flow will be directed into a space 304 that extends from the first film 284 to the second film 296 before attempting to pass through a filter trap gap 312 associated with a particular filter wall section 308. Each of these spaces 304 in the filtering region 280 may be characterized as a filter trap chamber 304 and is bounded by an annular filter wall section 308. The height of each filter trap chamber 304 corresponds with the spacing between the first film 284 and the second film 296, which is greater than the height of the filter trap gap 312. The volume of each filter trap chamber 304 may be larger than the volume of any associated first flow port 288, and further may be larger than the volume of any associated second flow port 300, although such is not a requirement. Whether the flow enters the MEMS filter module 278 through the first flow ports 288 or the second flow ports 300, the flow will go through a filter trap chamber 304, then through a filter trap gap 312, and then through another filter trap chamber 304. Since each annular filter wall section 308 is the same size in the case of the filter module 278, the perimeter or outer boundary of each filter trap chamber 304 is likewise the same.

The plurality of first flow ports 288 are arranged relative to the plurality of second flow ports 300 such that there will be either at least one first flow port 288 associated with a particular filter trap chamber 304, or at least one second flow port 300 associated with the same filter trap chamber 304. That is, no filter trap chamber 304 will have both one or more first flow ports 288 and one or more second flow ports 300 associated therewith (see FIGS. 8C and 8D, where section $S_1$ of the filter wall grid 306 is identified for a frame of reference in each of FIGS. 8C-8D). In the case where a particular filter trap chamber 304 does not have a first flow port 288 associated therewith (where the projection of the associated filter wall section 308 onto the first film 284 does not encompass any first flow port 288), there will be a pair of second flow ports 300 associated therewith in the illustrated embodiment. In the case where a particular filter trap chamber 304 does not have a second flow port 300 associated therewith (where the associated filter wall section 308 does not encompass any second flow port 300), there will be a pair of first flow ports 288 associated therewith in the illustrated embodiment (where the projection of the associated filter wall section 308 onto the first film 284 encompasses a pair of first flow ports 288). The first flow ports 288 and second flow ports 300 are each elongate, such that a single constituent trapped therein should not totally plug the same.

Based upon the foregoing, it should be appreciated that the first flow ports 288, second flow ports 300, filter walls sections 308, and support posts 316 are distributed throughout the filtering region 280 of the filter module 278 in a repeating pattern. One way to characterize this pattern is that the first flow ports 288, second flow ports 300, filter wall sections 308, and supports 316 are disposed in a plurality of rows 317 and columns 318, with the columns 318 extending perpendicularly to the direction in which the rows 317 extend. The rows 317 are disposed in parallel relation to each other, as are the columns 318. Any number of rows 317 and columns 318 may be utilized in the filtering region 280. The pattern in the individual rows 317 is that: 1) the same number of first flow ports 288, second flow ports 300, and supports 316 is the same for each annular filter wall section 308 in the row 317; and 2) the rows 317 alternate by having either a pair of supports 316, a pair of second flow ports 300, and no first flow ports 288 for each annular filter wall section 308, or a single support post 316, no second flow ports 300, and a pair of first flow ports 288 for each annular filter wall section 308. It should be appreciated that there may be instances where there are not complete repeats of the above-noted pattern.

FIGS. 9A-E illustrate one embodiment of a MEMS filter module 319 having a filtering region 320. The filter module 319 includes a first film 324, a plurality of second film sections 332, and a third film 336 that are disposed in spaced relation or at different elevations, with the plurality of second film sections 332 being located at an intermediate elevation between the first film 324 and the third film 336. The first film 324 and the third film 336 define an extreme for the filter module 319 in both the filtering region 320 and in its perimeter region (not shown, but in accordance with the perimeter region 42 of the MEMS filter module 34 of FIGS. 2A-F). As such, the films 324, 336 would be interconnected and supported about their respective perimeter regions by each annular seal 66 used by the filter module 166. The films 324, 336 are thereby "continuous" structures in the same manner discussed above in relation to the films 70, 46. The plurality of second film sections 332 in the illustrated embodiment, on the other hand, do not define a continuous structure (i.e., there is an annular gap (second flow passage 334) about each second film section 332). Adjacent second film sections 332 could be structurally interconnected by one or more links (not shown), but in a manner to accommodate the desired flow through the MEMS filter module 319. In this case, multiple flow passages would be provided about each second film section 332.

The first film 324 includes a plurality of first flow ports 328, each of the plurality of second film sections 332 has an annular second flow passage 334 disposed thereabout, and the third film 336 includes a plurality of third flow ports 340. All of the first flow ports 328, all of the second flow passages 334, and all of the third flow ports 340 are located only in the filtering region 320 of the MEMS filter module 319 (i.e., none are in the perimeter region 42). A lower support 330 extends between and structurally interconnects the first film 324 and each individual second film section 332 in the filtering region 320. These lower supports 330 are distributed throughout the filtering region 320 in a repeating pattern, are disposed in spaced relation to each other, and may be of any appropriate configuration. An upper support 356 extends between and structurally interconnects the third film 336 and each individual second film section 332 in the filtering region 320. These upper supports 356 are distributed throughout the filtering region 320 in a repeating pattern, are disposed in spaced relation to each other, and may be of any appropriate configuration.

A plurality of filter walls 348 are attached to and extend from the third film 336 and at least toward (in the direction of) the corresponding second film section 332. That is, there is a one-to-one relation between the filter walls 348 and the second film sections 332 (i.e., each filter wall 348 is associated with a separate second film section 332). Any number of filter walls 348 (and thereby second film sections 332) may be utilized in the filtering region 320 of the filter module 319. Although any number of supports 330, 356 may be utilized as well, the number and location of the supports 330, 356 is subject to the characterizations discussed above in relation to the supports 78. The supports 330, 356 are subject to a number of additional characterizations as well. One is that a single upper support 356 is positioned inwardly of each filter wall 348 in a central location, and a single lower support 330 is axially aligned with each upper support 356 so as to be centrally disposed relative to the filter wall 348 as well.

Each filter wall 348 has an annular configuration. "Annular" in this context means that each filter wall 348 has a closed perimeter when looking at the distal end of the filter wall 348 (that which is opposite the end of the filter wall 348 that interfaces with the third film 336). Stated another way, each filter wall 348 extends a full 360 degrees about a certain reference axis along any appropriate path. Although each filter wall 348 has a hexagonal, annular extent in the illustrated embodiment, any configuration could be utilized for the filter wall 348 to realize the noted annular extent (e.g., rectangular, square, oval, triangular). Each filter wall 348 also does not extend all the way to its corresponding second film section 332. Instead, a filter trap or filter trap gap 352 exists between the distal end of each filter wall 348 and its corresponding second film section 332. Since each filter wall 348 is annular, its corresponding filter trap gap 352 will likewise be annular. Note that each filter wall 348 is also offset from the various first flow ports 328, thereby inducing at least one change in direction for the flow through the MEMS filter module 319.

Flow may be directed through each filter trap gap 352 to provide a filtering function. Any constituent in the flow (e.g., particulates, cells of a certain size) that is larger than the height of a particular filter trap gap 352 will typically be collectively retained by the corresponding filter wall 348 and the second film section 332 (i.e., being unable to pass through the filter trap gap 352). Since each filter trap 352 is annular in the case of the MEMS filter module 319, any constituent that is "trapped" by being unable to pass through a particular filter trap gap 352 will then not totally "plug" the filter trap gap 352. Having an annular filter trap gap 352 associated with each filter wall 348 also provides a desired flow rate through the MEMS filter module 319. The number and location of the various supports 330, 356 is preferably selected such that the height of each filter trap gap 352 throughout the filtering region 320 is maintained within a small tolerance for the maximum flow rate for which the MEMS filter module 319 is designed in the same manner discussed above in relation to the filter trap gap 58.

The flow may enter the filter module 319 either through the third flow ports 340 (in which case the flow out of the MEMS filter module 319 would be through the first flow ports 328), or through the first flow ports 328 (in which case the flow out of the filter module 319 would be through the third flow ports 340). In either case, the flow will be directed into either a space 344a or a space 344b before attempting to pass through a filter trap gap 352 associated with a particular filter wall 348. Each of these spaces 344a, 344b in the filtering region 320 may be characterized as a filter trap chamber 344a, 344b. The height of each filter trap chamber 344a corresponds with the spacing between the third film 336 and its corresponding second film section 332 (and bounded by a particular filter wall 348), which is greater than the height of the associated filter trap gap 352. The height of the filter trap chamber 344b corresponds with the spacing between the first film 324 and the various second film sections 332, which is greater than the height of any of the filter trap gaps 352 as well. The volume of each filter trap chamber 344a may be larger than the volume of any associated third flow port 340, while the volume of the filter trap chamber 344b may be larger than the volume of any associated first flow port 328, although such is not a requirement. Whether the flow enters the filter module 319 through the first flow ports 328 or the third flow ports 340, the flow will go through either the filter trap chambers 344a or the filter trap chamber 344b, then through the corresponding filter trap gap 352, and then through the other the other of the filter trap chamber 344a or the filter trap chamber 344b.

A plurality of third flow ports 340 are fluidly interconnected with each filter trap chamber 344a. Any number of third flow ports 340 may be utilized, and the third flow ports 340 may be of any appropriate size and/or configuration (e.g., to accommodate the desired number/arrangement of supports 356 and the desired flow through the MEMS filter module 319). The filtering region 320 uses a plurality of third flow port groups 342. Each filter wall 348 thereby has a dedicated third flow port group 342. Providing multiple third flow ports 340 for each filter wall 348 reduces the impact of any particular third flow port 340 becoming plugged. Although reducing the number of third flow ports 340 that are associated with a particular filter wall 348 may reduce the flow rate through the corresponding filter trap chamber 344a defined by this filter wall 348, it will not totally disable the filter wall 348 in relation to its filtering function, unless all of its associated third flow ports 340 become plugged.

An annular second flow passage 334 is disposed about each second film section 332. Having an annular second flow passage 334 for each filter wall 348 reduces the impact of a portion of this annular second flow passage 334 becoming plugged, although it may of course have an effect on the flow rate through the filter module 319. In addition, each annular second flow passage 334 is not dedicated to a specific filter trap chamber 344a. Therefore, the entirety of a particular annular second flow passage 334 could become plugged, without disabling in the corresponding filter trap gap 352. Again, the plugging of an entire second flow passage 334 could have an effect on the flow rate through the filter module 319.

Each filter wall 348 is also associated with multiple first flow ports 328. Any number of first flow ports 328 may be utilized, and the first flow ports 328 may be of any appropriate size and/or configuration (e.g., to accommodate the desired number/arrangement of supports 330 and the desired flow through the MEMS filter module 319).Providing multiple first flow ports 328 for each filter wall 348 reduces the impact of any particular first flow port 328 becoming plugged on a given filter wall 348. It should be appreciated that any particular first flow port 328 used by the filtering region 320 in effect could be used to provide a flow to or receive a flow from any filter trap chamber 344a. Reducing the number of first flow ports 328 that are available may of course reduce the flow rate through the MEMS filter module 319.

Based upon the foregoing, it should be appreciated that the first flow ports 328, annular second flow passages 334, filter walls 348, and support posts 330, 356 are distributed throughout the filtering region 320 of the filter module 319 in a repeating pattern that is in accordance with the pattern used in the filtering region 170 for the filter module 166 of FIGS. 5A-E. Therefore, the above-noted discussion regarding this pattern is equally applicable to the filtering region 320 of the filter module 319 of FIGS. 9A-E. In one embodiment, the MEMS filter module 319 may be modified so as to not utilize the first film 324 and the various lower supports 330 (not shown).

Figure 10A:
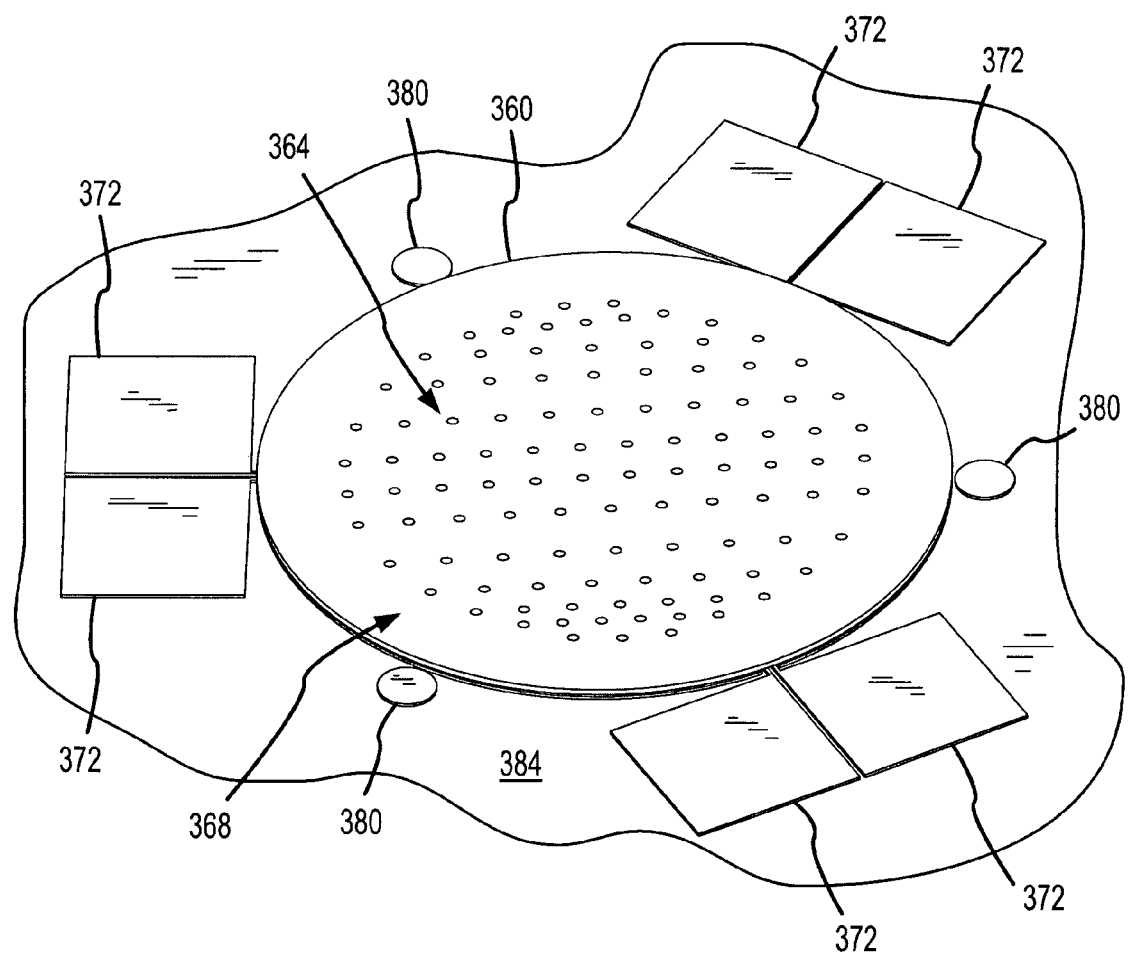
FIG. 10A is a perspective view of one embodiment of an interface between a MEMS filter module and a substrate on which the MEMS filter module is fabricated.
Figure 10B:
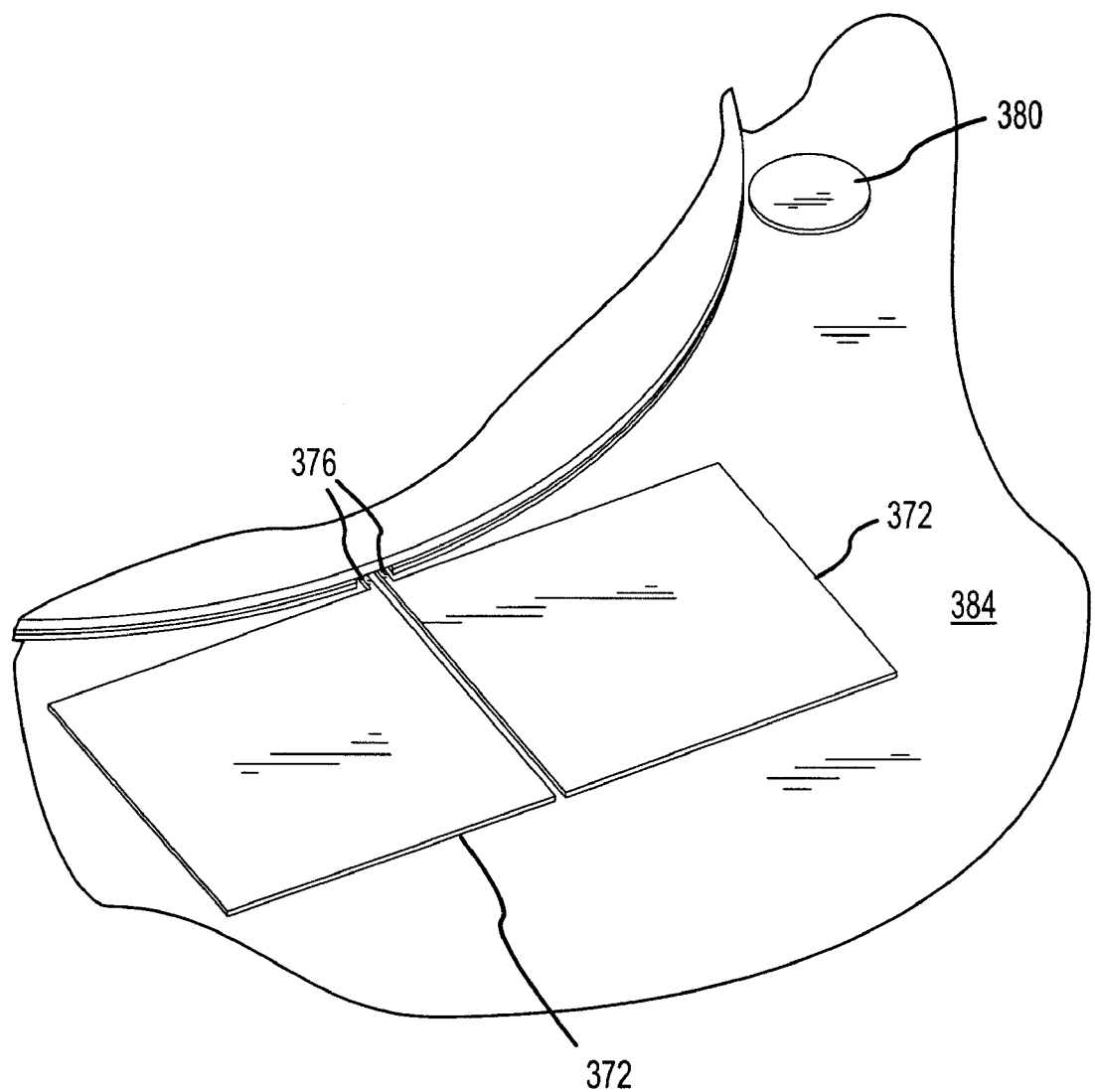
FIG. 10B is an enlarged, perspective view of one of the lateral motion constraints and the links used to support the MEMS filter module of FIG. 10A above the substrate.

Each of the various MEMS filter modules described herein may be fabricated by surface micromachining as previously noted and as generally described above in relation to FIGS. 3A-I. The MEMS filter module need not be structurally interconnected with the underlying substrate other than by an underlying layer of sacrificial material. Removal of this sacrificial material in the etch release at the end of fabrication will thereby separate the MEMS filter module from the substrate. Another option would be for the lowest film of the MEMS filter module being fabricated to remain disposed in spaced relation to the substrate after the etch release (e.g., FIG. 3I). That is, the MEMS filter module may be supported above the substrate in an appropriate manner. One way in which this may be done is illustrated in FIGS. 10A-B. A MEMS filter module 360 of the type described herein includes a filtering region 364 and a perimeter region 368. This MEMS filter module 360 is supported above a substrate 384. In this regard, a plurality of bond pads 372 are anchored to the substrate 384, extend upwardly from the substrate 384, and are disposed beyond a perimeter of the MEMS filter module 360. A link 376 extends from each bond pad 372 to the MEMS filter module 360. Each link 376 may be of any appropriate configuration and may be disposed at any appropriate elevation relative to the substrate 384. The links 376 thereby suspend the MEMS filter module 360 above the substrate 384. When it is desired to remove the MEMS filter module 360 from the substrate 384, the bond pads 372 are contacted by appropriate electrodes. The resulting electrical signal fractures each link 376, and as such the MEMS filter module 360 "falls" onto the substrate 384. A plurality of motion limiters 380 are anchored to the substrate 384, extend upwardly therefrom, and are disposed about the MEMS filter module 360 to constrain the motion of the MEMS filter module 360 in the lateral dimension once positioned directly on the substrate 384. The motion limiters 380 may be of any appropriate configuration. The MEMS filter module 360 may then be retrieved from the substrate 384 in any appropriate way (e.g., by moving the MEMS filter module 360 at least principally in the vertical dimension and away from the substrate 384).

Figure 11A:
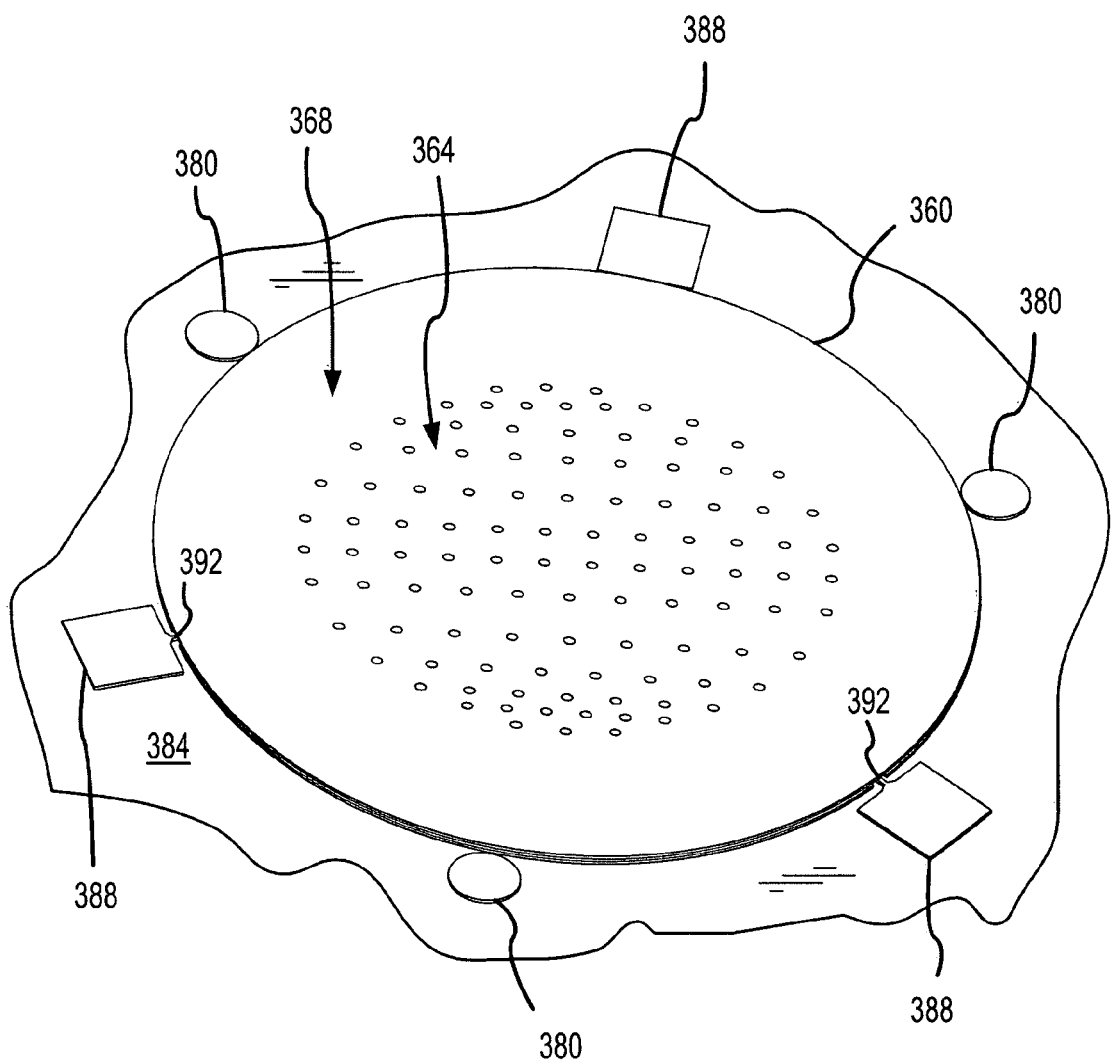
FIG. 11A is a perspective view of another embodiment of an interface between a MEMS filter module and a substrate on which the MEMS filter module is fabricated.
Figure 11B:
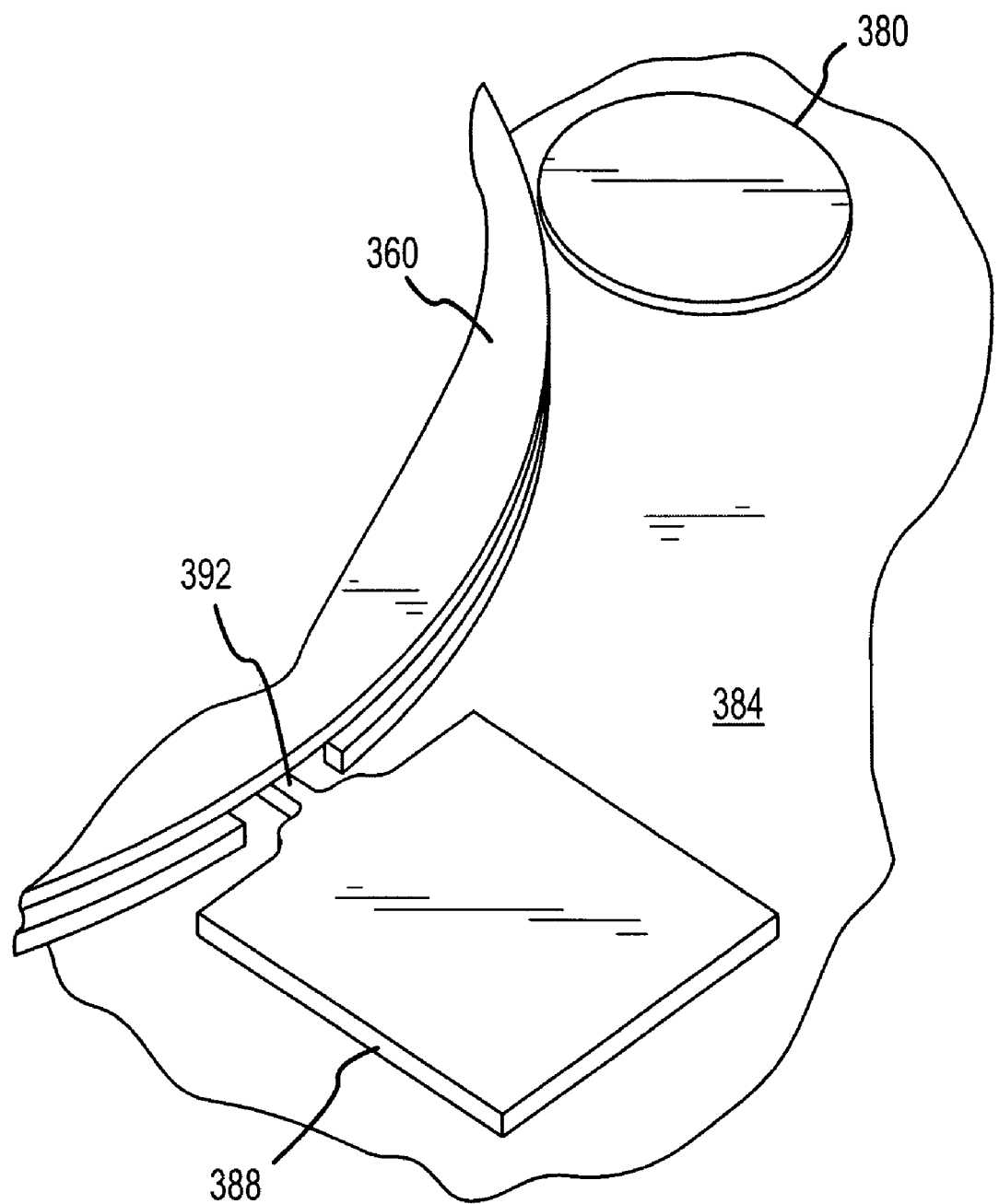
FIG. 11B is an enlarged, perspective view of one of the lateral motion constraints and the links used to support the MEMS filter module of FIG. 11A above the substrate.

FIGS. 11A-B present another option for supporting the MEMS filter module 360 above the substrate 384 after the etch release. In this case, a plurality of filter module anchors 388 are fabricated on and extend outwardly from the substrate 384 at a location so as to be disposed about a perimeter of the MEMS filter module 360. These filter module anchors 388 may be in any appropriate configuration. A link 392 extends from each filter module anchor 388 to the MEMS filter module 360. The links 392 may be of any appropriate configuration and may be disposed at appropriate elevation above the substrate 384. When it is desired to remove the MEMS filter module 360 from the substrate 384, an appropriate force may be exerted on the MEMS filter module 360 (e.g., one that is at least generally orthogonal to the underlying substrate 384). This force will fracture each link 392, and as such the MEMS filter module 360 may "fall" onto the substrate 384. A plurality of motion limiters 380 again are anchored to the substrate 384 and are disposed about the MEMS filter module 360 to constrain the motion of the MEMS filter module 360 in the lateral dimension once on the substrate 384. The filter module 360 may then be retrieved from the substrate 384 in any appropriate way (e.g., by moving the MEMS filter module 360 at least principally in the vertical dimension and away from the substrate 384).

Surface micromachining is the preferred technology for fabricating the above-described MEMS filter modules. In this regard, these MEMS filter modules may be fabricated in at least two different levels that are disposed at different elevations (hereafter a first fabrication level and a second fabrication level). "Fabrication level" corresponds with what may be formed by a deposition of a structural material before having to form an overlying layer of a sacrificial material (e.g., from a single deposition of a structural layer or film). Generally, each of these MEMS filter modules includes a first film with at least one first flow port extending therethrough, a second film with at least one second flow port extending therethrough, and at least one filter wall that extends from the second film in the direction of the first film such that the filter wall and first film cooperate to define a filter trap. The first film may be fabricated at least in the first fabrication level, while the second film may be fabricated in at least the second fabrication level. It should be appreciated that the characterization of the first film being in a "first fabrication level" and the second film being in the "second fabrication level" by no means requires that the first fabrication level be that which is deposited "first", and that the second fabrication level be that which is deposited "second." Moreover, it does not require that the first fabrication level and the second fabrication level be immediately adjacent.

The first and second films each may exist in a single fabrication level or may exist in multiple fabrication levels. In the above-noted first instance, a deposition of a structural material in a single fabrication level may define an at least generally planar layer. Another option regarding the first instance would be for the deposition of a structural material in a single fabrication level to define an at least generally planar portion, plus one or more structures that extend down toward, but not to, the underlying structural layer at the underlying fabrication level (e.g., a second film with one or more filter walls extending from the second film and in the direction of the first film). In either situation and prior to the release, in at least some cases there will be at least some thickness of sacrificial material disposed between the entirety of a filter wall and the first film.

In the above-noted second instance, two or more structural layers or films from adjacent fabrication levels could be disposed in direct interfacing relation (e.g., one directly on the other). Over the region that is to define the first or second film, this would require removal of the sacrificial material that is deposited on the structural material at one fabrication level before depositing the structural material at the next fabrication level. Another option regarding the above-noted second instance would be to maintain the separation between structural layers or films in different fabrication levels for the first and/or second films, but provide an appropriate structural interconnection therebetween (e.g., a plurality of columns, posts, or the like extending between adjacent structural layers or films in different fabrication levels).

Figure 12A:
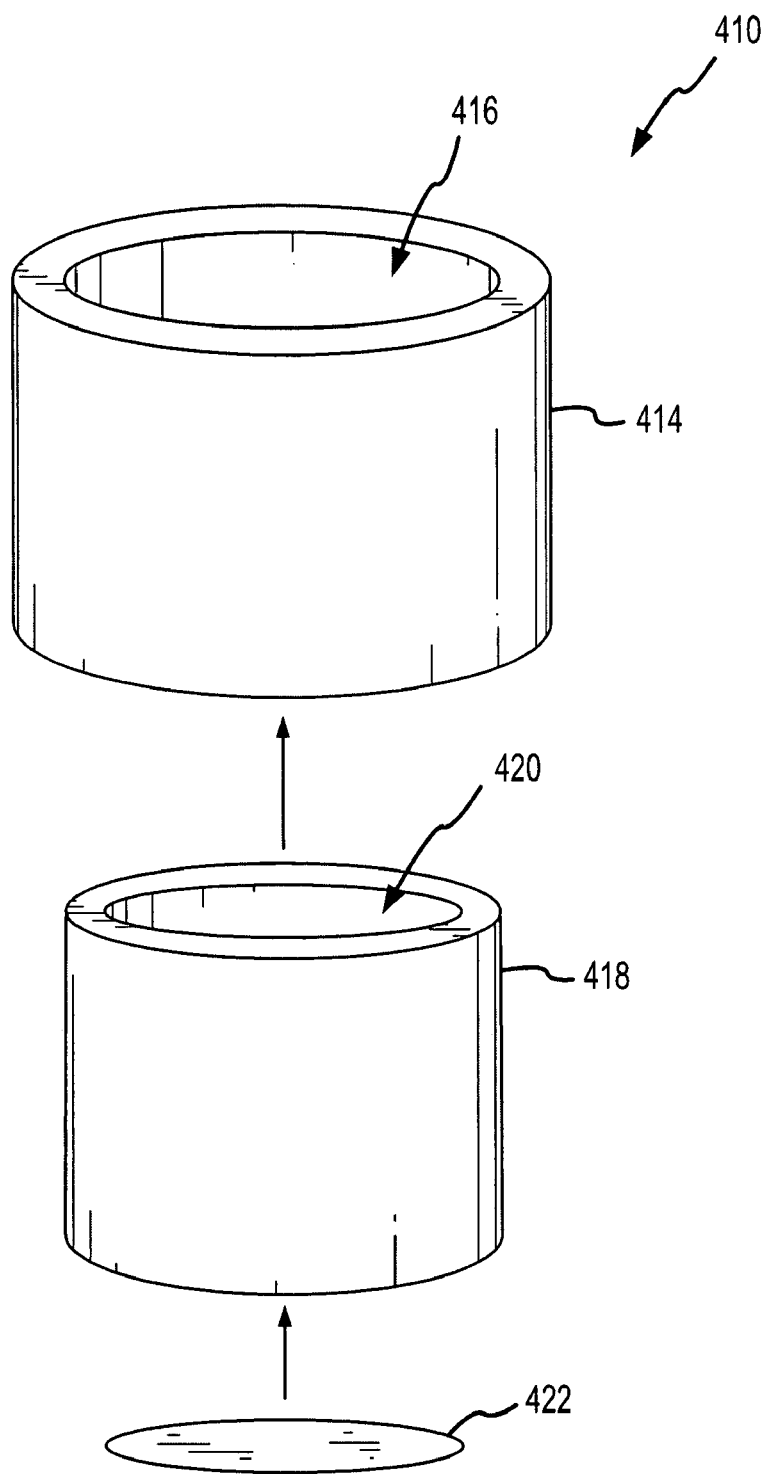
FIG. 12A is an exploded, perspective view of one embodiment of a flow assembly that uses a MEMS filter module.
Figures 12B, 14A:
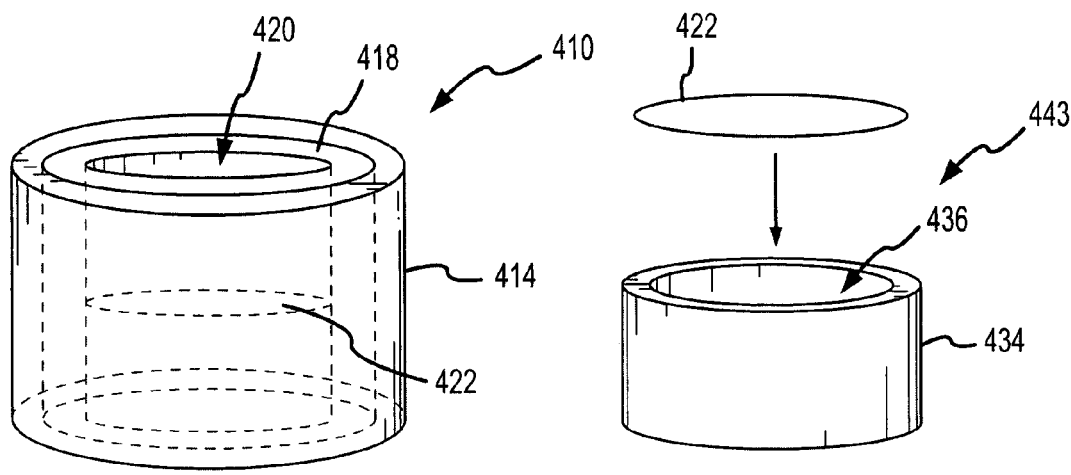
FIG. 12B is a perspective view of the flow assembly of FIG. 12A in an assembled condition.
FIG. 14A is an exploded, perspective of another embodiment of a flow assembly that uses a MEMS filter module.

FIGS. 12A-B schematically represent one embodiment of a flow assembly 410 that may be used for any appropriate application (e.g., the flow assembly 410 may be disposed in a flow of any type, may be used to filter and/or control the flow of a fluid of any type, may be located in a conduit that fluidly interconnects multiple sources of any appropriate type (e.g., between multiple fluid or pressure sources (including where one is the environment), such as a man-made reservoir, a biological reservoir, the environment, or any other appropriate source), or any combination thereof). One example would be to dispose the flow assembly 410 in a conduit extending between the anterior chamber of an eye and a location that is exterior of the cornea of the eye. Another example would be to dispose the flow assembly 410 in a conduit extending between the anterior chamber of an eye and another location that is exterior of the sclera of the eye. Yet another example would be to dispose the flow assembly 410 in a conduit extending between the anterior chamber of an eye and another location within the eye (e.g., into Schlemm's canal) or body. In each of these examples, the conduit would provide an exit path for aqueous humor when installed for a glaucoma patient. That is, each of these examples may be viewed as a way of treating glaucoma or providing at least some degree of control of the intraocular pressure.

Components of the flow assembly 410 include an outer housing 414, an inner housing 418, and a MEMS filter module 422. Any of the MEMS filter module described herein may be used in place of the MEMS filter module 422, including without limitation the MEMS filter modules 34, 124, 166, 200, 237, 278, 319, 360. The position of the MEMS filter module 422 and the inner housing 418 are at least generally depicted within the outer housing 414 in FIG. 12B to show the relative positioning of these components in the assembled condition—not to convey that the outer housing 414 needs to be in the form of a transparent structure. All details of the MEMS filter module 422 and the inner housing 418 are not necessarily illustrated in FIG. 12B.

The MEMS filter module 422 is only schematically represented in FIGS. 12A-B, and provides at least a filtering function. The MEMS filter module 422 may be of any appropriate design, size, shape, and configuration, and further may be formed from any material or combination of materials that are appropriate for use by the relevant microfabrication technology. Any appropriate coating or combination of coatings may be applied to exposed surfaces of the MEMS filter module 422 as well. For instance, a coating may be applied to improve the biocompatibility of the MEMS filter module 422, to make the exposed surfaces of the MEMS filter module 422 more hydrophilic, to reduce the potential for the MEMS filter module 422 causing any bio-fouling, or any combination thereof. In one embodiment, a self assembled monolayer coating (e.g., poly-ethylene-glycol) is applied in any appropriate manner (e.g., liquid or vapor phase, with vapor phase being the preferred technique) to all exposed surfaces of the MEMS filter module 422. The main requirement of the MEMS filter module 422 is that it is a MEMS device.

The primary function of the outer housing 414 and inner housing 418 is to provide structural integrity for the MEMS filter module 422 or to support the MEMS filter module 422, and further to protect the MEMS filter module 422. In this regard, the outer housing 414 and inner housing 418 each will typically be in the form of a structure that is sufficiently rigid to protect the MEMS filter module 422 from being damaged by the forces that reasonably could be expected to be exerted on the flow assembly 410 during its assembly, as well as during use of the flow assembly 410 in the application for which it was designed.

The inner housing 418 includes a hollow interior or a flow path 420 that extends through the inner housing 418 (between its opposite ends in the illustrated embodiment). The MEMS filter module 422 may be disposed within the flow path 420 through the inner housing 418 in any appropriate manner and at any appropriate location within the inner housing 418 (e.g., at any location so that the inner housing 418 is disposed about the MEMS filter module 422). Preferably, the MEMS filter module 422 is maintained in a fixed position relative to the inner housing 418. For instance, the MEMS filter module 422 may be attached or bonded to an inner sidewall or a flange formed on this inner sidewall of the inner housing 418, a press-fit could be provided between the inner housing 418 and the MEMS filter module 422, or a combination thereof The MEMS filter module 422 also could be attached to an end of the inner housing 418 in the manner of the embodiment of FIGS. 14A-B that will be discussed in more detail below.

The inner housing 418 is at least partially disposed within the outer housing 414 (thereby encompassing having the outer housing 414 being disposed about the inner housing 418 along the entire length of the inner housing 418, or only along a portion of the length of the inner housing 418). In this regard, the outer housing 414 includes a hollow interior 416 for receiving the inner housing 418, and possibly to provide other appropriate functionality (e.g., a flow path fluidly connected with the flow path 420 through the inner housing 418). The outer and inner sidewalls of the outer housing 414 may be cylindrical or of any other appropriate shape, as may be the outer and inner sidewalls of the inner housing 418. The inner housing 418 may be retained relative to the outer housing 414 in any appropriate manner. For instance, the inner housing 418 may be attached or bonded to an inner sidewall of the outer housing 414, a press-fit could be provided between the inner housing 418 and the outer housing 414, a shrink fit could be provided between the outer housing 414 and the inner housing 418, or a combination thereof.

The inner housing 418 is likewise only schematically represented in FIGS. 12A-B, and it may be of any appropriate shape/configuration, of any appropriate size, and formed from any material or combination of materials (e.g., polymethylmethacrylate (PMMA), ceramics, silicon, titanium, and other implantable metals and plastics). Typically its outer contour will be adapted to match the inner contour of the outer housing 414 in which it is at least partially disposed. In one embodiment, the illustrated cylindrical configuration for the inner housing 418 is achieved by cutting an appropriate length from hypodermic needle stock. The inner housing 418 also may be microfabricated into the desired/required shape (e.g., using at least part of a LIGA process). However, any way of making the inner housing 418 may be utilized. It should also be appreciated that the inner housing 418 may include one or more coatings as desired/required as well (e.g., an electroplated metal; a coating to improve the biocompatibility of the inner housing 418, to make the exposed surfaces of the inner housing 418 more hydrophilic, to reduce the potential for the inner housing 418 causing any bio-fouling, or any combination thereof). In one embodiment, a self assembled monolayer coating (e.g., poly-ethylene-glycol) is applied in any appropriate manner (e.g., liquid or vapor phase, with vapor phase being the preferred technique) to all exposed surfaces of the inner housing 418.

The outer housing 414 likewise is only schematically represented in FIGS. 12A-B, and it may be of any appropriate shape/configuration, of any appropriate size, and formed from any material or combination of materials (e.g., polymethylmethacrylate (PMMA), ceramics, silicon, titanium, and other implantable metals and plastics). Typically its outer contour will be adapted to match the inner contour of the housing or conduit in which it is at least partially disposed or otherwise mounted. The outer housing 414 also may be microfabricated into the desired/required shape (e.g., using at least part of a LIGA process). However, any way of making the outer housing 414 may be utilized. It should also be appreciated that the outer housing 414 may include one or more coatings as desired/required as well (e.g., an electroplated metal; a coating to improve the biocompatibility of the outer housing 414, to make the exposed surfaces of the outer housing 414 more hydrophilic, to reduce the potential for the outer housing 414 causing any bio-fouling, or any combination thereof). In one embodiment, a self assembled monolayer coating (e.g., poly-ethylene-glycol) is applied in any appropriate manner (e.g., liquid or vapor phase, with vapor phase being the preferred technique) to all exposed surfaces of the outer housing 414.

Figure 13A:
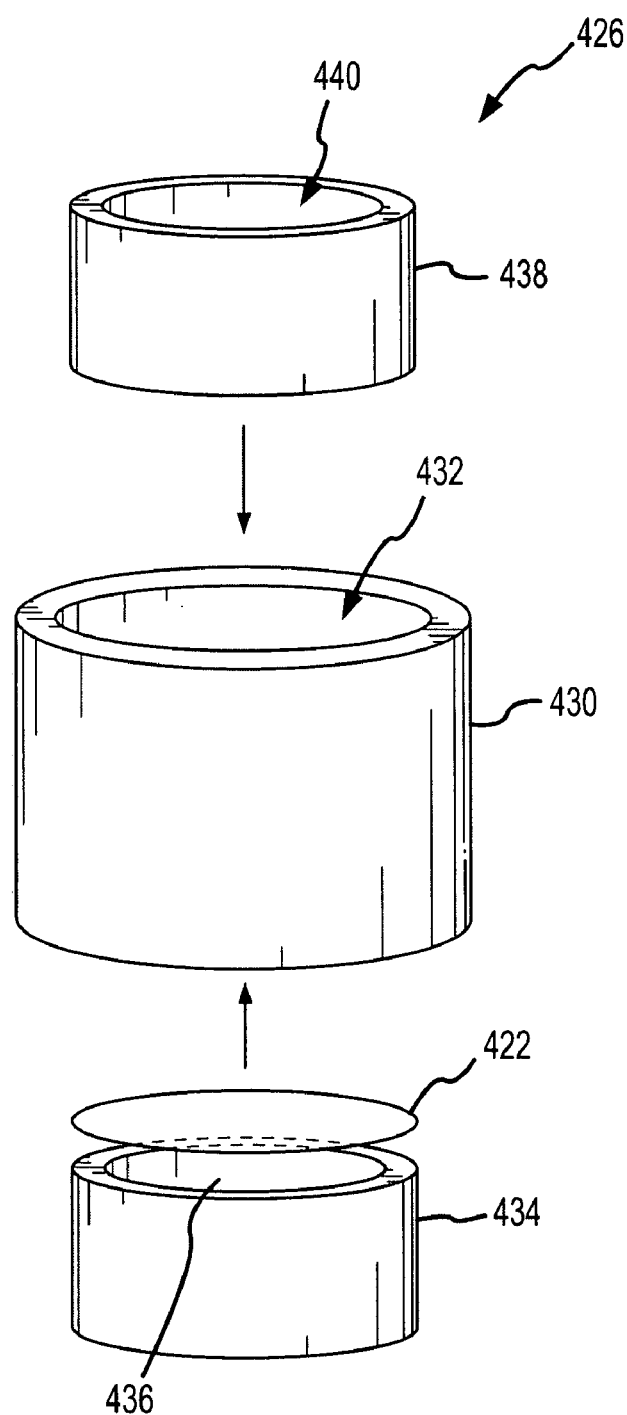
FIG. 13A is an exploded, perspective of another embodiment of a flow assembly that uses a MEMS filter module.
Figures 13B, 14B:
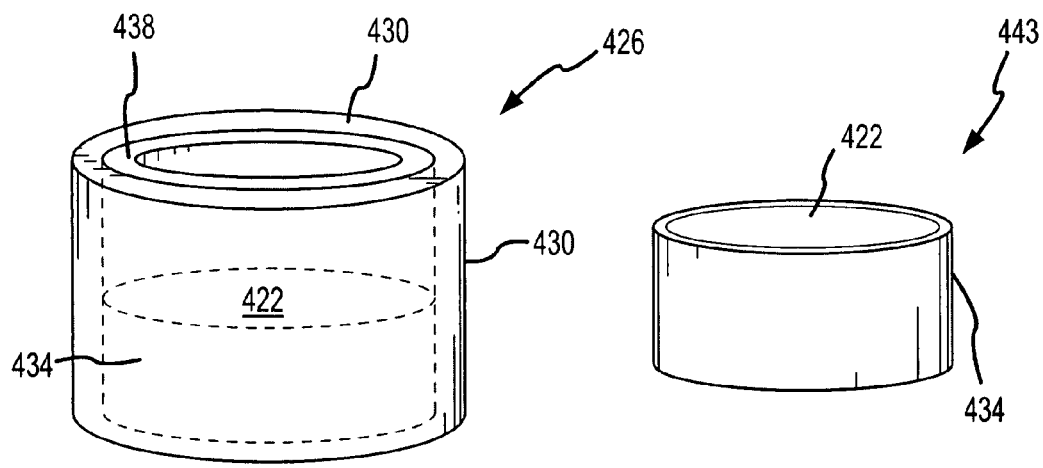
FIG. 13B is a perspective view of the flow assembly of FIG. 13A in an assembled condition.
FIG. 14B is a perspective view of the flow assembly of FIG. 14A in an assembled condition.

Another embodiment of a flow assembly is illustrated in FIGS. 13A-B (only schematic representations), and is identified by reference numeral 426. The flow assembly 426 may be used for any appropriate application (e.g., the flow assembly 426 may be disposed in a flow of any type, may be used to filter a flow of a fluid of any type, may be located in a conduit that fluidly interconnects multiple sources of any appropriate type (e.g., multiple fluid or pressure sources (including where one is the environment), such as a manmade reservoir, a biological reservoir, the environment, or any other appropriate source), or any combination thereof). The above-noted applications for the flow assembly 410 are equally applicable to the flow assembly 426. The types of coatings discussed above in relation to the flow assembly 410 may be used by the flow assembly 426 as well.

Components of the flow assembly 426 include an outer housing 430, a first inner housing 434, a second inner housing 438, and the MEMS filter module 422. The MEMS filter module 422 and the inner housings 434, 438 are at least generally depicted within the outer housing 430 in FIG. 13B to show the relative positioning of these components in the assembled condition—not to convey that the outer housing 430 needs to be in the form of a transparent structure. All details of the MEMS filter module 422 and the inner housings 434, 438 are not necessarily illustrated in FIG. 13B.

The primary function of the outer housing 430, first inner housing 434, and second inner housing 438 is to provide structural integrity for the MEMS filter module 422 or to support the MEMS filter module 422, and further to protect the MEMS filter module 422. In this regard, the outer housing 430, first inner housing 434, and second inner housing 438 each will typically be in the form of a structure that is sufficiently rigid to protect the MEMS filter module 422 from being damaged by the forces that reasonably could be expected to be exerted on the flow assembly 426 during its assembly, as well as during use of the flow assembly 426 in the application for which it was designed.

The first inner housing 434 includes a hollow interior or a flow path 436 that extends through the first inner housing 434. Similarly, the second inner housing 438 includes a hollow interior or a flow path 440 that extends through the second inner housing 438. The first inner housing 434 and the second inner housing 438 are disposed in end-to-end relation, with the MEMS filter module 422 being disposed between adjacent ends of the first inner housing 434 and the second inner housing 438. As such, a flow progressing through the first flow path 436 to the second flow path 440, or vice versa, passes through the MEMS filter module 422.

Preferably, the MEMS filter module 422 is maintained in a fixed position relative to each inner housing 434, 438, and its perimeter does not protrude beyond the adjacent sidewalls of the inner housings 434, 438 in the assembled and joined condition. For instance, the MEMS filter module 422 may be bonded to at least one of, but more preferably both of, the first inner housing 434 (more specifically one end thereof) and the second inner housing 438 (more specifically one end thereof) to provide structural integrity for the MEMS filter module 422 (e.g., using cyanoacrylic esters, thermal bonding, UV-curable epoxies, or other epoxies). Another option would be to fix the position the MEMS filter module 422 in the flow assembly 426 at least primarily by fixing the position of each of the inner housings 434, 438 relative to the outer housing 430 (i.e., the MEMS filter module 422 need not necessarily be bonded to either of the housings 434, 438). In one embodiment, an elastomeric material may be disposed between the MEMS filter module 422 and the first inner housing 434 to allow the first inner housing 434 with the MEMS filter module 422 disposed thereon to be pushed into the outer housing 430 (e.g., the elastomeric material is sufficiently "tacky" to at least temporarily retain the MEMS filter module 422 in position relative to the first inner housing 434 while being installed in the outer housing 430). The second inner housing 438 also may be pushed into the outer housing 430 (before, but more likely after, the first inner housing 434 is disposed in the outer housing 430) to "sandwich" the MEMS filter module 422 between the inner housings 434, 438 at a location that is within the outer housing 430 (i.e., such that the outer housing 430 is disposed about MEMS filter module 422). The MEMS filter module 422 would typically be contacted by both the first inner housing 434 and the second inner housing 438 when disposed within the outer housing 430. Fixing the position of each of the first inner housing 434 and the second inner housing 438 relative to the outer housing 430 will thereby in effect fix the position of the MEMS filter module 422 relative to the outer housing 430. Both the first inner housing 434 and second inner housing 438 are at least partially disposed within the outer housing 430 (thereby encompassing the outer housing 430 being disposed about either or both housings 434, 438 along the entire length thereof, or only along a portion of the length of thereof), again with the MEMS filter module 422 being located between the adjacent ends of the first inner housing 434 and the second inner housing 438. In this regard, the outer housing 430 includes a hollow interior 432 for receiving at least part of the first inner housing 434, at least part of the second inner housing 438, and the MEMS filter module 422 disposed therebetween, and possibly to provide other appropriate functionality (e.g., a flow path fluidly connected with the flow paths 236, 240 through the first and second inner housings 434, 438, respectively). The outer and inner sidewalls of the outer housing 430 may be cylindrical or of any other appropriate shape, as may be the outer and inner sidewalls of the inner housings 434, 438. Both the first inner housing 434 and the second inner housing 438 may be secured to the outer housing 430 in any appropriate manner, including in the manner discussed above in relation to the inner housing 418 and the outer housing 414 of the embodiment of FIGS. 12A-B.

Each inner housing 434, 438 is likewise only schematically represented in FIGS. 13A-B, and each may be of any appropriate shape/configuration, of any appropriate size, and formed from any material or combination of materials in the same manner as the inner housing 418 of the embodiment of FIGS. 12A-B. Typically the outer contour of both housings 434, 438 will be adapted to match the inner contour of the outer housing 430 in which they are at least partially disposed. In one embodiment, the illustrated cylindrical configuration for the inner housings 434, 438 is achieved by cutting an appropriate length from hypodermic needle stock. The inner housings 434, 438 each also may be microfabricated into the desired/required shape (e.g., using at least part of a LIGA process). However, any way of making the inner housings 434, 438 may be utilized. It should also be appreciated that the inner housings 434, 438 may include one or more coatings as desired/required as well in accordance with the foregoing.

The outer housing 430 is likewise only schematically represented in FIGS. 13A-B, and it may be of any appropriate shape/configuration, of any appropriate size, and formed from any material or combination of materials in the same manner as the outer housing 414 of the embodiment of FIGS. 12A-B. Typically the outer contour of the outer housing 430 will be adapted to match the inner contour of the housing or conduit in which it is at least partially disposed or otherwise mounted. The outer housing 430 may be microfabricated into the desired/required shape (e.g., using at least part of a LIGA process). However, any way of making the outer housing 430 may be utilized. It should also be appreciated that the outer housing 430 may include one or more coatings as desired/required in accordance with the foregoing.

Another embodiment of a flow assembly is illustrated in FIGS. 14A-B (only schematic representations), and is identified by reference numeral 443. The flow assembly 443 may be used for any appropriate application (e.g., the flow assembly 443 may be disposed in a flow of any type, may be used to filter a flow of a fluid of any type, may be located in a conduit that fluidly interconnects multiple sources of any appropriate type (e.g., between multiple fluid or pressure sources, such as a man-made reservoir, a biological reservoir, the environment, or any other appropriate source), or any combination thereof). Components of the flow assembly 443 include the above-noted housing 434 and the MEMS filter module 422 from the embodiment of FIGS. 13A-B. In the case of the flow assembly 443, the MEMS filter module 422 is attached or bonded to one end of the housing 434 (e.g., using cyanoacrylic esters, thermal bonding, UV-curable epoxies, or other epoxies). The flow assembly 443 may be disposed within an outer housing in the manner of the embodiments of FIGS. 12A-13B, or could be used "as is." The above-noted applications for the flow assembly 410 are equally applicable to the flow assembly 443. The types of coatings discussed above in relation to the flow assembly 410 may be used by the flow assembly 443 as well.

One particularly desirable application for the flow assemblies 410, 426, and 443 of FIGS. 12A-14B, as discussed above, is for use with an implant that is installed to address the pressure within the anterior chamber of an eye. That is, they may be disposed in an exit path through which aqueous humor travels to treat a glaucoma patient. Preferably, the flow assemblies 410, 426, 443 each provide a bacterial filtration function to reduce the potential for developing an infection within the eye. Although the various housings and MEMS filter modules used by the flow assemblies 410, 426, and 443 each may be of any appropriate color, it may be desirable for the color to be selected so as to "blend in" with the eye to at least some extent.

Figures 15A, 15B:
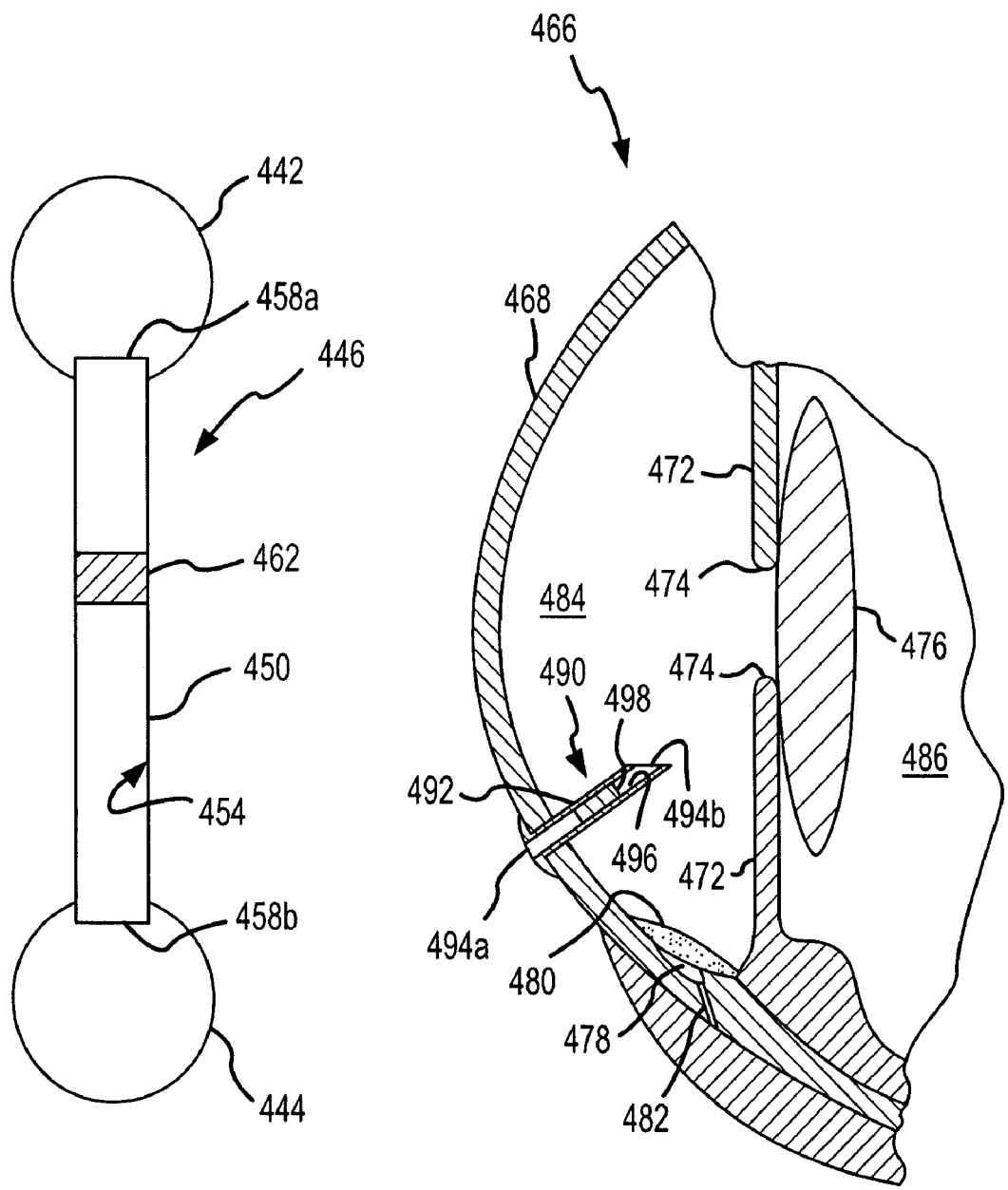
FIG. 15A is a schematic of one embodiment of a glaucoma or intraocular implant that may use any of the MEMS filter modules described herein.
FIG. 15B is a cross-sectional view of one embodiment of a glaucoma or intraocular implant or shunt that is used to relieve pressure within the anterior chamber of the eye, and that may utilize any of the MEMS filter modules described herein.

An example of the above-noted application is schematically illustrated in FIG. 15A. Here, an anterior chamber 442 of a patient's eye (or other body region for that matter—a first body region) is fluidly interconnected with an appropriate drainage area at 444 by an implant 446 (a "glaucoma implant" for the specifically noted case). The drainage area 444 may be any appropriate location, such as externally of the eye (e.g., on an exterior surface of the cornea), within the eye (e.g., Schlemm's canal), or within the patient's body in general (a second body region).

Generally, the implant 446 includes a conduit 450 having a pair of ends 458a, 458b, with a flow path 454 extending therebetween. The size, shape, and configuration of the conduit 450 may be adapted as desired/required, including to accommodate the specific drainage area at 444 being used. Representative configurations for the conduit 450 are disclosed in U.S. Patent Application Publication No. 2003/0212383, as well as U.S. Pat. Nos. 3,788,327; 5,743,868; 5,807,302; 6,626,858; 6,638,239; 6,533,768; 6,595,945; 6,666,841; and 6,736,791, the entire disclosures of which are incorporated by reference in their entirety herein.

A flow assembly 462 is disposed within the flow path 454 of the conduit 450. All flow leaving the anterior chamber 442 through the implant 446 is thereby directed through the flow assembly 462. Similarly, any flow from the drainage area at 444 into the implant 446 will have to pass through the flow assembly 462. The flow assembly 462 may be retained within the conduit 450 in any appropriate manner and at any appropriate location (e.g., it could be disposed on either end 458a, 458b, or any intermediate location therebetween). The flow assembly 462 may be in the form of any of the flow assemblies 410, 426, or 443 discussed above, replacing the MEMS filter module 422 with any of the MEMS filter modules 34, 124, 166, 200, 237, 278, 319, 360. Alternatively, the flow assembly 462 could simply be in the form of the MEMS filter modules 34, 124, 166, 200, 237, 278, 319, 360. Any appropriate coating may be applied to at least those surfaces of the implant 446 that would be exposed to biological material/fluids, including without limitation a coating that improves biocompatibility, that makes such surfaces more hydrophilic, and/or that reduces the potential for bio-fouling. In one embodiment, a self-assembled monolayer coating (e.g., poly-ethylene-glycol) is applied in any appropriate manner (e.g., liquid or vapor phase, with vapor phase being the preferred technique) to the noted surfaces.

FIG. 15B illustrates a representative embodiment in accordance with FIG. 15A. Various portions of the eye 466 are identified in FIG. 15B, including the cornea 468, iris 472, pupil 474, lens 476, anterior chamber 484, posterior chamber 486, Schlemm's canal 478, trabecular meshwork 480, and aqueous veins 482. Here, a glaucoma implant or shunt 490 having an appropriately-shaped conduit 492 is directed through the cornea 468. The conduit 492 may be in any appropriate form, but will typically include at least a pair of ends 494a, 494b, as well as a flow path 496 extending therebetween. End 494a is disposed on the exterior surface of the cornea 468, while end 494b is disposed within the anterior chamber 484 of the eye 466.

A flow assembly 498 is disposed within the flow path 496 of the conduit 492. All flow leaving the anterior chamber 484 through the shunt 490 is thereby directed through the flow assembly 498. Similarly, any flow from the environment back into the shunt 490 will have to pass through the flow assembly 498 as well. Preferably, the flow assembly 498 provides a bacterial filtration function to reduce the potential for developing an infection within the eye when using the implant 490. The flow assembly 498 may be retained within the conduit 492 in any appropriate manner and at any appropriate location (e.g., it could be disposed on either end 494a, 494b, or any an intermediate location therebetween). The flow assembly 498 may be in the form of any of the flow assemblies 410, 426, or 443 discussed above, replacing the MEMS filter module 422 with any of the MEMS filter modules 34, 124, 166, 200, 237, 278, 319, 360. Alternatively, the flow assembly 498 could simply be in the form of the MEMS filter modules 34, 124, 166, 200, 237, 278, 319, 360. Any appropriate coating may be applied to at least those surfaces of the shunt 490 that would be exposed to biological material/fluids, including without limitation a coating that improves biocompatibility, that makes such surfaces more hydrophilic, and/or that reduces the potential for bio-fouling. In one embodiment, a self-assembled monolayer coating (e.g., poly-ethylene-glycol) is applied in any appropriate manner (e.g., liquid or vapor phase, with vapor phase being the preferred technique) to the noted surfaces.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An implant for addressing pressure within a first body region, comprising:
   a conduit comprising a first flow path and adapted to fluidly communicate with the first body region; and
   a MEMS filter module disposed within said first flow path, wherein said MEMS filter module comprises:
   a first film comprising at least one first flow port;
   a second film comprising at least one second flow port, wherein said second film is spaced from said first film; and
   a first filter wall that extends from said second film at least toward said first film, wherein a gap between said first filter wall and said first film defines a filter trap, and wherein said first filter wall is of an annular extent in a plan view.

2. An implant, as claimed in claim 1, wherein said first film and said second film each have a maximum thickness of about 10 microns.

3. An implant, as claimed in claim 1, wherein said first and second films define opposing extremes of said MEMS filter module.

4. An implant, as claimed in claim 1, further comprising:
   a first chamber fluidly connected with said at least one first flow port; and
   a second chamber fluidly connected with said at least one second flow port, wherein said filter trap fluidly interconnects said first and second chambers.

5. An implant, as claimed claim 4, wherein said first and second chambers are disposed on opposite sides of said first filter wall.

6. An implant, as claimed in claim 1, wherein said first filter wall terminates prior to reaching a surface of said first film that faces said second film.

7. An implant, as claimed in claim 1, wherein an area defined by projecting said first filter wall onto said first film fails to encompass any said first flow port.

8. An implant, as claimed in claim 1, wherein at least two said first flow ports and at least two said second flow ports are associated with said filter trap.

9. An implant, as claimed in claim 1, wherein said gap is no more than about 0.4 microns.

10. An implant for addressing pressure within a first body region, comprising:
    a conduit comprising a first flow path and adapted to fluidly communicate with the first body region; and
    a MEMS filter module disposed within said first flow path, wherein said MEMS filter module comprises:
    a first film comprising at least one first flow port;
    a second film comprising at least one second flow port, wherein said second film is spaced from said first film;
    a first filter wall that extends from said second film at least toward said first film, wherein a gap between said first filter wall and said first film defines a filter trap;
    a first annular seal extending between said first and second films of said MEMS filter module; and
    a filtering region bounded by said first annular seal, wherein said first filter wall, said filter trap, each said first flow port, and each said second flow port are located in said filtering region.

11. An implant, as claimed in claim 10, further comprising:
    a second annular seal extending between said first and second films of said MEMS filter module and disposed in spaced relation to said first annular seal, wherein said second annular seal is disposed outwardly of said first annular seal.

12. An implant, as claimed in claim 10, wherein said MEMS filter module further comprises a plurality of supports extending between said first and second films in said filtering region.

13. An implant for addressing pressure within a first body region, comprising:
    a conduit comprising a first flow path and adapted to fluidly communicate with the first body region; and a MEMS filter module disposed within said first flow path, wherein said MEMS filter module comprises:
   a first film comprising at least one first flow port;
   a second film comprising at least one second flow port, wherein said second film is spaced from said first film;
   a first filter wall that extends from said second film at least toward said first film, wherein a gap between said first filter wall and said first film defines a filter trap; and
   a plurality of supports extending between said first and second films.

14. An implant, as claimed in claim 13, wherein said MEMS filter module further comprises a plurality of said first filter walls.

15. An implant, as claimed in claim 14, wherein a number of said supports is no less than a number of said first filter walls.

16. An implant, as claimed in claim 14, wherein each said first filter wall is of an annular extent.

17. An implant, as claimed in claim 14, wherein each said first filter wall is disposed about at least one of said supports.

18. An implant, as claimed in claim 1, further comprising:
a first housing; and
a second housing at least partially disposed within said first housing, wherein said second housing comprises a second flow path that fluidly communicates with said first flow path of said conduit, wherein said MEMS filter module is associated with said second housing such that all flow through said second flow path is directed through said MEMS filter module, wherein said first housing is at least partially disposed within said first flow path of said conduit.

19. An implant, as claimed in claim 18, wherein said first housing comprises first and second ends, as well as an opening extending between said first and second ends, wherein said second housing is disposed within said opening.

20. An implant, as claimed in claim 18, wherein said first and second housing are each rigid.

21. An implant, as claimed in claim 18, wherein said first and second housings are each formed from a material selected from the group consisting of polymethylmethacrylate, ceramics, silicon, titanium, implantable metals, and implantable plastics.

22. An implant, as claimed in claim 18, wherein said MEMS filter module is recessed within said second housing.

23. An implant, as claimed in claim 18, wherein said second housing comprises first and second ends, wherein said second flow path extends between said first and second ends, and wherein said MEMS filter module is disposed somewhere between said first and second ends within said second housing.

24. An implant, as claimed in claim 18, wherein said second housing comprises first and second ends, wherein said second flow path extends between said first and second ends, and wherein said MEMS filter module is disposed on said first end of said second housing.

25. An implant, as claimed in claim 24, further comprising:
   a third housing at least partially disposed within said first housing, wherein said third housing comprises a third flow path, wherein said MEMS filter module is sandwiched between said second and third housings, and thereby between said second and third flow paths.

26. An implant, as claimed in claim 18, wherein said MEMS filter module is maintained in a fixed position relative to said second housing.

27. An implant, as claimed in claim 18, wherein said MEMS filter module is bonded to said second housing.

28. An implant, as claimed in claim 1, further comprising:
   a housing at least partially disposed within said conduit and comprising first and second ends, wherein said housing comprises a second flow path that fluidly communicates with said first flow path of said conduit and that extends between said first and second ends, wherein said MEMS filter module is mounted on said first end of said second housing such that all flow through said second flow path is directed through said MEMS filter module.

29. An implant, as claimed in claim 1, wherein the first body region is an anterior chamber of an eye.

30. An implant for addressing pressure within a first body region, comprising:
   a conduit comprising a first flow path and adapted to fluidly communicate with the first body region; and
   a MEMS filter module disposed within said first flow path, wherein said MEMS filter module comprises:
      a first structure; and
      a second structure that is displaced from said first structure by a first space that defines a filter trap, wherein said first and second structures are maintained in an at least substantially fixed position relative to each other, and wherein at least part of a flow through said MEMS filter module passes through said first space;
   wherein said first structure comprises a first film that in turn comprises at least one first flow port, wherein said second structure comprises a second film that in turn comprises at least one second flow port, wherein said second film is spaced from said first film, wherein said second structure further comprises a first filter wall that extends from said second film at least toward said first film, wherein said first filter wall and said first film are separated by said first space, and wherein said first filter wall is of an annular extent in a plan view.

31. An implant, as claimed in claim 30, wherein said first film and said second film each have a maximum thickness of about 10 microns.

32. An implant, as claimed in claim 30, wherein said first and second films define opposing extremes of said MEMS filter module.

33. An implant, as claimed in claim 30, further comprising:
   a first chamber fluidly connected with said at least one first flow port; and
   a second chamber fluidly connected with said at least one second flow port, wherein said first space fluidly interconnects said first and second chambers.

34. An implant, as claimed claim 33, wherein said first and second chambers are disposed on opposite sides of said first filter wall.

35. An implant, as claimed in claim 30, wherein said first filter wall terminates prior to reaching a surface of said first film that faces said second film.

36. An implant, as claimed in claim 30, wherein an area defined by projecting said first filter wall onto said first film fails to encompass any said first flow port.

37. An implant, as claimed in claim 30, wherein at least two said first flow ports and at least two said second flow ports are associated with said first space.

38. An implant, as claimed in claim 30, wherein a height of said first space is no more than about 0.4 microns.

39. An implant, for addressing pressure within a first body region, comprising:
- a conduit comprising a first flow path and adapted to fluidly communicate with the first body region; and
- a MEMS filter module disposed within said first flow path, wherein said MEMS filter module comprises:
  - a first structure;
  - a second structure that is displaced from said first structure by a first space that defines a filter trap, wherein said first and second structures are maintained in an at least substantially fixed position relative to each other, and wherein at least part of a flow through said MEMS filter module passes through said first space;
  - wherein said first structure comprises a first film that in turn comprises at least one first flow port, wherein said second structure comprises a second film that in turn comprises at least one second flow port, wherein said second film is spaced from said first film, wherein said second structure further comprises a first filter wall that extends from said second film at least toward said first film, and wherein said first filter wall and said first film are separated by said first space;
  - a first annular seal extending between said first and second films of said MEMS filter module; and
  - a filtering region bounded by said first annular seal, wherein said first filter wall, said filter trap, each said first flow port, and each said second flow port are located in said filtering region.

40. An implant, as claimed in claim 39, further comprising:
- a second annular seal extending between said first and second films of said MEMS filter module and disposed in spaced relation to said first annular seal, wherein said second annular seal is disposed outwardly of said first annular seal.

41. An implant, as claimed in claim 39, wherein said MEMS filter module further comprises a plurality of supports extending between said first and second films in said filtering region.

42. An implant for addressing pressure within a first body region, comprising:
- a conduit comprising a first flow path and adapted to fluidly communicate with the first body region; and
- a MEMS filter module disposed within said first flow path, wherein said MEMS filter module comprises:
  - a first structure; and
  - a second structure that is displaced from said first structure by a first space that defines a filter trap, wherein said first and second structures are maintained in an at least substantially fixed position relative to each other, and wherein at least part of a flow through said MEMS filter module passes through said first space;
  - wherein said first structure comprises a first film that in turn comprises at least one first flow port, wherein said second structure comprises a second film that in turn comprises at least one second flow port, wherein said second film is spaced from said first film, wherein said second structure further comprises a first filter wall that extends from said second film at least toward said first film, wherein said first filter wall and said first film are separated by said first space, and wherein said second structure further comprises a plurality of supports extending between said first and second films.

43. An implant, as claimed in claim 42, wherein said MEMS filter module further comprises a plurality of said first filter walls.

44. An implant, as claimed in claim 43, wherein a number of said supports is no less than a number of said first filter walls.

45. An implant, as claimed in claim 43, wherein each said first filter wall is of an annular extent.

46. An implant, as claimed in claim 43, wherein each said first filter wall is disposed about at least one of said supports.

47. An implant, as claimed in claim 30, further comprising:
- a first housing; and
- a second housing at least partially disposed within said first housing, wherein said second housing comprises a second flow path that fluidly communicates with said first flow path of said conduit, wherein said MEMS filter module is associated with said second housing such that all flow through said second flow path is directed through said MEMS filter module, wherein said first housing is at least partially disposed within said first flow path of said conduit.

48. An implant, as claimed in claim 47, wherein said first housing comprises first and second ends, as well as an opening extending between said first and second ends, wherein said second housing is disposed within said opening.

49. An implant, as claimed in claim 47, wherein said first and second housings are each rigid.

50. An implant, as claimed in claim 47, wherein said first and second housings are each formed from a material selected from the group consisting of polymethylmethacrylate, ceramics, silicon, titanium, implantable metals, and implantable plastics.

51. An implant, as claimed in claim 47, wherein said MEMS filter module is recessed within said second housing.

52. An implant, as claimed in claim 47, wherein said second housing comprises first and second ends, wherein said second flow path extends between said first and second ends, and wherein said MEMS filter module is disposed somewhere between said first and second ends within said second housing.

53. An implant, as claimed in claim 47, wherein said second housing comprises first and second ends, wherein said second flow path extends between said first and second ends, and wherein said MEMS filter module is disposed on said first end of said second housing.

54. An implant, as claimed in claim 53, further comprising:
- a third housing at least partially disposed within said first housing, wherein said third housing comprises a third flow path, wherein said MEMS filter module is sandwiched between said second and third housings, and thereby between said second and third flow paths.

55. An implant, as claimed in claim 47, wherein said MEMS filter module is maintained in a fixed position relative to said second housing.

56. An implant, as claimed in claim 47, wherein said MEMS filter module is bonded to said second housing.

57. An implant, as claimed in claim 30, further comprising:
- a housing at least partially disposed within conduit and comprising first and second ends, wherein said housing comprises a second flow path that fluidly communicates with said first flow path of said conduit and that extends between said first and second ends, wherein said MEMS filter module is mounted on said first end of said second housing such that all flow through said second flow path is directed through said MEMS filter module.

58. An implant, as claimed in claim 30, wherein the first body region is an anterior chamber of an eye.

59. An implant for addressing pressure within a first body region, comprising:
   a conduit comprising a first flow path and adapted to fluidly communicate with the first body region; and
   a MEMS filter module disposed within said first flow path, wherein said MEMS filter module comprises:
      a first film comprising a plurality of first flow ports;
      a second film comprising a plurality of second flow ports, wherein said second film is spaced from said first film;
      a plurality of filter walls that are disposed in spaced relation on said second film, that extend from said second film toward said first film, and that are of an annular extent in a plan view of a surface of said second film from which said plurality of filter walls extend, wherein a gap between each said filter wall and said first film defines a filter trap that is thereby also of an annular extent;
      a first annular seal extending between said first and second films;
      a filtering region bounded by said first annular seal, wherein all of said filter walls, said filter traps, said first flow ports, and said second flow ports are located in said filtering region; and
      a plurality of supports extending between said first and second films in said filtering region.

60. An implant, as claimed in claim 59, wherein the first body region is an anterior chamber of an eye.

61. An implant for addressing pressure within a first body region, comprising:
   a conduit comprising a first flow path and adapted to fluidly communicate with the first body region; and
   a MEMS filter module disposed within said first flow path, wherein said MEMS flow module comprises:
      a first film comprising a plurality of first flow ports;
      a second film comprising a plurality of second flow ports, wherein said second film is spaced from said first film;
      a plurality of filter walls that are disposed in spaced relation on said second film and that extend from said second film toward said first film, wherein a gap between each said filter wall and said first film defines a filter trap;
      a first annular seal extending between said first and second films;
      a filtering region bounded by said first annular seal, wherein all of said filter walls, said filter traps, said first flow ports, and said second flow ports are located in said filtering region; and
      a plurality of supports extending between said first and second films in said filtering region, wherein a number of said posts is no less than a number of said filter walls.

62. An implant, as claimed in claim 61, wherein the first body region is an anterior chamber of an eye.

63. An implant for addressing pressure within a first body region, comprising:
   a conduit comprising a first flow path and adapted to fluidly communicate with the first body region; and
   a MEMS filter module disposed within said first flow path, wherein said MEMS filter module comprises:
      a first film comprising a plurality of first flow ports;
      a second film comprising a plurality of second flow ports, wherein said second film is spaced from said first film;
      a plurality of filter walls that are disposed in spaced relation on said second film and that extend from said second film toward said first film, wherein a gap between each said filter wall and said first film defines a filter trap, wherein at least two said first flow ports and at least two said second flow ports are associated with each said filter trap;
      a first annular seal extending between said first and second films;
      a filtering region bounded by said first annular seal, wherein all of said filter walls, said filter traps, said first flow ports, and said second flow ports are located in said filtering region; and
      a plurality of supports extending between said first and second films.

64. An implant, as claimed in claim 63, wherein the first body region is an anterior chamber of an eye.

65. An implant for addressing pressure within a first body region, comprising:
   a conduit comprising a first flow path and adapted to fluidly communicate with the first body region; and
   a MEMS filter module disposed within said first flow path, wherein said MEMS filter module comprises:
      a first film comprising a plurality of first flow ports that extend through said first film;
      a first chamber fluidly connected with at least one of said first flow ports;
      a second film comprising a plurality of second flow ports that extend through said second film, wherein said second film is spaced from said first film;
      a second chamber fluidly connected with at least one of said second flow ports;
      a first filter wall that extends from said second film in a direction of said first film, wherein said first and second chambers are disposed on opposite sides of said first filter wall;
      a first filter trap defined in part by said first filter wall, wherein said first filter trap fluidly interconnects said first and second chambers; and
      a first annular seal extending between said first and second films.

66. An implant, as claimed in claim 65, wherein the first body region is an anterior chamber of an eye.

* * * * *